(12) United States Patent
Pendri et al.

(10) Patent No.: US 9,034,882 B2
(45) Date of Patent: May 19, 2015

(54) INHIBITORS OF HUMAN IMMUNODEFICIENCY VIRUS REPLICATION

(71) Applicant: Bristol-Myers Squibb Company, Princeton, NJ (US)

(72) Inventors: Annapurna Pendri, South Glastonbury, CT (US); David R. Langley, Meriden, CT (US); Samuel Gerritz, Guilford, CT (US); Guo Li, Wallingford, CT (US); Weixu Zhai, Middletown, CT (US); Stanley D'Andrea, Wallingford, CT (US); Manoj Patel, Berlin, CT (US); B. Narasimhulu Naidu, Durham, CT (US); Kevin Peese, Haddam, CT (US); Zhongyu Wang, Vernon, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 57 days.

(21) Appl. No.: 13/782,198

(22) Filed: Mar. 1, 2013

(65) Prior Publication Data

US 2013/0231331 A1  Sep. 5, 2013

Related U.S. Application Data

(60) Provisional application No. 61/606,626, filed on Mar. 5, 2012.

(51) Int. Cl.
| | |
|---|---|
| *A01N 43/90* | (2006.01) |
| *A61K 31/519* | (2006.01) |
| *C07D 487/00* | (2006.01) |
| *C07D 487/04* | (2006.01) |
| *C07D 498/08* | (2006.01) |
| *C07D 519/00* | (2006.01) |

(52) U.S. Cl.
CPC ............ *C07D 487/04* (2013.01); *C07D 498/08* (2013.01); *C07D 519/00* (2013.01)

(58) Field of Classification Search
None
See application file for complete search history.

(56) References Cited

U.S. PATENT DOCUMENTS

| | | |
|---|---|---|
| 2008/0221159 A1 | 9/2008 | Tsantrizos et al. |
| 2010/0292227 A1 | 11/2010 | Yoakim et al. |
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0118249 A1 | 5/2011 | Tsantrizos et al. |
| 2011/0207626 A1 | 8/2011 | Inazawa et al. |
| 2012/0129840 A1 | 5/2012 | Chaltin et al. |
| 2012/0316161 A1 | 12/2012 | Carlens et al. |
| 2013/0203727 A1 | 8/2013 | Babaoglu et al. |
| 2013/0203748 A1 | 8/2013 | Naidu et al. |
| 2013/0210801 A1 | 8/2013 | Babaoglu et al. |
| 2013/0210857 A1 | 8/2013 | Walker et al. |

FOREIGN PATENT DOCUMENTS

| | | |
|---|---|---|
| WO | WO 2012/033735 | 3/2012 |
| WO | WO2012/102985 | 8/2012 |
| WO | WO2012/140243 | 10/2012 |

OTHER PUBLICATIONS

U.S. Appl. No. 13/782,996, filed Mar. 1, 2013, Zheng et al.

*Primary Examiner* — Jeffrey H Murray
(74) *Attorney, Agent, or Firm* — James Epperson

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

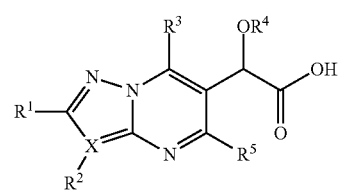

14 Claims, No Drawings

INHIBITORS OF HUMAN IMMUNODEFICIENCY VIRUS REPLICATION

CROSS-REFERENCE TO RELATED APPLICATIONS

This application claims the benefit of U.S. Provisional Application Ser. No. 61/606,626 filed Mar. 5, 2012.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33 million people worldwide are infected with the virus (UNAIDS: Report on the Global HIV/AIDS Epidemic, December 1998). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, and WO2009062308.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

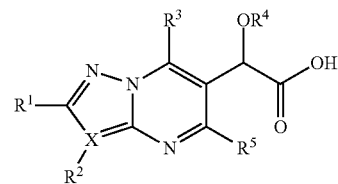

where:

X is C or N;

$R^1$ is hydrogen or $Ar^1$;

$R^2$ is hydrogen or $Ar^1$;

provided that when X is C either $R^1$ is $Ar^1$ and $R^2$ is hydrogen or $R^2$ is $Ar^1$ and $R^1$ is hydrogen, and when X is N $R^1$ is $Ar^1$ and $R^2$ is hydrogen;

$R^3$ is $N(R^6)(R^7)$;

$R^4$ is alkyl or haloalkyl;

$R^5$ is alkyl;

$R^6$ is hydrogen or alkyl;

$R^7$ is hydrogen or alkyl;

or $N(R^6)(R^7)$ taken together is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxy, alkoxy, haloalkoxy, carboxy, or carboxamido;

or $N(R^6)(R^7)$ taken together is indolinyl, isoindolinyl, tetrahydroisoquinolinyl, or decahydroisoquinolinyl, and is substituted with 0-3 substituents selected from halo, alkyl, haloalkyl, hydroxy, alkoxy, haloalkoxy, carboxy, or carboxamido;

or $N(R^6)(R^7)$ taken together is a [4.2.0,], [4.3.0,], [4.4.0,], [4.5.0,], [4.6.0,], [5.2.0,], [5.3.0,], [5.4.0,], [5.5.0,], [5.6.0,], [6.2.0,], [6.3.0,], [6.4.0,], [6.5.0,], [6.6.0,] spirocyclic amine;

or N(R⁶)(R⁷) taken together is

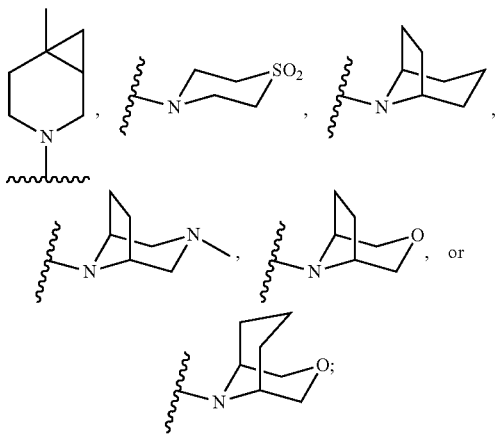

and

Ar¹ is phenyl, pyridinyl, or biphenyl and is substituted with 0-3 substituents selected from halo, alkyl, haloalkyl, cycloalkyl, halocycloalkyl, alkoxy, haloalkoxy, phenyl, benzyl, phenoxy, and benzyloxy wherein said phenyl, benzyl, phenoxy, and benzyloxy is substituted with 0-3 halo, alkyl, haloalkyl, cycloalkyl, halocycloalkyl, alkoxy, and haloalkoxy substituents;

or Ar¹ is tetralinyl, ((methyl)indazolyl)phenyl, or (benzyloxy)phenyl;

or a pharmaceutically acceptable salt thereof.

Another aspect of the invention is a compound of formula I where:

X is C or N;

R¹ is hydrogen or Ar¹;

R² is hydrogen or Ar¹;

provided that when X is C either R¹ is Ar¹ and R² is hydrogen or R² is Ar¹ and R¹ is hydrogen, and when X is N R¹ is Ar¹ and R² is hydrogen;

R³ is N(R⁶)(R⁷);

R⁴ is alkyl or haloalkyl;

R⁵ is alkyl;

R⁶ is hydrogen or alkyl;

R⁷ is hydrogen or alkyl;

or N(R⁶)(R⁷) taken together is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxy, alkoxy, haloalkoxy, carboxy, or carboxamido;

or N(R⁶)(R⁷) taken together is indolinyl, isoindolinyl, tetrahydroisoquinolinyl, or decahydroisoquinolinyl, and is substituted with 0-3 substituents selected from halo, alkyl, haloalkyl, hydroxy, alkoxy, haloalkoxy, carboxy, or carboxamido;

or N(R⁶)(R⁷) taken together is a [4.2.0,], [4.3.0,], [4.4.0,], [4.5.0,], [4.6.0,], [5.2.0,], [5.3.0,], [5.4.0,], [5.5.0,], [5.6.0,], [6.2.0,], [6.3.0,], [6.4.0,], [6.5.0,], [6.6.0,] spirocyclic amine; and Ar¹ is phenyl or biphenyl and is substituted with 0-3 substituents selected from halo, alkyl, haloalkyl, cycloalkyl, and halocycloalkyl;

or Ar¹ is tetralinyl or (benzyloxy)phenyl;

or a pharmaceutically acceptable salt thereof.

Another aspect of the invention is a compound of formula I where:

X is C or N;

R¹ is hydrogen or Ar¹;

R² is hydrogen or Ar¹;

provided that when X is C either R¹ is Ar¹ and R² is hydrogen or R² is Ar¹ and R¹ is hydrogen, and when X is N R¹ is Ar¹ and R² is hydrogen;

R³ is N(R⁶)(R⁷);

R⁴ is alkyl;

R⁵ is alkyl;

N(R⁶)(R⁷) taken together is pyrrolidinyl, piperidinyl, piperazinyl, morpholinyl, homopiperidinyl, or homopiperazinyl, and is substituted with 0-3 substituents selected from halo, alkyl, haloalkyl, hydroxy, alkoxy, haloalkoxy, carboxy, or carboxamido;

or N(R⁶)(R⁷) taken together is indolinyl, isoindolinyl, tetrahydroisoquinolinyl, or decahydroisoquinolinyl;

or N(R⁶)(R⁷) taken together is a [4.4.0,], [5.2.0,], or [5.4.0,] spirocyclic amine; and Ar¹ is phenyl or biphenyl and is substituted with 0-3 substituents selected from halo, alkyl, haloalkyl, cycloalkyl, and halocycloalkyl;

or Ar¹ is tetralinyl or (benzyloxy)phenyl;

or a pharmaceutically acceptable salt thereof.

Another aspect of the invention is a compound of formula I where X is C and R¹ is Ar¹ and R² is hydrogen or R² is Ar¹ and R¹ is hydrogen.

Another aspect of the invention is a compound of formula I where X is C, R¹ is Ar¹, and R² is hydrogen.

Another aspect of the invention is a compound of formula I where X is C, and R² is Ar¹ and R¹ is hydrogen.

Another aspect of the invention is a compound of formula I where X is N, R¹ is Ar¹, and R² is hydrogen.

Another aspect of the invention is a compound of formula I where R⁴ is alkyl.

Another aspect of the invention is a compound of formula I where R⁴ is t-butyl.

Another aspect of the invention is a compound of formula I where R⁵ is methyl.

Another aspect of the invention is a compound of formula I where N(R⁶)(R⁷) taken together is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxy, alkoxy, haloalkoxy, carboxy, or carboxamido.

Another aspect of the invention is a compound of formula I where N(R⁶)(R⁷) taken together is pyrrolidinyl, piperidinyl, piperazinyl, morpholinyl, homopiperidinyl, or homopiperazinyl, and is substituted with 0-3 substituents selected from halo, alkyl, haloalkyl, hydroxy, alkoxy, haloalkoxy, carboxy, or carboxamido.

Another aspect of the invention is a compound of formula I where N(R⁶)(R⁷) taken together is indolinyl, isoindolinyl, tetrahydroisoquinolinyl, or decahydroisoquinolinyl, and is substituted with 0-3 substituents selected from halo, alkyl, haloalkyl, hydroxy, alkoxy, haloalkoxy, carboxy, or carboxamido.

Another aspect of the invention is a compound of formula I where N(R⁶)(R⁷) taken together is a [4.2.0,], [4.3.0,], [4.4.0,], [4.5.0,], [4.6.0,], [5.2.0,], [5.3.0,], [5.4.0,], [5.5.0,], [5.6.0,], [6.2.0,], [6.3.0,], [6.4.0,], [6.5.0,], [6.6.0,] spirocyclic amine Another aspect of the invention is a compound of formula I where $N(R^6)(R^7)$ taken together is

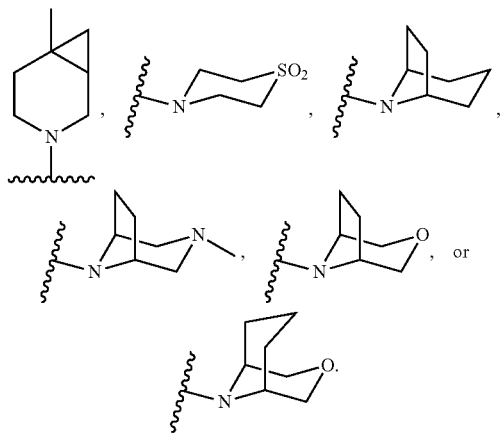

Another aspect of the invention is a compound of formula I where $Ar^1$ is phenyl, pyridinyl, or biphenyl and is substituted with 0-3 substituents selected from halo, alkyl, haloalkyl, cycloalkyl, halocycloalkyl, alkoxy, haloalkoxy, phenyl, benzyl, phenoxy, and benzyloxy wherein said phenyl, benzyl, phenoxy, and benzyloxy is substituted with 0-3 halo, alkyl, haloalkyl, cycloalkyl, halocycloalkyl, alkoxy, and haloalkoxy substituents.

Another aspect of the invention is a compound of formula I where $Ar^1$ is phenyl or biphenyl and is substituted with 0-3 substituents selected from halo, alkyl, haloalkyl, cycloalkyl, and halocycloalkyl.

Another aspect of the invention is a compound of formula I where $Ar^1$ is tetralinyl, ((methyl)indazolyl)phenyl, or (benzyloxy)phenyl.

Another aspect of the invention is a compound of formula I where $Ar^1$ is tetralinyl or (benzyloxy)phenyl.

For a compound of Formula I, the scope of any instance of a variable substituent, including X, $R^1$, $R^2$, $R^3$, $R^4$, $R^5$, $R^6$, $R^7$, and $Ar^1$, can be used independently with the scope of any other instance of a variable substituent. As such, the invention includes combinations of the different aspects.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1. Activity equal to A refers to a compound having an $EC_{50} \leq 100$ nM, while B and C denote compounds having an $EC_{50}$ between 100 nM and 1 uM (B) or >1 uM (C).

TABLE 1

| Example | Activity | $EC_{50}$ μM |
|---|---|---|
| 1 | B | 0.55 |
| 2 | C | 5 |
| 3 | C | |
| 4 | C | |
| 5 | C | |
| 6 | C | |
| 7 | C | 5.2 |
| 8 | B | 0.72 |
| 9 | C | |
| 10 | C | |
| 11 | C | |
| 12 | C | |
| 13 | C | |
| 14 | B | |
| 15 | C | |
| 16 | B | 0.77 |
| 17 | C | |
| 18 | C | |
| 19 | B | |
| 20 | B | |
| 21 | C | |
| 22 | C | |
| 23 | C | |
| 24 | C | |
| 25 | C | |
| 26 | B | 0.3 |
| 27 | C | |
| 28 | B | |
| 29 | B | |
| 30 | B | |
| 31 | A | |
| 32 | A | 0.06 |
| 33 | B | |
| 34 | B | |
| 35 | B | 0.13 |
| 36 | B | |
| 37 | B | 0.24 |
| 38 | C | |
| 39 | B | |
| 40 | C | |
| 41 | A | |
| 42 | A | 0.05 |
| 43 | B | 0.78 |
| 44 | B | |
| 45 | C | 3.14 |
| 46 | B | |
| 47 | B | |
| 48 | C | |
| 49 | B | |
| 50 | C | 3.23 |
| 51 | B | |
| 52 | A | 0.05 |
| 53 | B | |
| 54 | B | |
| 55 | B | |
| 56 | B | |
| 57 | A | |
| 58 | A | |
| 59 | A | 0.015 |
| 60 | A | |
| 61 | B | |
| 62 | B | 0.42 |
| 63 | B | |
| 64 | B | |
| 65 | B | |
| 66 | B | |
| 67 | B | |
| 68 | B | |
| 69 | B | 0.19 |
| 70 | B | |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

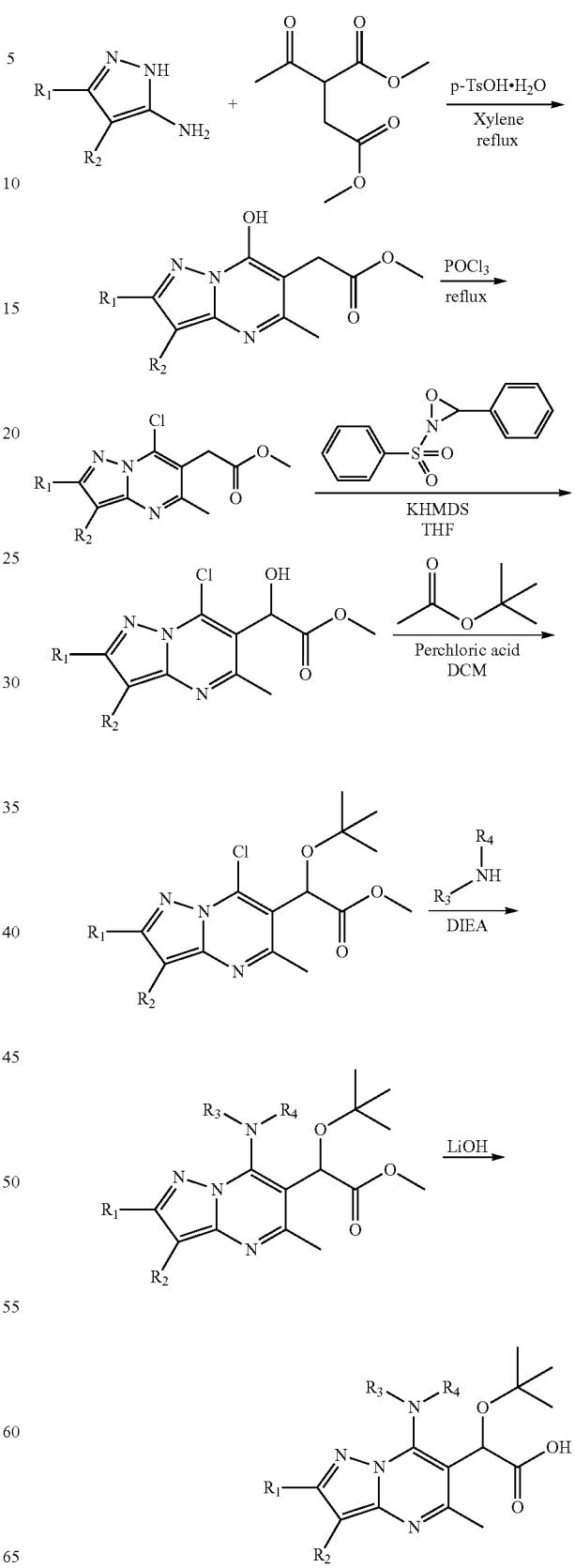

Scheme 1.

13
Scheme 2.
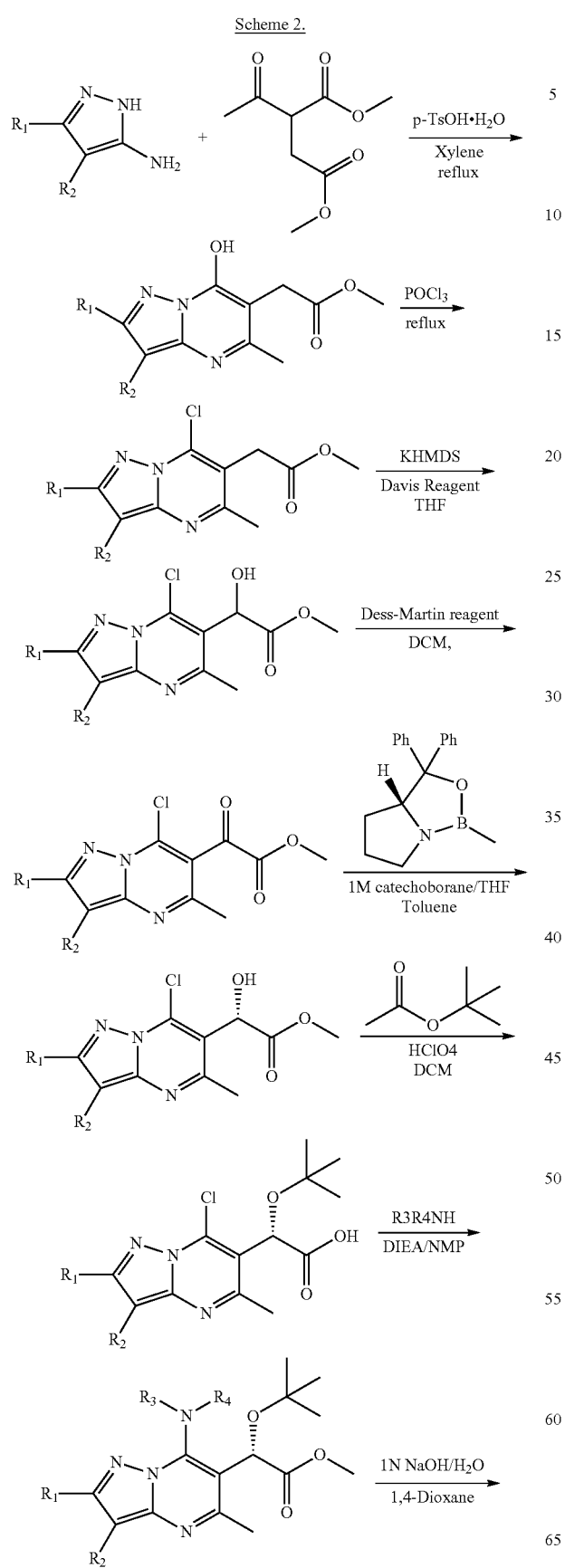
14
-continued
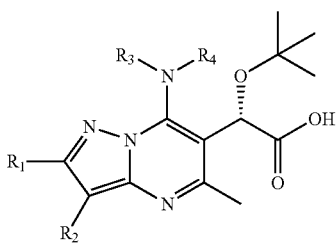
Scheme 3.
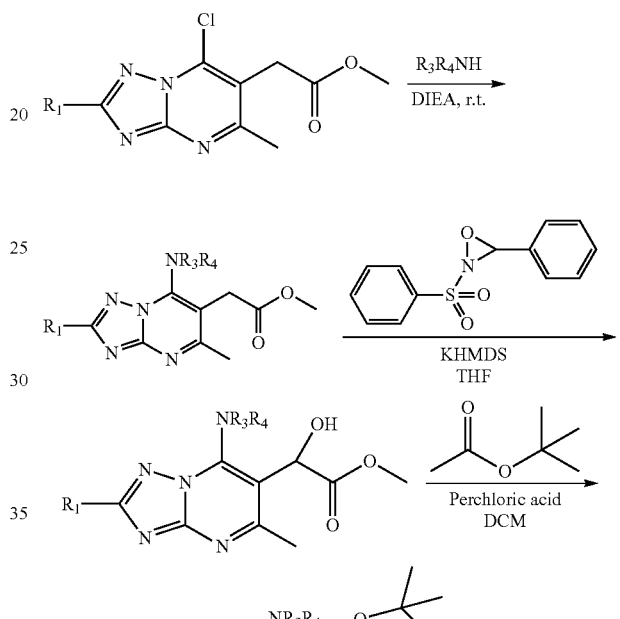
Scheme 4.
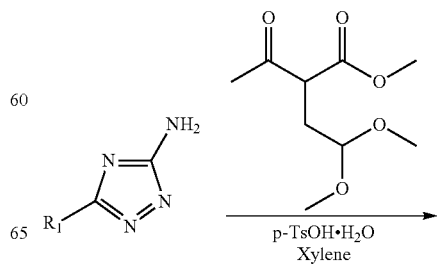

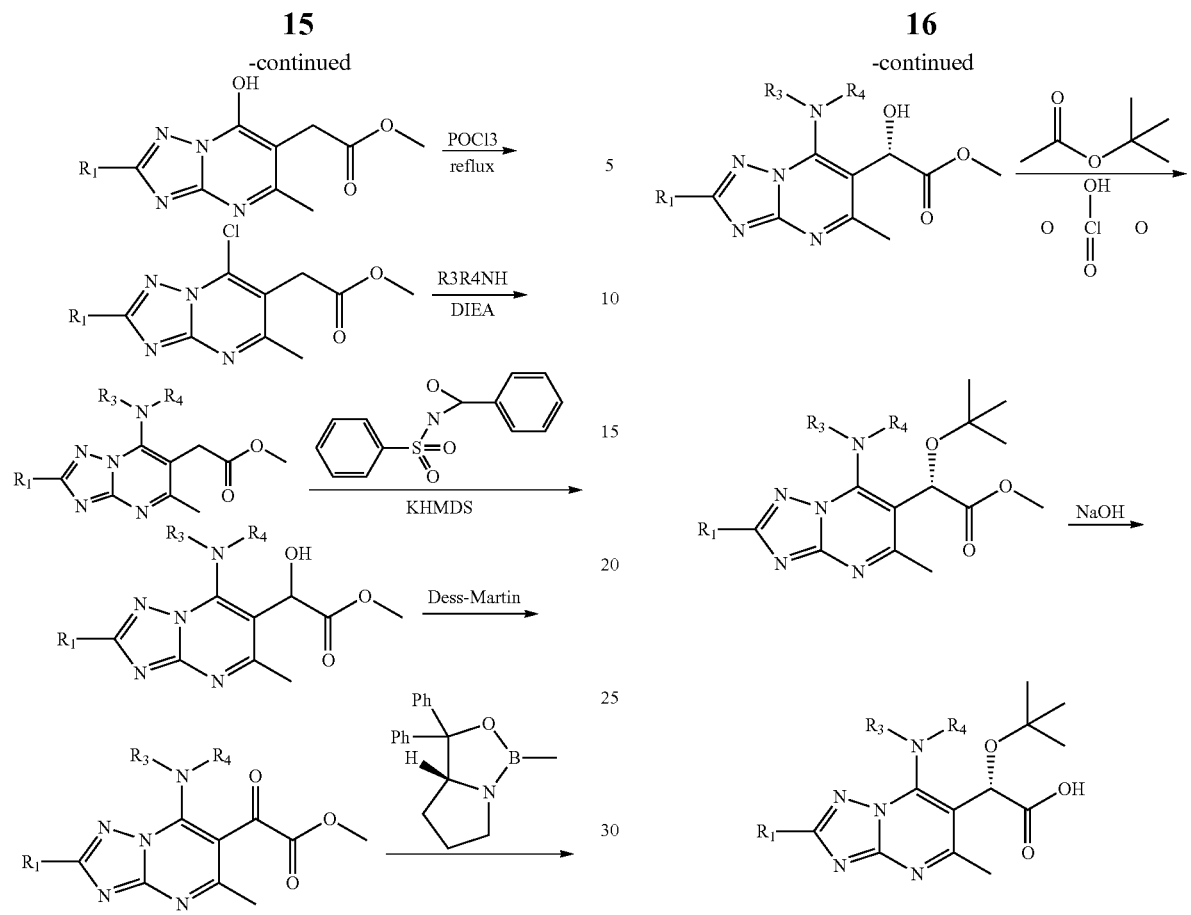
Scheme 5.
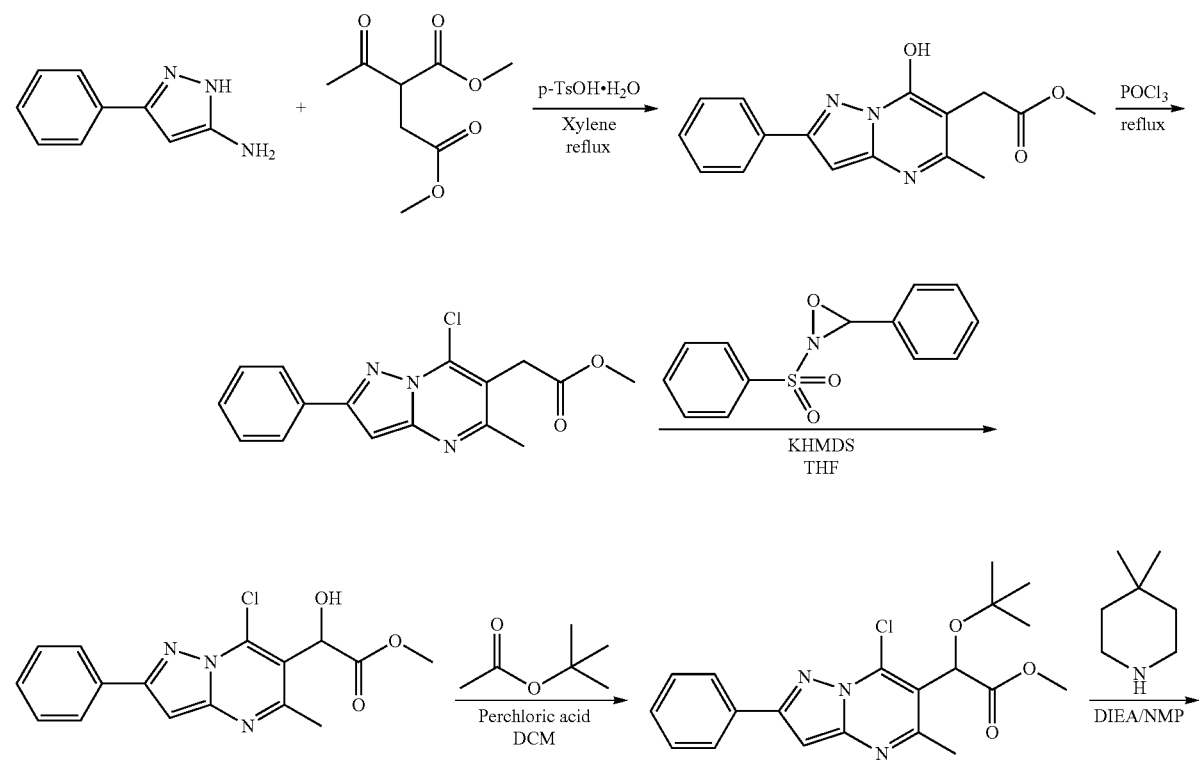

-continued
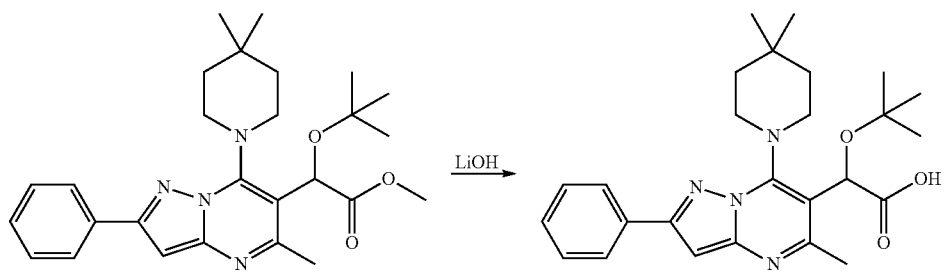
Scheme 6.
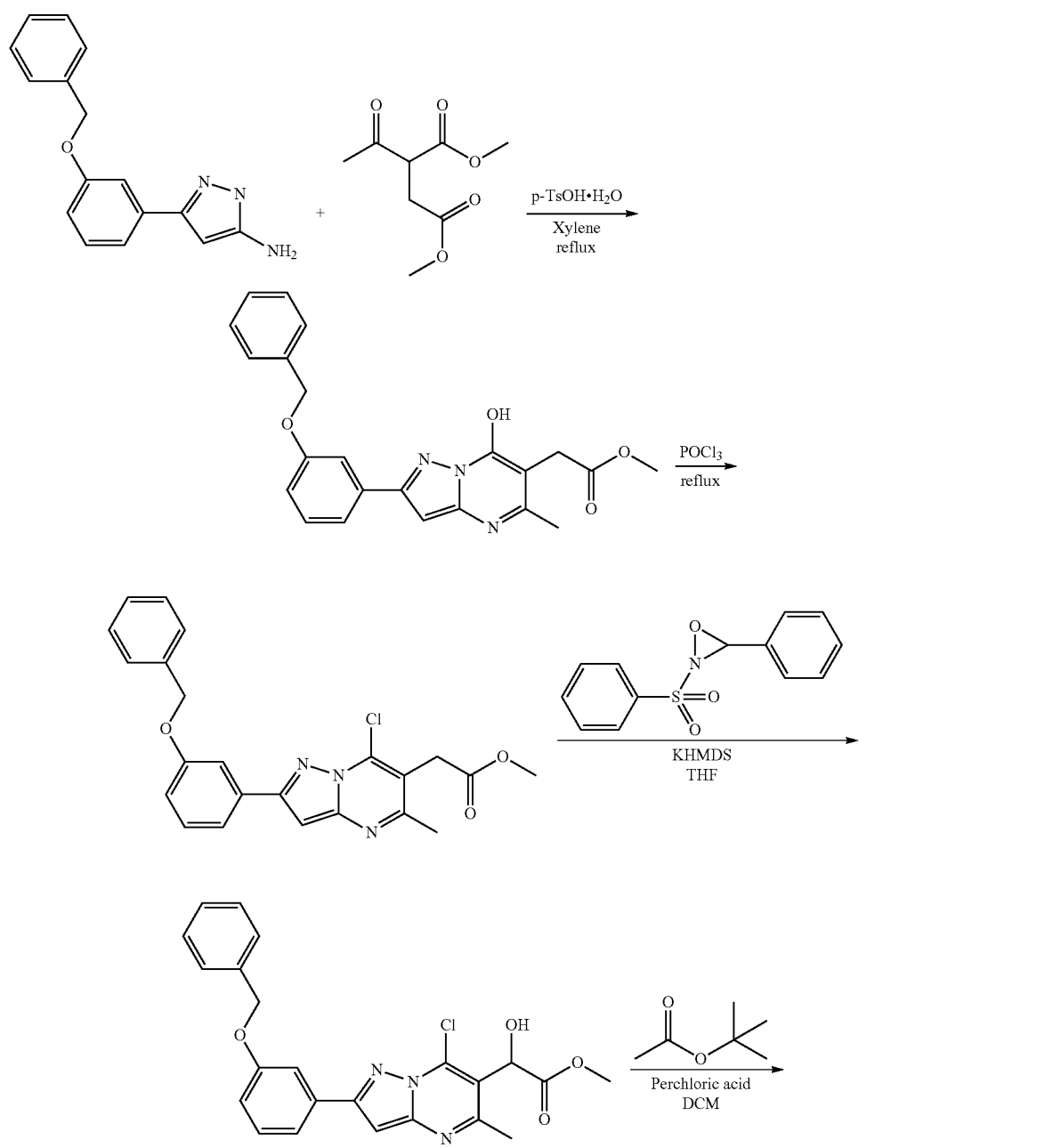

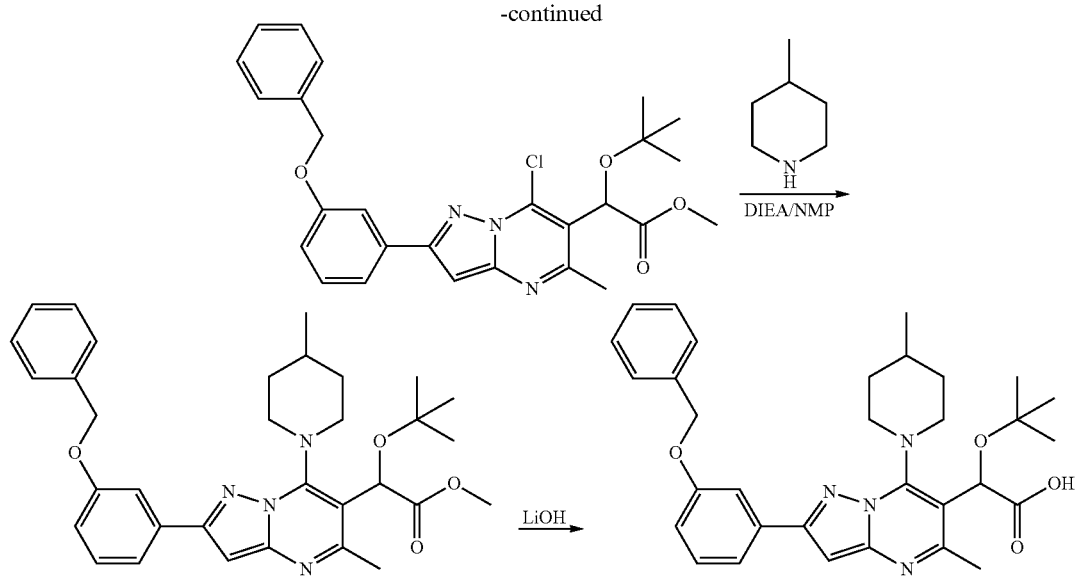
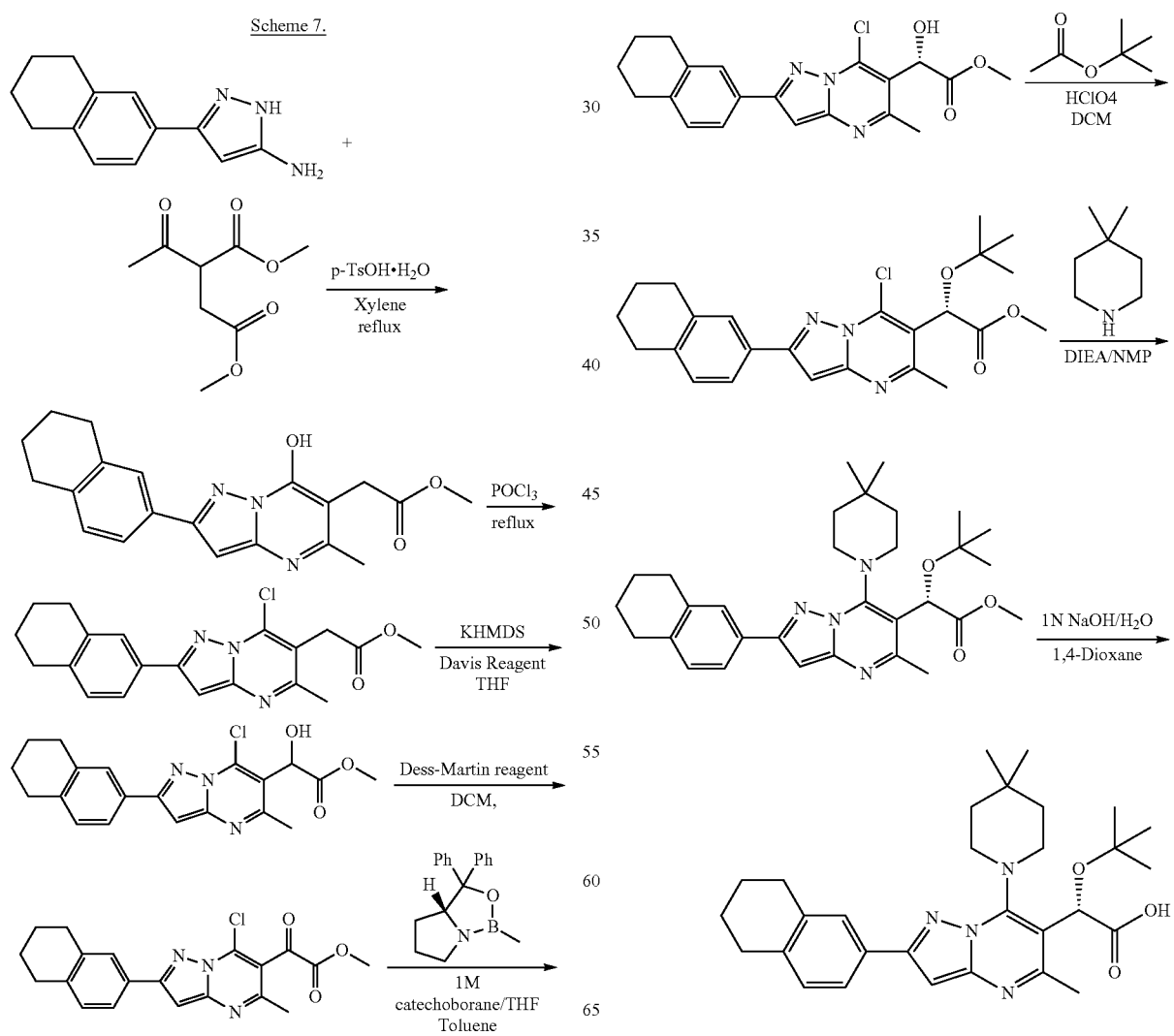
Scheme 7.

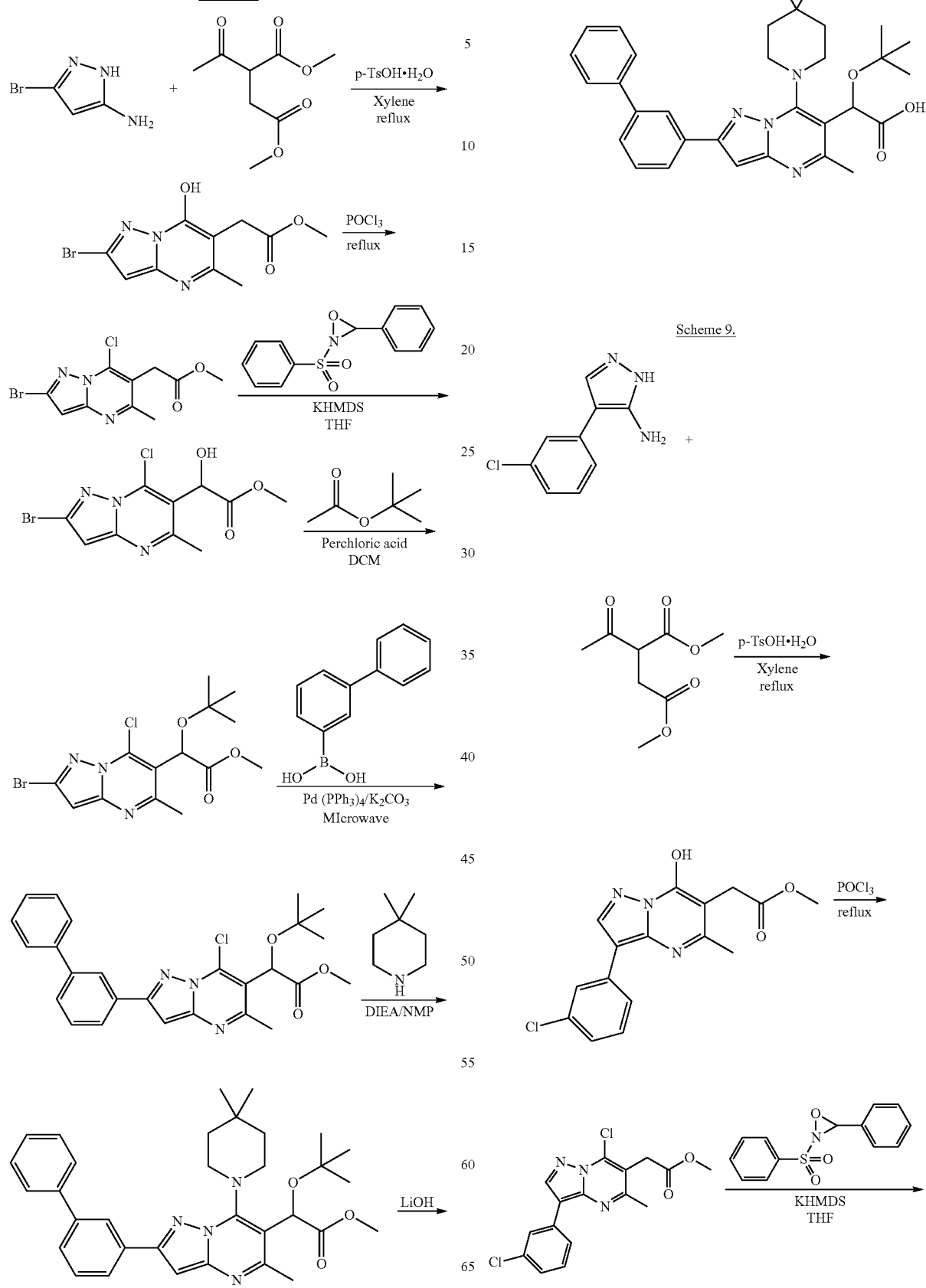

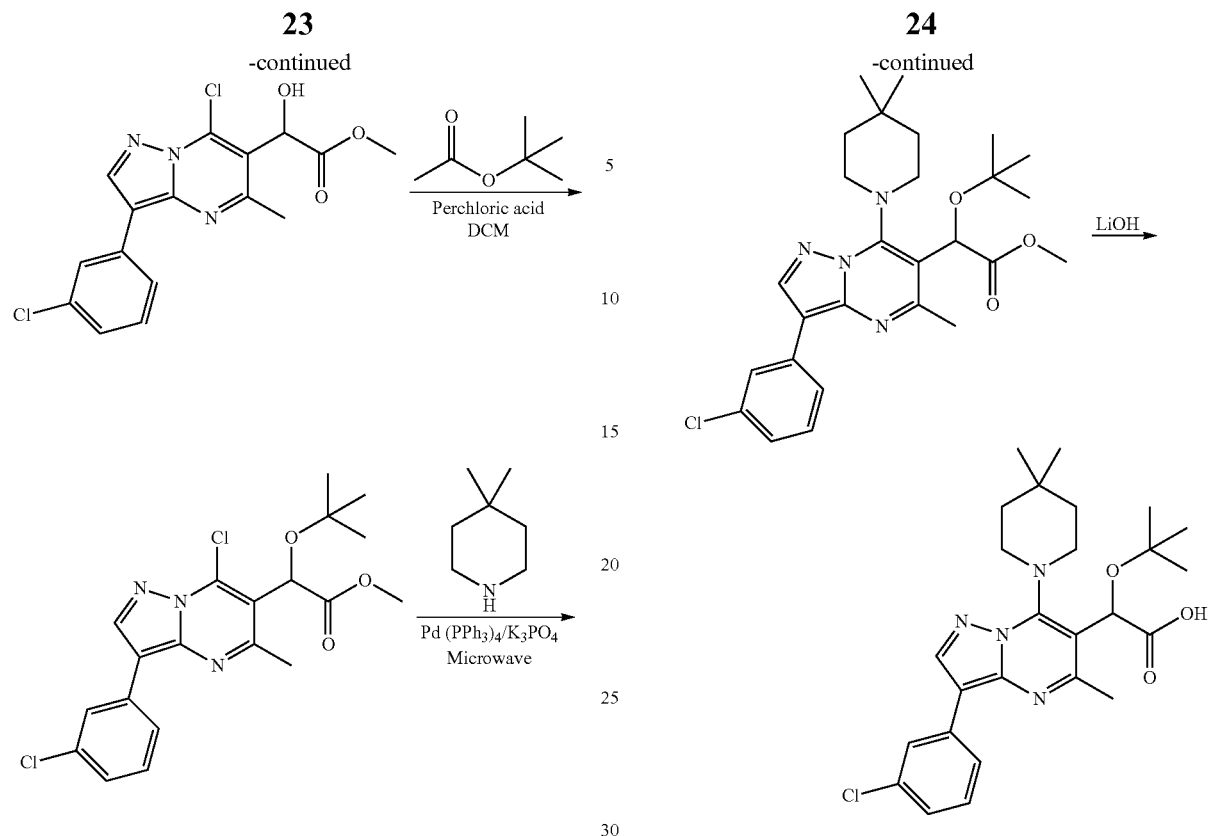
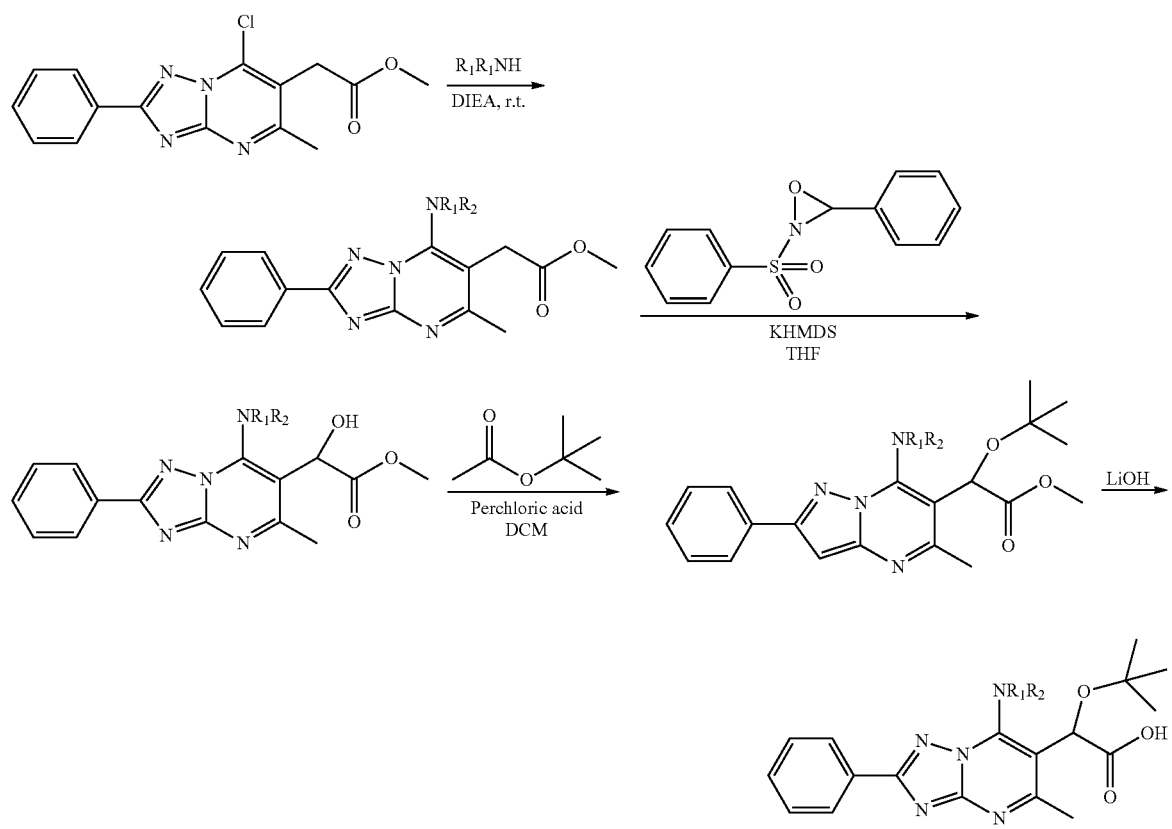
Scheme 10.

Scheme 11.
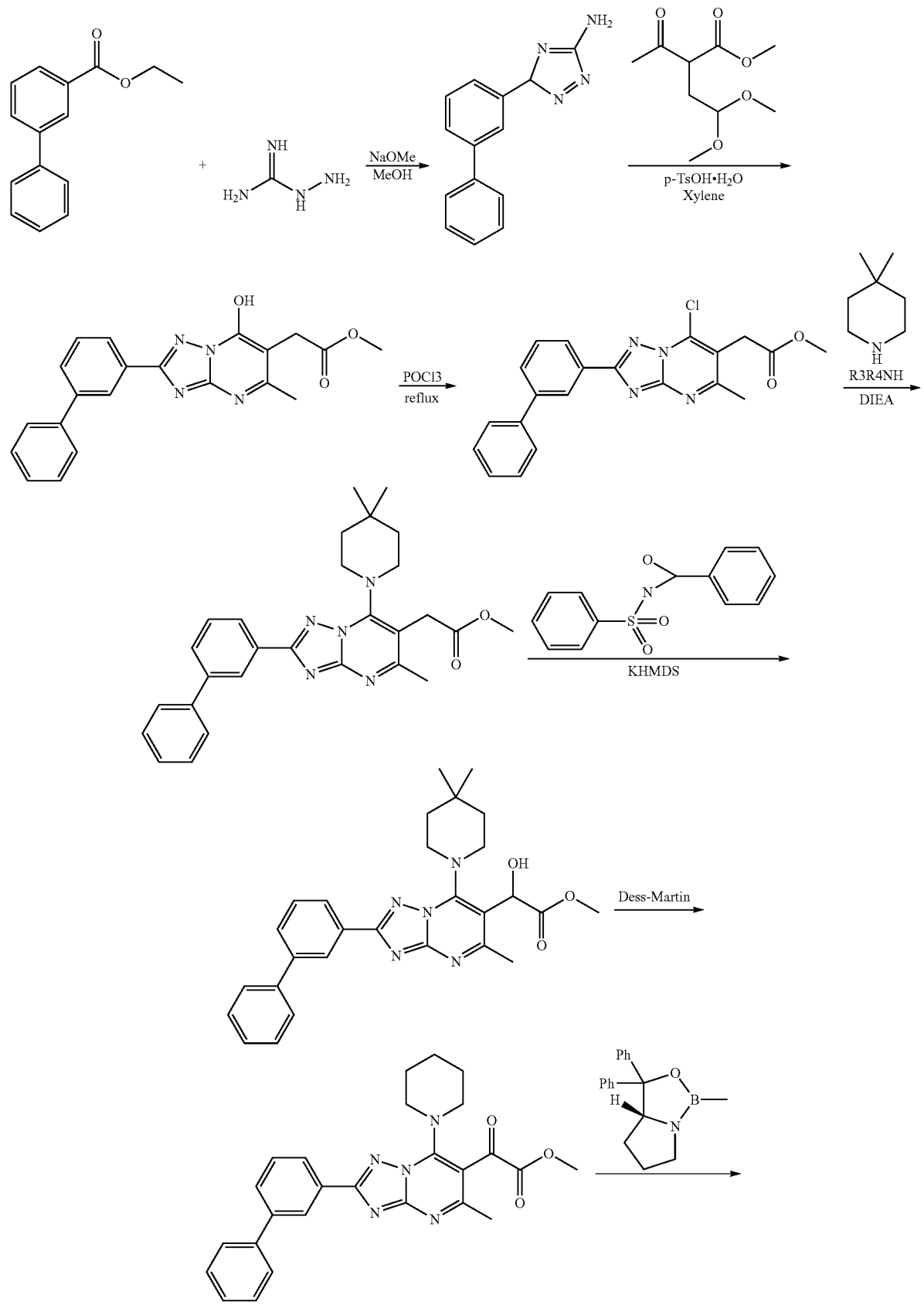

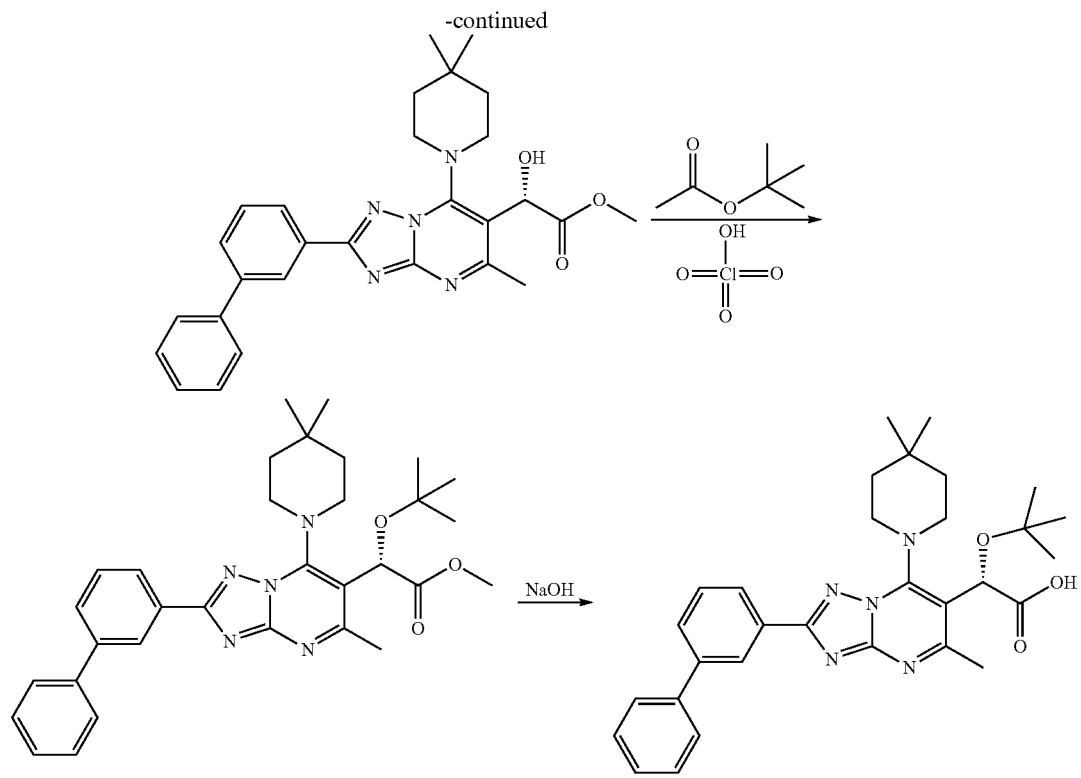

DESCRIPTION OF SPECIFIC EMBODIMENTS

| LC/MS Method A | |
|---|---|
| Column | Waters BEH C18, 2.0 × 50 mm, 1.7-μm particles |
| Flow Rate | 0.5 mL/min |
| Solvent A | 5% methanol-95% H$_2$O - 10 mM NH$_4$OAc |
| Solvent B | 95% methanol-5% H$_2$O - 10 mM NH$_4$OAc |
| Gradient | % B 0-100 |
| Gradient Time | 5 min. |
| Wavelength | 220 nm |
| LC/MS Method B | |
| Column | Waters BEH C18, 2.0 × 50 mm, 1.7-μm particles |
| Flow Rate | 0.5 mL/min |
| Solvent A | 5% Acetonitrile-95% H$_2$O - 10 mM NH$_4$OAc |
| Solvent B | 95% Acetonitrile-5% H$_2$O - 10 mM NH$_4$OAc |
| Gradient | % B 0-100 |
| Gradient Time | 6 min. |
| Wavelength | 220 nm |
| LC/MS Method C | |
| Column | PHENOMENEX-LUNA 2.0 × 30 mm 3 um |
| Flow Rate | 1 mL/min |
| Solvent A | 10% Acetonitrile-90% H$_2$O - 0.1% TFA |
| Solvent B | 90% Acetonitrile-10% H$_2$O - 0.1% TFA |
| Gradient | % B 0-100 |
| Gradient Time | 2 min. |
| Wavelength | 220 nm |

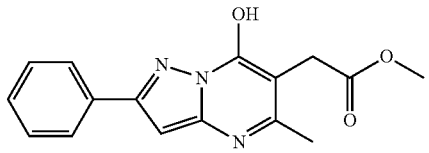 [SMILES: COC(=O)Cc1c(C)nc2cc(-c3ccccc3)nn2c1O]

Methyl 2-(5-methyl-7-oxo-2-phenyl-4,7-dihydropyrazolo[1,5-a]pyrimidin-6-yl)acetate To a solution of 3-phenyl-1H-pyrazol-5-amine (4 g, 25.1 mmol) and dimethyl 2-acetylsuccinate (12 mL, 74.0 mmol) in xylene (120 mL) was added p-toluenesulfonic acid monohydrate (50 mg, 0.263 mmol). The reaction mixture was heated at reflux under a Dean-Stark trap for 20 h. The solid was filtered and washed with hexanes to afford the title compound (6.4 g, 86%). $^1$H-NMR (400 MHz, MeOD) δ 2.37 (3 H, s), 3.66 (2 H, s), 3.72 (3 H, s), 6.46 (1 H, s), 7.34-7.53 (3 H, m), 7.87-8.06 (2 H, m).

| Methyl 2-(5-methyl-7-oxo-2-phenyl-4,7-dihydropyrazolo[1,5-a]pyrimidin-6-yl)acetate | |
|---|---|
| MS (M + H)$^+$ Calcd. | 298 |
| MS (M + H)$^+$ Observ. | 298 |
| Retention Time | 1.15 min |
| LC Condition | |
| Solvent A | 10% Acetonitrile: 90% Water: 0.1% TFA |
| Solvent B | 90% Acetonitrile: 10% Water: 0.1% TFA |
| Start % B | 0 |
| Final % B | 100 |

-continued

| Methyl 2-(5-methyl-7-oxo-2-phenyl-4,7-dihydropyrazolo[1,5-a]pyrimidin-6-yl)acetate | |
|---|---|
| Gradient Time | 2 min |
| Flow Rate | 1 mL/min |
| Wavelength | 220 |
| Solvent Pair | Acetonitrile:Water:TFA |
| Column | Phenomenex Luna C18, 30 × 2, 3u |

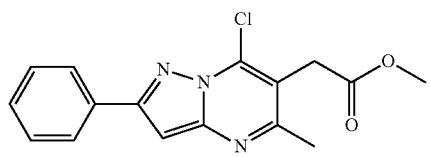 [SMILES: COC(=O)Cc1c(C)nc2cc(-c3ccccc3)nn2c1Cl]

Methyl 2-(7-chloro-5-methyl-2-phenylpyrazolo[1,5-a]pyrimidin-6-yl)acetate

To methyl 2-(5-methyl-7-oxo-2-phenyl-4,7-dihydropyrazolo[1,5-a]pyrimidin-6-yl)acetate (3 g, 10.09 mmol) was added POCl$_3$ (25 mL, 268 mmol). The reaction mixture was heated at reflux for 1 h. After cooling, the reaction mixture was added drop-wise to ice-water. A brown solid precipitated. The solid was filtered and washed with water, then dissolved in ethyl acetate. The organic solution was washed with saturated NaHCO$_3$ and dried over sodium sulfate. The solvent was evaporated to give the title compound (2.77 g, 84%). $^1$H-NMR (400 MHz, DMSO-d$_6$) δ 2.58 (3H, s), 3.71 (3 H, s), 4.04 (2 H, s), 7.29 (1 H, s), 7.43-7.58 (3 H, m), 8.07 (2 H, d, J=7.0 Hz).

| Methyl 2-(7-chloro-5-methyl-2-phenylpyrazolo[1,5-a]pyrimidin-6-yl)acetate | |
|---|---|
| MS (M + H)$^+$ Calcd. | 316 |
| MS (M + H)$^+$ Observ. | 316 |
| Retention Time | 2.09 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

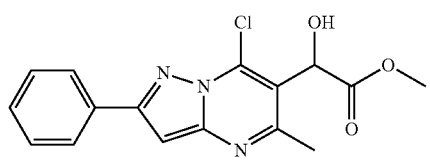 [SMILES: COC(=O)C(O)c1c(C)nc2cc(-c3ccccc3)nn2c1Cl]

Methyl 2-(7-chloro-5-methyl-2-phenylpyrazolo[1,5-a]pyrimidin-6-yl)-2-hydroxyacetate To a stirred solution of KHMDS (0.5 M in toluene, 9.50 mL, 4.75 mmol) in THF (24 mL) at −78° C. was added a solution of methyl 2-(7-chloro-5-methyl-2-phenylpyrazolo[1,5-a]pyrimidin-6-yl)acetate (1 g, 3.17 mmol) in THF (24 mL) drop wise over 40 min. The mixture was stirred at −78° C. for 30 min. A solution of 3-phenyl-2-(phenylsulfonyl)-1,2-oxaziridine (1.241 g, 4.75 mmol) in THF (24 mL) was added over 20 min and the reaction mixture was stirred for additional 30 min at −78° C. The reaction mixture was quenched with saturated NH$_4$Cl aqueous solution (4 mL). The reaction mixture was allowed to warm to room temperature and then diluted with ethyl acetate (100 mL). The organic phase was washed with water and brine and dried with sodium sulfate. The solvent was evaporated. Purification by silica gel chromatography provided the title compound (535 mg, 50.9%). $^1$H-NMR (500 MHz, CDCl$_3$) δ 2.62 (3 H, s), 3.83 (3 H, s), 5.29 (1 H, s), 5.76 (1 H, s), 6.94 (1 H, s), 7.38-7.50 (3 H, m), 8.00-8.02 (2 H, m).

| Methyl 2-(7-chloro-5-methyl-2-phenylpyrazolo[1,5-a]pyrimidin-6-yl)-2-hydroxyacetate | |
|---|---|
| MS (M + H)$^+$ Calcd. | 332 |
| MS (M + H)$^+$ Observ. | 332 |
| Retention Time | 2.03 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

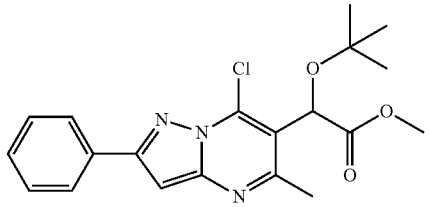 [SMILES: COC(=O)C(OC(C)(C)C)c1c(C)nc2cc(-c3ccccc3)nn2c1Cl]

Methyl 2-tert-butoxy-2-(7-chloro-5-methyl-2-phenylpyrazolo[1,5-a]pyrimidin-6-yl)acetate To a suspension of methyl 2-(7-chloro-5-methyl-2-phenylpyrazolo[1,5-a]pyrimidin-6-yl)-2-hydroxyacetate (100 mg, 0.301 mmol) in tert-butyl acetate (2 mL) at room temperature was added CH$_2$Cl$_2$ (2 mL) followed by perchloric acid (0.027 mL, 0.452 mmol). The reaction mixture was stirred for 2 h at room temperature. The reaction mixture was quenched with water and diluted with ethyl acetate. The organic phase was washed with saturated NaHCO$_3$ and dried over sodium sulfate. The solvent was evaporated. Purification by silica gel chromatography provided the title compound (71 mg, 60.7%). $^1$H-NMR (500 MHz, CDCl$_3$) δ 1.27 (9 H, s), 2.66 (3 H, s), 3.73 (3 H, s), 5.66 (1 H, s), 6.93 (1 H, s), 7.34-7.52 (3 H, m), 8.01 (2 H, d, J=7.3 Hz).

| Methyl 2-tert-butoxy-2-(7-chloro-5-methyl-2-phenylpyrazolo[1,5-a]pyrimidin-6-yl)acetate | |
|---|---|
| MS (M + H)+ Calcd. | 388 |
| MS (M + H)+ Observ. | 388 |
| Retention Time | 2.42 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

EXAMPLE 1

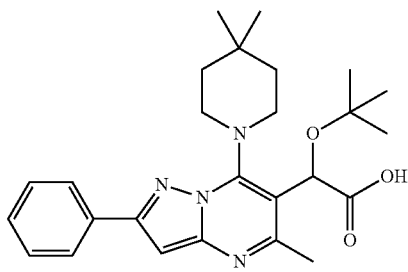 [SMILES: Cc1nc2cc(-c3ccccc3)nn2c(N2CCC(C)(C)CC2)c1C(OC(C)(C)C)C(=O)O]

2-(tert-butoxy)-2-(7-(4,4-dimethylpiperidin-1-yl)-5-methyl-2-phenylpyrazolo[1,5a]pyrimidin-6-yl)acetic acid To a solution of Methyl 2-tert-butoxy-2-(7-chloro-5-methyl-2-phenylpyrazolo[1,5-a]pyrimidin-6-yl)acetate (40 mg, 0.091 mmol) and 4,4-dimethylpiperidine.HCl (13.55 mg, 0.091 mmol) in NMP (1 mL) was added DIEA (0.047 mL, 0.272 mmol) and the mixture was heated at 50° C. for 2 h. Then, 1N LiOH (0.272 mL, 0.272 mmol) was added to the reaction mixture and the contents were heated at 50° C. for 2 h. The reaction mixture was then filtered and purified by prep-HPLC to afford 2-(tert-butoxy)-2-(7-(4,4-dimethylpiperidin-1-yl)-5-methyl-2-phenylpyrazolo[1,5a]pyrimidin-6-yl)acetic acid (13.5 mg, 0.027 mmol, 29.6% yield) as white solid. $^1$H NMR (500 MHz, DMSO-$d_6$) δ 1.21 (9H, s), 1.58-1.93 (10 H, m), 2.52 (3 H, s), 5.70-5.83 (1 H, m), 7.03 (1 H, s), 7.34-7.58 (3 H, m), 7.90-8.10 (2 H, m).

| Methyl 2-tert-butoxy-2-(7-chloro-5-methyl-2-phenylpyrazolo[1,5-a]pyrimidin-6-yl)acetate | |
|---|---|
| MS (M + H)+ Calcd. | 451 |
| MS (M + H)+ Observ. | 451 |
| Retention Time | 4.36 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

Examples 2-25 were synthesized using the procedure described above using the appropriate cyclic amines.

EXAMPLE 2

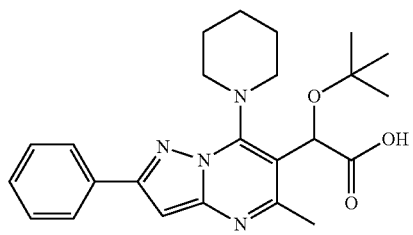 [SMILES: Cc1nc2cc(-c3ccccc3)nn2c(N2CCCCC2)c1C(OC(C)(C)C)C(=O)O]

2-(tert-butoxy)-2-(7-(lpiperidin-1-yl)-5-methyl-2-phenylpyrazolo[1,5a]pyrimidin-6-yl)acetic acid $^1$H NMR (500 MHz, DMSO-$d_6$) δ 1.21 (9H, s), 1.58-1.93 (10 H, m), 2.52 (3 H, s), 5.70-5.83 (1 H, m), 7.03 (1 H, s), 7.34-7.58 (3 H, m), 7.90-8.10 (2 H, m).

| 2-(tert-butoxy)-2-(7-(lpiperidin-1-yl)-5-methyl-2-phenylpyrazolo[1,5a]pyrimidin-6-yl)acetic acid | |
|---|---|
| MS (M + H)+ Calcd. | 423 |
| MS (M + H)+ Observ. | 423 |
| Retention Time | 4.36 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 3

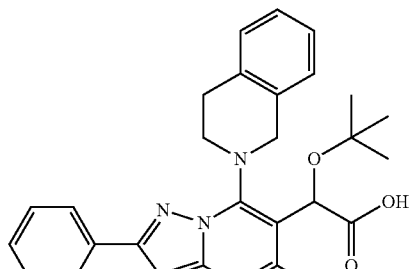

2-(tert-butoxy)-2-(7-(3,4-dijydroisoquinolin-2(1H)-yl)-5-methyl-2-phenylpyrazolo[1,5a]pyrimidin-6-yl)acetic acid $^1$H NMR (500 MHz, DMSO-d$_6$) δ 1.11 (9 H, s), 1.24 (2 H, s), 2.56 (3 H, s), 2.97-3.16 (4 H, m), 5.78 (1 H, s), 7.09 (2 H, s), 7.17-7.32 (3 H, m), 7.35-7.50 (3 H, m), 7.97 (2 H, br. s.).

| 2-(tert-butoxy)-2-(7-(3,4-dijydroisoquinolin-2(1H)-yl)-5-methyl-phenylpyrazolo[1,5a]pyrimidin-6-yl)acetic acid | |
|---|---|
| MS (M + H)$^+$ Calcd. | 471 |
| MS (M + H)$^+$ Observ. | 471 |
| Retention Time | 4.45 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 4

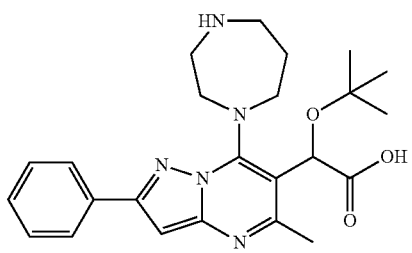 [SMILES: Cc1nc2cc(-c3ccccc3)nn2c(N2CCCNCC2)c1C(OC(C)(C)C)C(=O)O]

2(7-(1,4-diazepan-1-yl)-5-methyl-2-phenylpyrazolo[1,5a]pyrimidin-6-yl)-2-(tert-butoxy)-acetic acid $^1$H NMR (500 MHz, DMSO-d$_6$) δ 1.10-1.30 (9 H, m), 1.71-1.90 (1 H, m), 2.15-2.38 (1 H, m), 2.91 (2 H, s), 2.96-3.19 (4 H, m), 3.58-3.87 (4 H, m), 4.75-4.98 (1 H, m), 7.05 (1 H, s), 7.33-7.57 (3 H, m), 7.89-8.10 (2 H, m).

| 2(7-(1,4-diazepan-1-yl)-5-methyl-2-phenylpyrazolo[1,5a]pyrimidin-6-yl)-2-(tert-butoxy)-acetic acid | |
|---|---|
| MS (M + H)$^+$ Calcd. | 438 |
| MS (M + H)$^+$ Observ. | 438 |
| Retention Time | 3.68 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 5

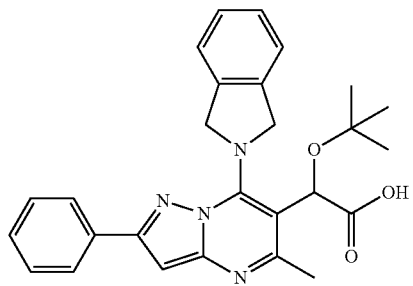 [SMILES: Cc1nc2cc(-c3ccccc3)nn2c(N2Cc3ccccc3C2)c1C(OC(C)(C)C)C(=O)O]

2-(tert-butoxy)-2-(7-(isoindolin-2-yl)-5-methyl-2-phenylpyrazolo[1,5a]pyrimidin-6-yl)acetic acid $^1$H NMR (500 MHz, DMSO-d$_6$) δ 1.19 (9 H, s), 2.60 (3 H, s), 4.62 (2 H, s), 5.31 (2 H, s), 5.88 (1 H, s), 7.13 (1 H, s), 7.30-7.39 (4 H, m), 7.40-7.50 (4 H, m), 7.76-7.91 (2 H, m), 7.97 (1 H, s).

| 2-(tert-butoxy)-2-(7-(isoindolin-2-yl)-5-methyl-2-phenylpyrazolo[1,5a]pyrimidin-6-yl)acetic acid | |
|---|---|
| MS (M + H)$^+$ Calcd. | 457 |
| MS (M + H)$^+$ Observ. | 457 |
| Retention Time | 4.36 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 6

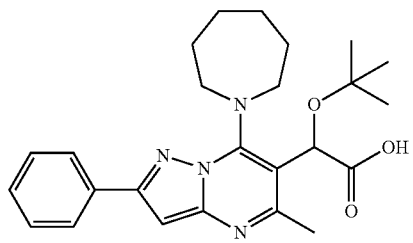 [SMILES: Cc1nc2cc(-c3ccccc3)nn2c(N2CCCCCC2)c1C(OC(C)(C)C)C(=O)O]

2(7-(azepan-1-yl)-5-methyl-2-phenylpyrazolo[1,5a]pyrimidin-6-yl)-2-(tert-butoxy)-acetic acid $^1$H NMR (500 MHz, DMSO-d$_6$) δ 1.22 (9 H, s), 1.79 (6 H, br. s.), 1.90 (2 H, br. s.), 2.55 (3 H, s), 5.88 (1 H, s), 7.06 (1 H, s), 7.40-7.45 (1 H, m), 7.48-7.54 (2 H, m), 8.05 (3 H, d), 7.95-7.98 (1 H, m).

| 2(7-(azepan-1-yl)-5-methyl-2-phenylpyrazolo[1,5a]pyrimidin-6-yl)-2-(tert-butoxy)-acetic acid | |
|---|---|
| MS (M + H)$^+$ Calcd. | 437 |
| MS (M + H)$^+$ Observ. | 437 |
| Retention Time | 4.49 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 7

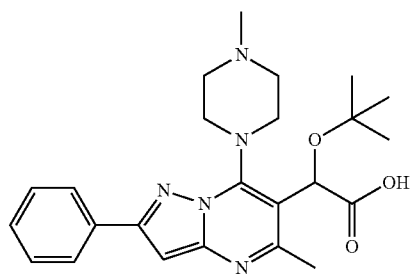 [SMILES: Cc1nc2cc(-c3ccccc3)nn2c(N2CCN(C)CC2)c1C(OC(C)(C)C)C(=O)O]

2-(tert-butoxy)-2-(5-methyl-7(4-methylpiperazin-1-yl)-2-phenylpyrazolo[1,5a]pyrimidin-6-yl)acetic acid $^1$H NMR (500 MHz, DMSO-d$_6$) δ 1.21 (9 H, s), 2.32 (3 H, s), 3.11-3.72 (8 H, m), 5.76-5.79 (1 H, m), 7.05 (1 H, s), 7.37-7.57 (3 H, m), 7.90-8.11 (2 H, m).

| 2-(tert-butoxy)-2-(5-methyl-7(4-methylpiperazin-1-yl)-2-phenylpyrazolo[1,5a]pyrimidin-6-yl)acetic acid | |
|---|---|
| MS (M + H)$^+$ Calcd. | 438 |
| MS (M + H)$^+$ Observ. | 438 |
| Retention Time | 3.70 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 8

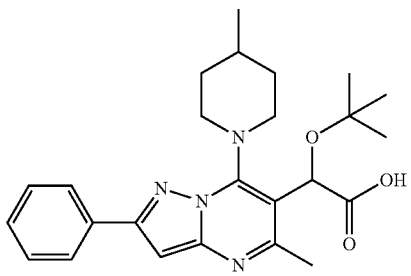 [SMILES: Cc1nc2cc(-c3ccccc3)nn2c(N2CCC(C)CC2)c1C(OC(C)(C)C)C(=O)O]

2-(tert-butoxy)-2-(5-methyl-7-(4-methylpiperidin-1-yl)-2-phenylpyrazolo[1,5a]pyrimidin-6-yl)acetic acid $^1$H NMR (500 MHz, DMSO-d$_6$) δ ppm 1.04 (3 H, s), 1.2 (9H, s), 1.30 (2H, m), 1.79 (4 H, m.), 4.2-4.6 (1 H, m), 5.63-5.87 (1 H, m), 7.02 (1 H, s), 7.37-7.48 (1 H, m), 7.48-7.58 (2 H, m), 7.98-8.09 (2 H, m).

| 2-(tert-butoxy)-2-(5-methyl-7-(4-methylpiperidin-1-yl)-2-phenylpyrazolo[1,5a]pyrimidin-6-yl)acetic acid | |
|---|---|
| MS (M + H)$^+$ Calcd. | 437 |
| MS (M + H)$^+$ Observ. | 437 |
| Retention Time | 4.47 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

Compounds in the Table 2 (Examples 9-25) were synthesized using the procedure described above using the appropriate cyclic amines

TABLE 2

| Example | Structure | RT (min) | HPLC method | MS (M + H)$^+$ Calcd. | Observed mass |
|---|---|---|---|---|---|
| 9 | 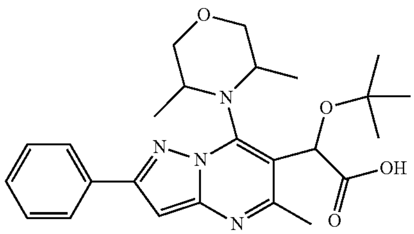 [SMILES: Cc1nc2cc(-c3ccccc3)nn2c(N2C(C)COCC2C)c1C(OC(C)(C)C)C(=O)O] | 4.16 | A | 453 | 453 |
| 10 | 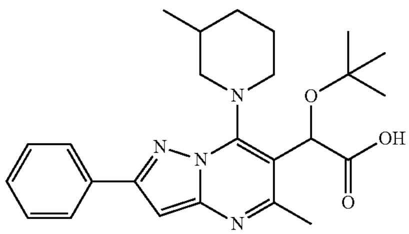 [SMILES: Cc1nc2cc(-c3ccccc3)nn2c(N2CCCC(C)C2)c1C(OC(C)(C)C)C(=O)O] | 4.52 | A | 437 | 437 |
| 11 | 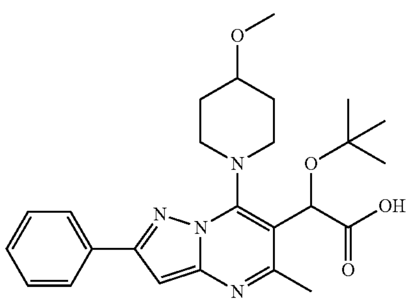 [SMILES: COC1CCN(c2c(C(OC(C)(C)C)C(=O)O)c(C)nc3cc(-c4ccccc4)nn23)CC1] | 4.15 | A | 453 | 453 |
| 12 | 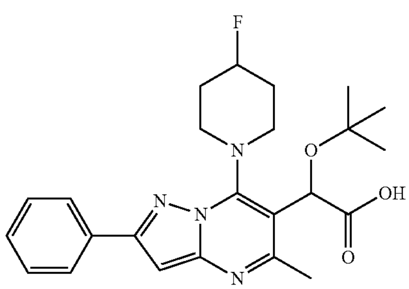 [SMILES: Cc1nc2cc(-c3ccccc3)nn2c(N2CCC(F)CC2)c1C(OC(C)(C)C)C(=O)O] | 4.21 | A | 441 | 441 |
| 13 | 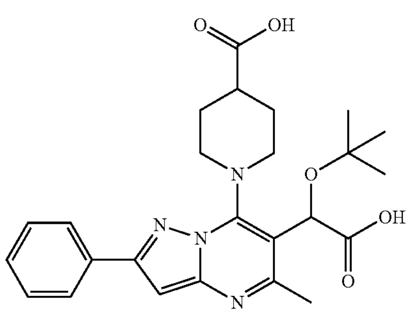 [SMILES: Cc1nc2cc(-c3ccccc3)nn2c(N2CCC(C(=O)O)CC2)c1C(OC(C)(C)C)C(=O)O] | 3.54 | A | 467 | 467 |

TABLE 2-continued
| Example | Structure | RT (min) | HPLC method | MS (M + H)+ Calcd. | Observed mass |
|---|---|---|---|---|---|
| 14 | 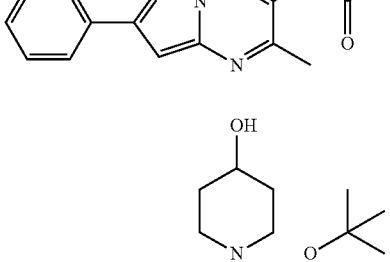 | 4.72 | A | 477 | 477 |
| 15 | 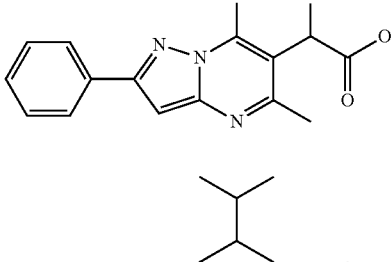 | 3.8 | A | 439 | 439 |
| 16 | 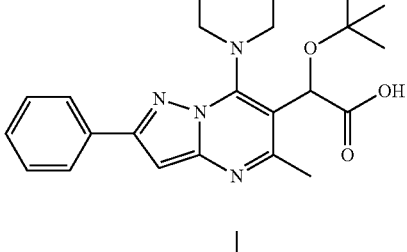 | 4.71 | A | 465 | 465 |
| 17 | 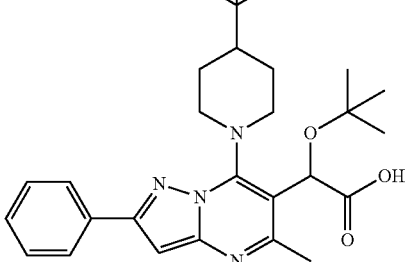 | 4.77 | A | 479 | 479 |
| 18 | 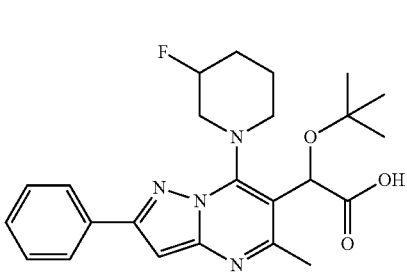 [SMILES: Cc1nc2cc(-c3ccccc3)nn2c(N2CCCC(F)C2)c1C(OC(C)(C)C)C(=O)O] | 4.24 | A | 441 | 441 |

TABLE 2-continued

| Example | Structure | RT (min) | HPLC method | MS (M + H)+ Calcd. | Observed mass |
|---------|-----------|----------|-------------|--------------------|---------------|
| 19 | 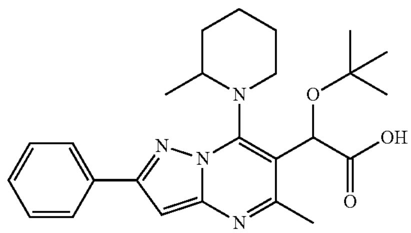 [SMILES: Cc1nc2cc(-c3ccccc3)nn2c(N2CCCCC2C)c1C(OC(C)(C)C)C(=O)O] | 4.5 | A | 437 | 437 |
| 20 | 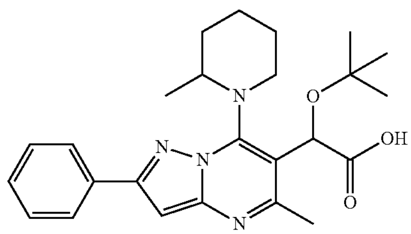 [SMILES: Cc1nc2cc(-c3ccccc3)nn2c(N2CCCCC2C)c1C(OC(C)(C)C)C(=O)O] | 4.55 | A | 437 | 437 |
| 21 | 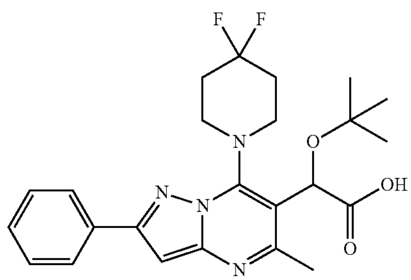 [SMILES: Cc1nc2cc(-c3ccccc3)nn2c(N2CCC(F)(F)CC2)c1C(OC(C)(C)C)C(=O)O] | 4.28 | A | 459 | 459 |
| 22 | 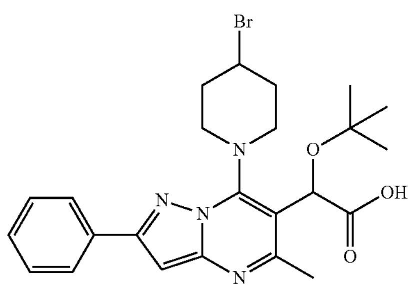 [SMILES: Cc1nc2cc(-c3ccccc3)nn2c(N2CCC(Br)CC2)c1C(OC(C)(C)C)C(=O)O] | 4.43 | A | 503 | 503 |
| 23 | 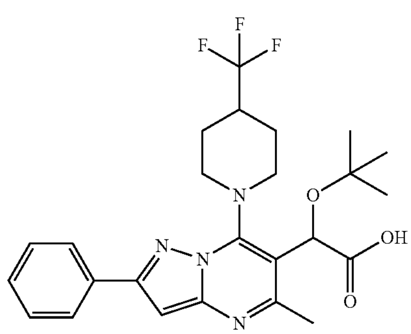 [SMILES: Cc1nc2cc(-c3ccccc3)nn2c(N2CCC(C(F)(F)F)CC2)c1C(OC(C)(C)C)C(=O)O] | 4.48 | A | 491 | 491 |

TABLE 2-continued

| Example | Structure | RT (min) | HPLC method | MS (M + H)+ Calcd. | Observed mass |
|---|---|---|---|---|---|
| 24 | 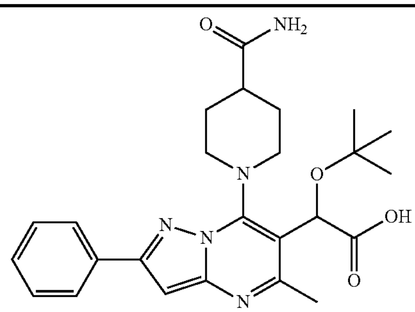 | 3.71 | A | 466 | 466 |
| 25 | 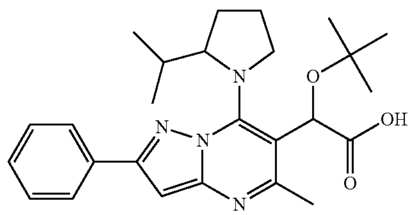 [SMILES: Cc1nc2cc(-c3ccccc3)nn2c(N2CCCC2C(C)C)c1C(OC(C)(C)C)C(=O)O] | 4.5 | A | 451 | 451 |

Examples 26-30 were prepared in a similar fashion to example 1 starting from (S)-methyl 2-(tert-butoxy)-2-(7-chloro-5-methyl-2-phenylpyrazolo[1,5-a]pyrimidin-6-yl)acetate.

EXAMPLE 26

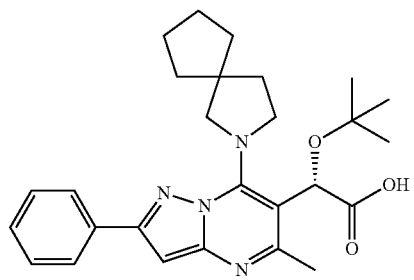 [SMILES: Cc1nc2cc(-c3ccccc3)nn2c(N2CCC3(CCCC3)C2)c1[C@H](OC(C)(C)C)C(=O)O]

(S)-2-(tert-butoxy)-2-(5-methyl-2-phenyl-7-(2-azaspiro[4.4]nonan-2-yl)pyrazolo[1,5-a]pyrimidin-6-yl) acetic acid (S)-methyl 2-(tert-butoxy)-2-(7-chloro-5-methyl-2-phenylpyrazolo[1,5-a]pyrimidin-6-yl)acetate was dissolved in NMP (1 mL) and combined with 2-azaspiro[4.4]nonane (8.72 mg, 0.070 mmol) and N,N-diisopropylethylamine (27 mg, 0.21 mmol). This mixture was stirred at rt for 24 h. A 1M lithium hydroxide solution (0.348 mL, 0.348 mmol) was added to the reaction mixture and it was heated at 50° C. for 4 h to complete the ester hydrolysis. The reaction mixture was concentrated in vacuo and purified by Biotage (4 g column, 0-10% MeOH/CH$_2$Cl$_2$ ramp) to give 11.1 mg (27% yield) of S)-2-(tert-butoxy)-2-(5-methyl-2-phenyl-7-(2-azaspiro[4.4] nonan-2-yl)pyrazolo[1,5-a]pyrimidin-6-yl)acetic (1:1 solvate with NMP) as a yellow waxy solid.

$^1$H NMR (500 MHz, CDCl$_3$) δ 8.03-7.98 (m, 2H), 7.51-7.46 (m, 2H), 7.44-7.39 (m, 1H), 6.87 (s, 1H), 5.99-5.83 (m, 1H), 4.41-4.32 (m, 1H), 3.87 (d, J=8.5 Hz, 1H), 3.46-3.35 (m, 4H), 2.87 (s, 3H), 2.62 (s, 3H), 2.40 (t, J=8.2 Hz, 2H), 2.28-2.17 (m, 1H), 2.08-2.00 (m, 3H), 1.91-1.56 (m, 8H), 1.3-1.27 (s, 9H).

MS (M+H)=463.

EXAMPLE 27

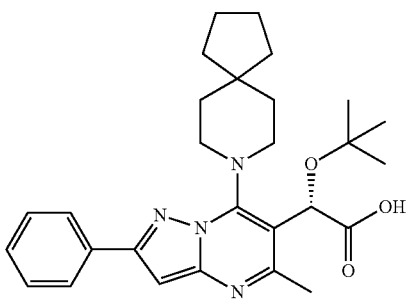 [SMILES: Cc1nc2cc(-c3ccccc3)nn2c(N2CCC3(CCCC3)CC2)c1[C@H](OC(C)(C)C)C(=O)O]

(S)-2-(tert-butoxy)-2-(5-methyl-2-phenyl-7-(8-azaspiro[4.5]decan-8-yl)pyrazolo[1,5-a]pyrimidin-6-yl) acetic acid As described in the example 28 except for the use of 8-azaspiro[4.5]decane hydrochloride (12.2 mg, 0.070 mmol). This procedure gave 21.1 mg (50% yield) of (S)-2-(tert-butoxy)-2-(5-methyl-2-phenyl-7-(8-azaspiro[4.5]decan-8-yl)pyrazolo[1,5-a]pyrimidin-6-yl)acetic acid (1:1 solvate with NMP) as a yellow solid.

$^1$H NMR (500 MHz, CDCl$_3$) δ 8.09-7.88 (m, 2H), 7.53-7.47 (m, 2H), 7.44-7.39 (m, 1H), 6.84 (s, 1H), 5.97 (br. s., 1H), 4.73-4.21 (m, 1H), 4.01-3.60 (m, 1H), 3.60-3.43 (m, 1H), 3.43-3.34 (m, 2H), 3.20-2.92 (m, 1H), 2.87 (s, 3H), 2.62 (s, 3H), 2.40 (d, J=8.2 Hz, 2H), 2.13-1.99 (m, 2H), 1.84-1.49 (m, 10H), 1.40-1.24 (s, 9H).

MS (M+H)=477.

EXAMPLE 28

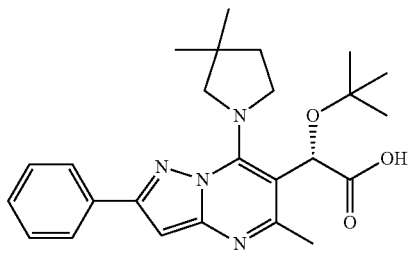 [SMILES: Cc1nc2cc(-c3ccccc3)nn2c(N2CCC(C)(C)C2)c1[C@H](OC(C)(C)C)C(=O)O]

(S)-2-(tert-butoxy)-2-(7-(3,3-dimethylpyrrolidin-1-yl)-5-methyl-2-phenylpyrazolo[1,5-a]pyrimidin-6-yl)acetic acid (S)-Methyl 2-(tert-butoxy)-2-(7-chloro-5-methyl-2-phenylpyrazolo[1,5-a]pyrimidin-6-yl)acetate (50 mg, 0.13 mmol) was dissolved in DMF (1 mL) and treated with 3,3-dimethylpyrrolidine hydrochloride (17.5 mg, 0.13 mmol) followed by N,N-diisopropylethylamine (0.068 mL, 0.387 mmol). This reaction mixture was stirred at rt for 18 h. The reaction mixture was partitioned between ether and water, and the organic phase was washed with water (2×). The organic phase was dried (MgSO$_4$) and concentrated to give 35 mg of the ester product as a yellow oil. (S)-methyl 2-(tert-butoxy)-2-(7-(3,3-dimethylpyrrolidin-1-yl)-5-methyl-2-phenylpyrazolo[1,5-a]pyrimidin-6-yl)acetate (34 mg, 0.075 mmol) was dissolved in ethanol (1 mL) and treated with 1M NaOH (0.226 mL, 0.226 mmol). The reaction mixture was stirred at rt for 18 h to complete the ester hydrolysis. The crude reaction mixture was partitioned between EtOAc and 1N HCl. The organic phase was dried (Na$_2$SO$_4$) and concentrated. The residue was purified by Biotage (2-10% MeOH/CH$_2$Cl$_2$) to give 12 mg of (S)-2-(tert-butoxy)-2-(7-(3,3-dimethylpyrrolidin-1-yl)-5-methyl-2-phenylpyrazolo[1,5-a]pyrimidin-6-yl)acetic acid as a white solid.

$^1$H NMR (500 MHz, CDCl$_3$) δ 8.05-7.97 (m, 2H), 7.53-7.45 (m, 2H), 7.44-7.38 (m, 1H), 6.87 (s, 1H), 5.93 (s, 1H), 4.46-4.38 (m, 1H), 3.77 (d, J=8.7 Hz, 1H), 3.48-3.41 (m, 1H), 3.28 (d, J=8.7 Hz, 1H), 2.63 (s, 3H), 2.17-2.09 (m, 1H), 1.97-1.90 (m, 1H), 1.34 (s, 3H), 1.30 (s, 12H). MS (M+H)=437.

EXAMPLE 29

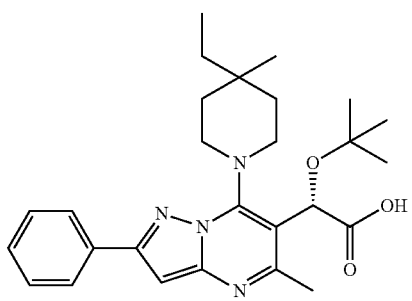 [SMILES: CCC1(C)CCN(c2c([C@H](OC(C)(C)C)C(=O)O)c(C)nc3cc(-c4ccccc4)nn23)CC1]

(S)-2-(tert-butoxy)-2-(7-(4-ethyl-4-methylpiperidin-1-yl)-5-methyl-2-phenylpyrazolo[1,5-a]pyrimidin-6-yl)acetic acid Prepared as described above using 4-ethyl-4-methylpiperidine (16.4 mg, 0.13 mmol) to give 12 mg of (S)-2-(tert-butoxy)-2-(7-(4-ethyl-4-methylpiperidin-1-yl)-5-methyl-2-phenylpyrazolo[1,5-a]pyrimidin-6-yl)acetic acid as a white solid.

$^1$H NMR (500 MHz, CDCl$_3$) δ 8.02 (d, J=7.1 Hz, 2H), 7.55-7.46 (m, 2H), 7.45-7.37 (m, 1H), 6.91-6.79 (m, 1H), 5.95 (br. s., 1H), 4.68-4.44 (m, 1H), 3.85 (br. s., 1H), 3.57-3.25 (m, 1H), 2.97 (br. s., 1H), 2.64-2.60 (s, 3H), 1.70-1.52 (m, 6H), 1.35-1.30 (s, 9H), 1.21-1.10 (m, 3H), 0.98-0.91 (m, 3H).
MS (M+H)=465.

EXAMPLE 30

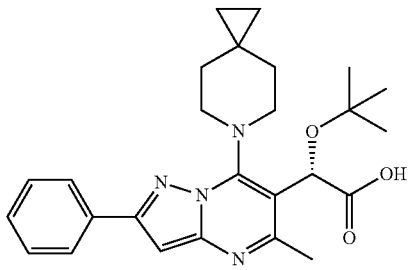 [SMILES: Cc1nc2cc(-c3ccccc3)nn2c(N2CCC3(CC2)CC3)c1[C@H](OC(C)(C)C)C(=O)O]

(S)-2-(tert-butoxy)-2-(5-methyl-2-phenyl-7-(6-azaspiro[2.5]octan-6-yl)pyrazolo[1,5-a]pyrimidin-6-yl)acetic acid As described above using 2 equivalents of 6-azaspiro[2.5]octane hydrochloride (38.1 mg, 0.258 mmol) to give ~30 mg of crude product (~85% pure) after Biotage purification. This material was further purified by prep HPLC (Waters Sunfire C18 OBD 30×100 5μ, 15 min gradient, 2 min hold time; 80-100% B. Solvent A: 90% water/10% MeOH/0.1% TFA; Solvent B: 10% Water/90% MeOH/0.1% TFA) to give 15 mg of (S)-2-(tert-butoxy)-2-(5-methyl-2-phenyl-7-(6-azaspiro[2.5]octan-6-yl)pyrazolo[1,5-a]pyrimidin-6-yl)acetic acid as a yellow solid.

$^1$H NMR (400 MHz, CDCl$_3$) δ 7.98 (dd, J=7.7, 1.6 Hz, 2H), 7.62-7.44 (m, 3H), 7.04 (s, 1H), 5.49 (s, 1H), 4.24-4.05 (m, 2H), 3.77 (br. s., 2H), 2.73 (s, 3H), 1.89 (br. s., 2H), 1.63 (br. s., 2H), 1.27 (s, 9H), 0.60-0.44 (m, 4H).
MS (M+H)=449.

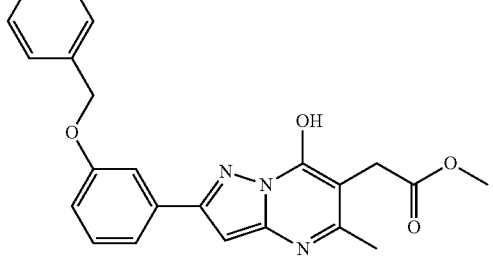

Methyl 2-(2-(3-(benzyloxy)phenyl)-7-hydroxy-5-methylpyrazolo[1,5-a]pyrimidin-6-yl)acetate To a solution of 3-(3-(benzyloxy)phenyl-1H-pyrazol-5-amine (1 g, 3.8 mmol) and dimethyl 2-acetylsuccinate (2.13 g, 11 mmol) in xylene (50 mL) was added p-toluenesulfonic acid monohydrate (7 mg, 0.04 mmol). The reaction mixture was heated at reflux under a Dean-Stark trap for 20 h. The grey solid was filtered and washed with hexanes to afford the title compound (1.1 g, 73%).

$^1$H-NMR (400 MHz, DMSO-d6) δ 2.32 (s, 3H), 3.57 (s, 2H), 3.62 (s, 3H), 5.20 (s, 2H), 6.60 (s, 1H), 7.07 (dd, 1H), 7.32-7.36 (m, 1H), 7.37-7.43 (m, 3H), 7.50 (d, 2H), 7.56-7.62 (m, 2H), 12.41 (s, 1H)

| Methyl 2-(2-(3-(benzyloxy)phenyl)-7-hydroxy-5-methylpyrazolo[1,5-a]pyrimidin-6-yl)acetate | |
|---|---|
| MS (M + H)$^+$ Calcd. | 404 |
| MS (M + H)$^+$ Observ. | 404 |
| Retention Time | 2.02 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:water:TFA |
| Column | Phenomenex Luna C18, 30 × 2, 3u |

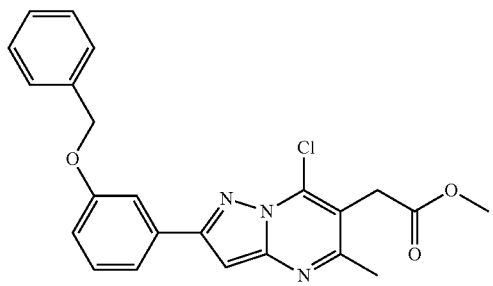 [SMILES: COC(=O)Cc1c(C)nc2cc(-c3cccc(OCc4ccccc4)c3)nn2c1Cl]

Methyl 2-(2-(3-(benzyloxy)phenyl)-7-chloro-5-methylpyrazolo[1,5-a]pyrimidin-6-yl)acetate To methyl 2-(2-(3-(benzyloxy)phenyl)-7-hydroxy-5-methylpyrazolo[1,5-a]pyrimidin-6-yl)acetate (0.3 g, 0.75 mmol) was added POCl$_3$ (3 mL). The reaction mixture was heated at reflux for 2 h. After cooling, the reaction mixture was added drop-wise to ice-water. A brown solid precipitated. The solid was filtered and washed with water, then dissolved in ethyl acetate. The organic solution was washed with saturated NaHCO$_3$ and dried over sodium sulfate. The solvent was evaporated to give the title compound (2.77 g, 84%).
$^1$H-NMR (400 MHz, DMSO-d$_6$) δ 2.56 (s, 3H), 3.69 (s, 3H), 4.01 (s, 2H), 5.20 (s, 2H), 7.10 (dd, 1H), 7.29 (s, 1H), 7.32-7.37 (m, 1H), 7.39-7.45 (m, 3H), 7.51 (d, 2H), 7.63-7.69 (m, 2H).

| Methyl 2-(2-(3-(benzyloxy)phenyl)-7-chloro-5-methylpyrazolo[1,5-a]pyrimidin-6-yl)acetate. | |
|---|---|
| MS (M + H)$^+$ Calcd. | 422 |
| MS (M + H)$^+$ Observ. | 422 |
| Retention Time | 2.32 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

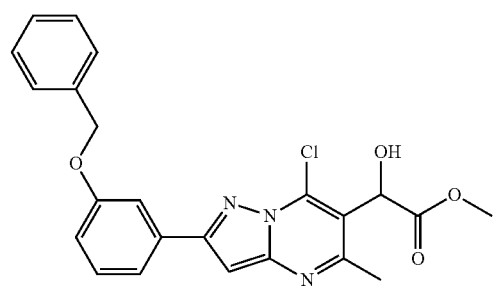 [SMILES: COC(=O)C(O)c1c(C)nc2cc(-c3cccc(OCc4ccccc4)c3)nn2c1Cl]

Methyl 2-(2-(3-(benzyloxy)phenyl)-7-chloro-5-methylpyrazolo[1,5-a]pyrimidin-6-yl)-2-hydroxyacetate To a stirred solution of KHMDS (0.5 M in toluene, 1.50 mL, 0.78 mmol) in THF (12 mL) at −78° C. was added a solution of methyl 2-(2-(3-(benzyloxy)phenyl)-7-chloro-5-methylpyrazolo[1,5-a]pyrimidin-6-yl)acetate (0.35 g, 0.83 mmol) in THF (12 mL) dropwise over 40 min. The mixture was stirred at −78° C. for 30 min. A solution of 3-phenyl-2-(phenylsulfonyl)-1,2-oxaziridine (0.33 g, 1.25 mmol) in THF (24 mL) was added over 20 min and the reaction mixture was stirred for additional 30 min at −78° C. The reaction mixture was quenched with saturated NH$_4$Cl aqueous solution (2 mL). The reaction mixture was allowed to warm to room temperature and then diluted with ethyl acetate (100 mL). The organic phase was washed with water and brine and dried with sodium sulfate. The solvent was evaporated. Purification by silica gel chromatography provided the title compound (80 mg, 22%). Used as is in the next step.

| Methyl 2-(2-(3-(benzyloxy)phenyl)-7-chloro-5-methylpyrazolo[1,5-a]pyrimidin-6-yl)-2-hydroxyacetate. | |
|---|---|
| MS (M + H)$^+$ Calcd. | 438 |
| MS (M + H)$^+$ Observ. | 438 |
| Retention Time | 2.22 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

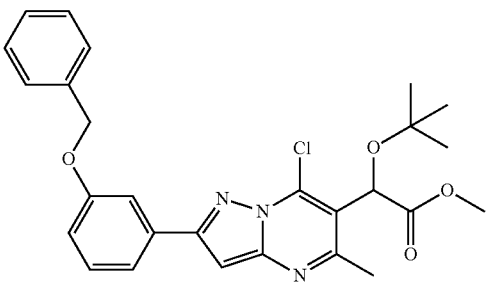 [SMILES: COC(=O)C(OC(C)(C)C)c1c(C)nc2cc(-c3cccc(OCc4ccccc4)c3)nn2c1Cl]

Methyl 2-(2-(3-(benzyloxy)phenyl)-7-chloro-5-methylpyrazolo[1,5-a]pyrimidin-6-yl)-2-(tert-butoxy)acetate To a suspension of methyl 2-(2-(3-(benzyloxy)phenyl)-7-chloro-5-methylpyrazolo[1,5-a]pyrimidin-6-yl)-2-hydroxyacetate. (80 mg, 0.18 mmol) in tert-butyl acetate (5 mL) at room temperature was added $CH_2Cl_2$ (10 mL) followed by perchloric acid (27 mg, 0.26 mmol). The reaction mixture was stirred for 2 h at room temperature. The reaction mixture was quenched with water and diluted with ethyl acetate. The organic phase was washed with saturated $NaHCO_3$ and dried over sodium sulfate. The solvent was evaporated. Purification by silica gel chromatography provided the title compound (80 mg, 92%). Used as is in the next step.

| Methyl 2-(2-(3-(benzyloxy)phenyl)-7-chloro-5-methylpyrazolo[1,5-a]pyrimidin-6-yl)-2-(tert-butoxy)acetate. | |
|---|---|
| MS (M + H)+ Calcd. | 494 |
| MS (M + H)+ Observ. | 494 |
| Retention Time | 2.55 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

EXAMPLE 31

2-(2-(3-(benzyloxy)phenyl)-5-methyl-7-(4-methylpiperidin-1-yl)pyrazolo[1,5-a]pyrimidin-6-yl)20(tert-butoxy)acetic acid

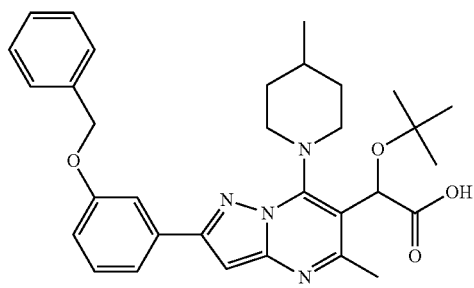 [SMILES: Cc1nc2cc(-c3cccc(OCc4ccccc4)c3)nn2c(N2CCC(C)CC2)c1C(OC(C)(C)C)C(=O)O]

To a solution of methyl 2-(2-(3-(benzyloxy)phenyl)-7-chloro-5-methylpyrazolo[1,5-a]pyrimidin-6-yl)-2-(tert-butoxy)acetate (20 mg, 0.040 mmol) and 4-methylpiperidine.HCl (4.02 mg, 0.040 mmol) in NMP (1 mL) was added DIEA (0.047 mL, 0.272 mmol) and the mixture was heated at 50° C. for 2 h. Then, 1N LiOH (0.272 mL, 0.272 mmol) was added to the reaction mixture and the contents were heated at 50° C. for 2 h. The reaction mixture was then filtered and purified by prep-HPLC to afford 2-(tert-butoxy)-2-(7-(4-methylpiperidin-1-yl)-5-methyl-2-phenylpyrazolo[1,5a]pyrimidin-6-yl)acetic acid (8.5 mg, 0.016 mmol, 39% yield) as white solid.
$^1$H NMR (500 MHz, DMSO-$d_6$) δ 1.04 (d, 3H), 1.18 (s, 9H), 1.63-1.88 (m, 6H), 2.75 (s, 2H), 2.91 (s, 2H), 5.22 (s, 2H), 6.97 (s, 2H), 7.07 (dd, 2H), 7.34-7.47 (m, 7H), 7.52 (d, 4H), 7.59-7.70 (m, 4H), 7.97 (s, 1H).

| Methyl 2-tert-butoxy-2-(7-chloro-5-methyl-2-phenylpyrazolo[1,5-a]pyrimidin-6-yl)acetate | |
|---|---|
| MS (M + H)+ Calcd. | 543 |
| MS (M + H)+ Observ. | 543 |
| Retention Time | 4.75 min |
| LC Condition | |
| Solvent A | 5% methanol: 95% water: 10 mM NH4OAc |
| Solvent B | 95% methanol: 5% water: 10 mM NH4OAc |
| Start % B | 0 |
| Final % B | 100 |
| Gradient Time | 5 min |
| Flow Rate | 0.5 mL/min |
| Wavelength | 220 |
| Solvent Pair | methanol:water:ammonium acetate |
| Column | Waters BEH C18, 2.0 × 50 mm |

EXAMPLE 32

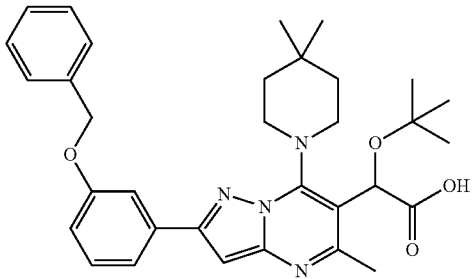 [SMILES: Cc1nc2cc(-c3cccc(OCc4ccccc4)c3)nn2c(N2CCC(C)(C)CC2)c1C(OC(C)(C)C)C(=O)O]

2-(2-(3-(benzyloxy)phenyl)-7-(4,4-dimethylpiperidin-1-yl)-5-methylpyrazolo[1,5-a]pyrimidin-6-yl)2-(tert-butoxy)acetic acid

| 2-(2-(3-(Benzyloxy)phenyl)-7-(4,4-dimethylpiperidin-1-yl)-5-methylpyrazolo[1,5-a]pyrimidin-6-yl)-2-(tert-butoxy)acetic acid | |
|---|---|
| MS (M + H)+ Calcd. | 557 |
| MS (M + H)+ Observ. | 557 |
| Retention Time | 2.573 min |
| LC Condition | |
| Solvent A | 10% methanol: 90% Water: 0.1% TFA |
| Solvent B | 90% methanol: 10% Water: 0.1% TFA |

-continued 2-(2-(3-(Benzyloxy)phenyl)-7-(4,4-dimethylpiperidin-1-yl)-5-methylpyrazolo[1,5-a]pyrimidin-6-yl)-2-(tert-butoxy)acetic acid

| | |
|---|---|
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, DMSO-$d_6$) δ 7.72-7.67 (m, 1H), 7.63 (d, J=7.6 Hz, 1H), 7.53-7.48 (m, 2H), 7.42 (t, J=7.8 Hz, 3H), 7.38-7.33 (m, 1H), 7.07 (dd, J=8.2, 1.8 Hz, 1H), 7.03 (s, 1H), 5.71 (s., 1H), 5.21 (s, 2H), 3.36 (br. s., 4H), 2.52 (s., 3H), 1.64 (br. s., 2H), 1.51 (br. s., 2H), 1.19 (s, 9H), 1.11 (br. s., 6H).

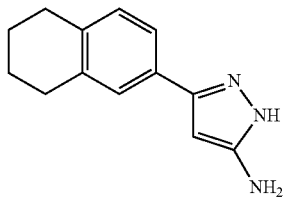 [SMILES: Nc1cc(-c2ccc3c(c2)CCCC3)n[nH]1]

3-(5,6,7,8-tetrahydronaphthalen-2-yl)-1H-pyrazol-5-amine

Acetonitrile (21.48 mL, 411 mmol) was added to a stirred suspension of 60% NaH (7.05 g, 176 mmol) in dioxane (200 mL) and the resulting mixture was stirred at room temp for 20 min. Solution of ethyl 5,6,7,8-tetrahydronaphthalene-2-carboxylate (12 g, 58.7 mmol) in dioxane (50 mL) was then added and the mixture was heated at reflux for 4 h. After cooling to room temp, water followed by 1N HCl (100 mL) was added and the mixture was extracted twice with dichloromethane, dried (Na$_2$SO$_4$), filtered and concentrated to afford 3-oxo-3-(5,6,7,8-tetrahydronaphthalen-2-yl)propanenitrile as dark solid. A mixture of this syrup and hydrazine hydrate (2.77 mL, 88 mmol) in ethanol (200 mL) was heated at reflux for 16 h. The reaction mixture was cooled to room temp and concentrated in vacuo. The residue was diluted with dichloromethane and washed with water, dried (Na$_2$SO$_4$), filtered, concentrated and purified by silica gel chromatography (5-10% MeOH/CH$_2$Cl$_2$) to afford desired 3-(5,6,7,8-tetrahydronaphthalen-2-yl)-1H-pyrazol-5-amine (6.1 g, 28.6 mmol, 48.7% yield) as yellow solid. $^1$H NMR (400 MHz, CDCl$_3$) δ 7.26 (d, J=3.5 Hz, 2H), 7.12 (d, J=7.8 Hz, 1H), 5.89 (s, 1H), 4.14 (br. s., 3H), 2.88-2.75 (m, 4H), 1.83 (dt, J=6.1, 3.4 Hz, 4H). LCMS (M+H)=214.2.

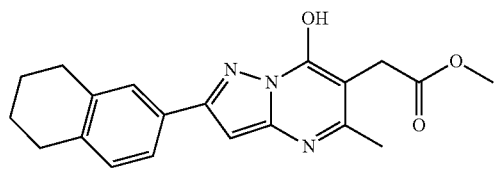 [SMILES: COC(=O)Cc1c(C)nc2cc(-c3ccc4c(c3)CCCC4)nn2c1O]

Methyl 2-(7-hydroxy-5-methyl-2-(5,6,7,8-tetrahydronaphthalen-2-yl)pyrazolo[1,5-a]pyrimidin-6-yl)acetate A suspension of 3-(5,6,7,8-tetrahydronaphthalen-2-yl)-1H-pyrazol-5-amine (6 g, 28.1 mmol), 1-ethyl 4-methyl 2-acetylsuccinate (24.52 mL, 141 mmol) and Ts-OH.H$_2$O (0.096 g, 0.506 mmol) in o-xylene (200 mL) was heated at 150° C. (oil bath temp) for 16 h. (Note: mixture became homogeneous and in about 15 min slowly yellow solid started crashing out of the reaction.) Then, the reaction mixture was cooled, diluted with hexanes (300 mL), filtered, washed with hexanes and dried to afford methyl 2-(7-hydroxy-5-methyl-2-(5,6,7,8-tetrahydronaphthalen-2-yl)pyrazolo[1,5-a]pyrimidin-6-yl)acetate (8.4 g, 23.90 mmol, 85% yield) as light yellow solid. $^1$H NMR (400 MHz, DMSO-$d_6$) δ 12.35 (s, 1H), 7.78-7.62 (m, 2H), 7.15 (d, J=8.5 Hz, 1H), 6.52 (s, 1H), 3.64 (s, 3H), 3.58 (s, 2H), 2.82-2.77 (m, 4H), 2.33 (s, 3H), 1.78 (t, J=3.0 Hz, 4H). LCMS (M+H)=352.3.

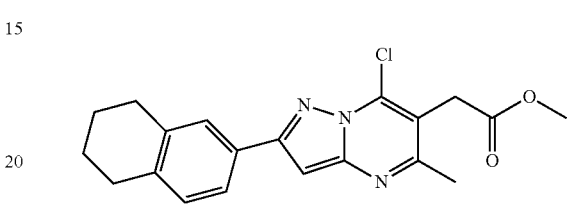

Methyl 2-(7-chloro-5-methyl-2-(5,6,7,8-tetrahydronaphthalen-2-yl)pyrazolo[1,5-a]pyrimidin-6-yl)acetate Mixture of methyl 2-(7-hydroxy-5-methyl-2-(5,6,7,8-tetrahydronaphthalen-2-yl)pyrazolo[1,5-a]pyrimidin-6-yl)acetate (8.4 g, 23.90 mmol) and phosphoryl trichloride (10.94 ml, 120 mmol) was heated at reflux for 4 h. Then, cooled, concentrated and the dark residue taken up in EtOAc (500 mL) and stirred with ice-water for 30 min. Aqueous layer separated and organic layer washed with water (2×50 mL). The combine aq layers extracted with EtOAc (2×100 mL) and the combined organic layers washed with brine (100 mL), dried (Na$_2$SO$_4$/C), filtered and concentrated to give dark paste. Purification by flash column chromatography on silica gel column using 5-20% EtOAc/Hex afforded methyl 2-(7-chloro-5-methyl-2-(5,6,7,8-tetrahydronaphthalen-2-yl)pyrazolo[1,5-a]pyrimidin-6-yl)acetate (5.6 g, 15.14 mmol, 63.3% yield) as off-white solid. $^1$H NMR (500 MHz, CDCl$_3$) δ 7.76-7.71 (m, 2H), 7.18 (d, J=7.6 Hz, 1H), 6.92 (s, 1H), 3.93 (s, 2H), 3.78 (s, 3H), 2.89-2.84 (m, 4H), 2.63 (s, 3H), 1.86 (dt, J=6.5, 3.3 Hz, 4H). LCMS (M+H)=370.11.

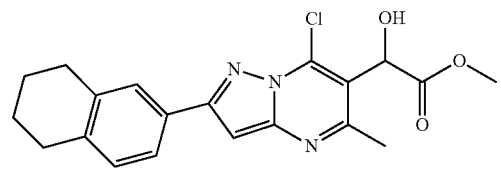 [SMILES: COC(=O)C(O)c1c(C)nc2cc(-c3ccc4c(c3)CCCC4)nn2c1Cl]

Methyl 2-(7-chloro-5-methyl-2-(5,6,7,8-tetrahydronaphthalen-2-yl)pyrazolo[1,5-a]pyrimidin-6-yl)-2-hydroxyacetate To a stirred solution of 0.9M KHMDS/THF (9.76 mL, 8.79 mmol) in THF (25 mL) at −78° C. was added dropwise a THF (25 mL) solution of methyl 2-(7-chloro-5-methyl-2-(5,6,7,8-tetrahydronaphthalen-2-yl)pyrazolo[1,5-a]pyrimidin-6-yl)acetate (2.5 g, 6.76 mmol) over 5 min. After 30 min, a THF (20 mL) solution of 3-phenyl-2-(phenylsulfonyl)-1,2-oxaziridine (2.296 g, 8.79 mmol) was added to the resulting red reaction mixture and stirred for additional 30 min at −78° C. Then, the resulting orange reaction mixture was quenched with sat. NH₄Cl (50 mL), diluted with EtOAc (200 mL), washed with water (100 mL), brine (100 mL), dried (Na₂SO₄), filtered and concentrated to give yellow solid. This was purified by flash column chromatography on silica gel column (5-40% EtOAc/hexane) to afford the 2.2 g desired methyl 2-(7-chloro-5-methyl-2-(5,6,7,8-tetrahydronaphthalen-2-yl)pyrazolo[1,5-a]pyrimidin-6-yl)-2-hydroxyacetate as off-white solid. Impurities were present by NMR and LCMS. Used in the next step without further purification. ¹H NMR (500 MHz, CDCl₃) δ 7.77-7.71 (m, 2H), 7.19 (d, J=7.6 Hz, 1H), 6.93 (s, 1H), 5.78 (d, J=2.7 Hz, 1H), 3.86 (s, 3H), 3.56 (d, J=2.7 Hz, 1H), 2.89-1.81 (m, 4H), 2.64 (s, 3H), 1.86 (dt, J=6.5, 3.3 Hz, 4H). LCMS (M+H)=386.3.

was slowly warmed to −15 C and stirred for additional 30 min. and diluted with EtOAc (30 mL) and sat. Na₂CO₃ (10 mL). The mixture was stirred vigorously for 30 min, and the organic phase washed with sat Na₂CO₃ (2×5 mL), dried (Na2SO4), filtered, concentrated and the residue was purified by silica gel chromatography (5-70% EtOAc/hexane) to afford desired (S)-methyl 2-(7-chloro-5-methyl-2-(5,6,7,8-tetrahydronaphthalen-2-yl)pyrazolo[1,5-a]pyrimidin-6-yl)-2-hydroxyacetate (888 mg, 2.301 mmol, 88% yield) as off-white solid. EE=95.4% ¹H NMR (500 MHz, CDCl₃) δ 7.77-7.71 (m, 2H), 7.19 (d, J=7.6 Hz, 1H), 6.93 (s, 1H), 5.78 (d, J=2.7 Hz, 1H), 3.86 (s, 3H), 3.56 (d, J=2.7 Hz, 1H), 2.89-1.81 (m, 4H), 2.64 (s, 3H), 1.86 (dt, J=6.5, 3.3 Hz, 4H). LCMS (M+H)=386.3.

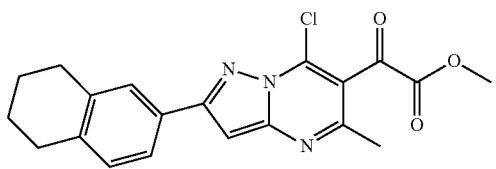 [SMILES: COC(=O)C(=O)c1c(C)nc2cc(-c3ccc4c(c3)CCCC4)nn2c1Cl]

Methyl 2-(7-chloro-5-methyl-2-(5,6,7,8-tetrahydronaphthalen-2-yl)pyrazolo[1,5-a]pyrimidin-6-yl)-2-oxoacetate

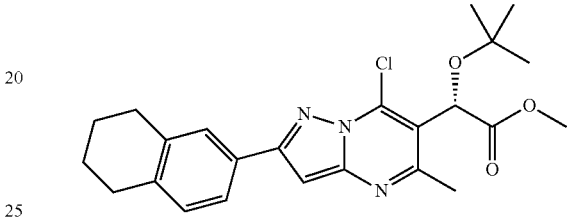

(S)-Methyl 2-(tert-butoxy)-2-(7-chloro-5-methyl-2-(5,6,7,8-tetrahydronaphthalen-2-yl)pyrazolo[1,5-a]pyrimidin-6-yl)acetate To a mixture of methyl 2-(7-chloro-5-methyl-2-(5,6,7,8-tetrahydronaphthalen-2-yl)pyrazolo[1,5-a]pyrimidin-6-yl)-2-hydroxyacetate (2.5 g, 6.48 mmol) in CH₂Cl₂ (70 mL) was added Dess-Martin periodinane (3.02 g, 7.13 mmol) and stirred at room temp for 1 h. Then diluted with ethyl acetate (500 mL) and washed with sat. NaHCO₃ solution (100 mL), dried (Na₂SO₄), filtered and concentrated and the residue was purified by silica gel chromatography (5-30% EtOAc/hexane) to afford desired methyl 2-(7-chloro-5-methyl-2-(5,6,7,8-tetrahydronaphthalen-2-yl)pyrazolo[1,5-a]pyrimidin-6-yl)-2-oxoacetate (1.1 g, 2.87 mmol, 44.2% yield) as off-white solid. 44% yield based on 2 steps. ¹H NMR (500 MHz, CDCl₃) δ 7.77-7.71 (m, 2H), 7.20 (d, J=7.6 Hz, 1H), 7.00 (s, 1H), 4.02 (s, 3H), 2.89-2.83 (m, 4H), 2.64 (s, 3H), 1.86 (dt, J=6.5, 3.3 Hz, 4H). LCMS (M+H)=384.3.

To a stirred solution of (S)-methyl 2-(7-chloro-5-methyl-2-(5,6,7,8-tetrahydronaphthalen-2-yl)pyrazolo[1,5-a]pyrimidin-6-yl)-2-hydroxyacetate (888 mg, 2.301 mmol) in CH₂Cl₂ (45 mL) and t-butyl acetate (21.76 mL, 161 mmol) at rt was added 70% perchloric acid (0.593 mL, 6.90 mmol). After 2.5 h, the reaction mixture was diluted with CH₂Cl₂ (50 mL), carefully quenched with sat. NaHCO₃ (50 mL), organic layer separated and washed with brine (100 mL), dried (Na₂SO₄), filtered and concentrated to give yellow liquid. This was purified by flash column chromatography on silica gel column using (10-40% EtOAc/Hex as eluant) to afford the desired (S)-methyl 2-(tert-butoxy)-2-(7-chloro-5-methyl-2-(5,6,7,8-tetrahydronaphthalen-2-yl)pyrazolo[1,5-a]pyrimidin-6-yl)acetate (735 mg, 1.663 mmol, 72.3% yield) as white solid. 150 mg of starting material was also recovered. ¹H NMR (500 MHz, CDCl₃) δ 7.76-7.70 (m, 2H), 7.18 (d, J=7.9 Hz, 1H), 6.91 (s, 1H), 5.68 (s, 1H), 3.76 (s, 3H), 2.89-2.84 (m, 4H), 2.68 (s, 3H), 1.89-1.83 (m, 4H), 1.30 (s, 9H). LCMS (M+H)=444.3.

EXAMPLE 33

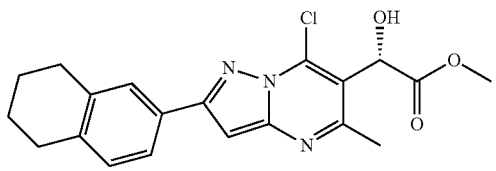

(S)-Methyl 2-(7-chloro-5-methyl-2-(5,6,7,8-tetrahydronaphthalen-2-yl)pyrazolo[1,5-a]pyrimidin-6-yl)-2-hydroxyacetate To a stirred yellow solution of methyl 2-(7-chloro-5-methyl-2-(5,6,7,8-tetrahydronaphthalen-2-yl)pyrazolo[1,5-a]pyrimidin-6-yl)-2-oxoacetate (1 g, 2.61 mmol) in anhydrous toluene (25 mL) was added 1.1M (R)-1-methyl-3,3-diphenylhexahydropyrrolo[1,2-c][1,3,2]oxazaborole/toluene (0.947 mL, 1.042 mmol). The mixture was cooled to −35° C. and a solution of 1M catechoborane/THF (3.65 mL, 3.65 mmol) was added over 10 min. After 30 min, the reaction mixture

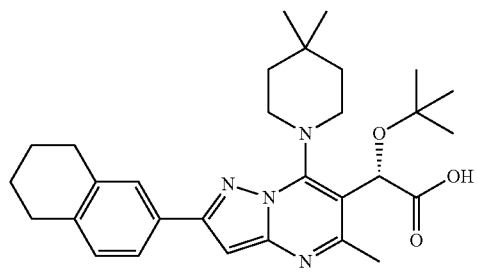 [SMILES: Cc1nc2cc(-c3ccc4c(c3)CCCC4)nn2c(N2CCC(C)(C)CC2)c1[C@H](OC(C)(C)C)C(=O)O]

(S)-2-(tert-Butoxy)-2-(7-(4,4-dimethylpiperidin-1-yl)-5-methyl-2-(5,6,7,8-tetrahydronaphthalen-2-yl)pyrazolo[1,5-a]pyrimidin-6-yl)acetic acid To a solution of (S)-methyl 2-(tert-butoxy)-2-(7-chloro-5-methyl-2-(5,6,7,8-tetrahydronaphthalen-2-yl)pyrazolo[1,5-a]pyrimidin-6-yl)acetate (40 mg, 0.091 mmol) and 4,4-dimethylpiperidine.HCl (13.55 mg, 0.091 mmol) in NMP (1 mL) was added DIEA (0.047 mL, 0.272 mmol) and the mixture was heated at 50° C. for 2 h. Then, 1N NaOH (0.272 mL, 0.272 mmol) was added to the reaction mixture and the contents were heated at 50° C. for 2 h. The reaction mixture was then filtered and purified by prep-HPLC to afford (S)-2-(tert-butoxy)-2-(7-(4,4-dimethylpiperidin-1-yl)-5-methyl-2-(5,6,7,8-tetrahydronaphthalen-2-yl)pyrazolo[1,5-a]pyrimidin-6-yl)acetic acid (13.5 mg, 0.027 mmol, 29.6% yield) as white solid. $^1$H NMR (400 MHz, DMSO-d$_6$) δ 7.77-7.71 (m, 2H), 7.19 (s, 1H), 6.95 (s, 1H), 5.80 (s, 1H), 2.91 (s, 2H), 2.84-2.76 (m, 4H), 1.83-1.75 (m, 4H), 1.65-1.58 (m, 2H), 1.56-1.45 (m, 2H), 1.20 (s, 9H), 1.11 (s., 6H). LCMS (M+H)=506.5.

EXAMPLE 34

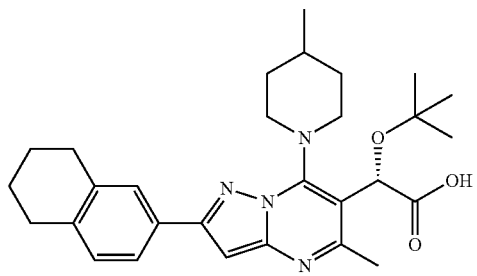 [SMILES: Cc1nc2cc(-c3ccc4c(c3)CCCC4)nn2c(N2CCC(C)CC2)c1[C@H](OC(C)(C)C)C(=O)O]

(S)-2-(tert-Butoxy)-2-(5-methyl-7-(4-methylpiperidin-1-yl)-2-(5,6,7,8-tetrahydronaphthalen-2-yl)pyrazolo[1,5-a]pyrimidin-6-yl)acetic acid Prepared according to the procedure described for Example 33 using 4-methylpiperidine. $^1$H NMR (400 MHz, DMSO-d$_6$) δ 7.74 (d, J=7.8 Hz, 1H), 7.71 (s, 1H), 7.17 (d, J=8.0 Hz, 1H), 6.94 (s, 1H), 2.91 (s, 3H), 2.86-2.76 (m, 4H), 1.88-1.63 (m, 8H), 1.20 (s, 9H), 1.04 (d, J=6.0 Hz, 3H). LCMS (M+H)=492.5.

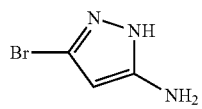

3-Bromo-1H-pyrazol-5-amine was prepared as described in reference: *Journal of Medicinal Chemistry*, 2010, 53, 3, 1245.

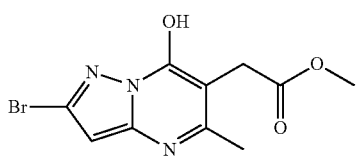 [SMILES: COC(=O)Cc1c(C)nc2cc(Br)nn2c1O]

Methyl 2-(2-bromo-7-hydroxy-5-methylpyrazolo[1,5-a]pyrimidin-6-yl)acetate

To a solution of 3-bromo-1H-pyrazol-5-amine (0.2 g, 1.235 mmol) and dimethyl 2-acetylsuccinate (0.697 g, 3.70 mmol) in xylene (10 mL) was added p-toluenesulfonic acid monohydrate (2 mg, 10.51 μmol). The reaction mixture was heated at reflux under a Dean-Stark trap for 8 h. The solid was filtered and washed with hexanes to afford the title compound (0.201 g, 54.2%). $^1$H NMR (400 MHz, MeOD) δ 2.37 (3H, s), 3.65 (2H, s), 3.71 (3H, s), 6.20 (1H, s).

| Methyl 2-(2-bromo-7-hydroxy-5-methylpyrazolo[1,5-a]pyrimidin-6-yl)acetate. | |
|---|---|
| MS (M + H)$^+$ Calcd. | 300 |
| MS (M + H)$^+$ Observ. | 300 |
| Retention Time | 1.32 min |
| LC Condition | |
| Solvent A | 10% MeOH: 90% Water: 0.1% TFA |
| Solvent B | 90% MeOH: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | MeOH:Water:TFA |
| Column | Phenomenex Luna C18, 30 × 2, 3u |

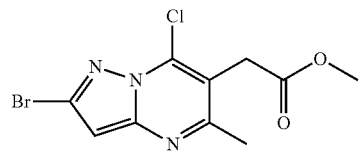 [SMILES: COC(=O)Cc1c(C)nc2cc(Br)nn2c1Cl]

Methyl 2-(2-bromo-7-chloro-5-methylpyrazolo[1,5-a]pyrimidin-6-yl)acetate

To methyl 2-(2-bromo-5-methyl-7-oxo-4,7-dihydropyrazolo[1,5-a]pyrimidin-6-yl)acetate (180 mg, 0.600 mmol) was added POCl$_3$ (1 mL, 10.73 mmol). The reaction mixture was heated at reflux for 1 h. After cooling, the reaction mixture was added drop-wise to ice-water. A brown solid precipitated. The solid was filtered and washed with water to give the title compound (158 mg, 83%). $^1$H NMR (500 MHz, DMSO-d$_6$) δ 2.56 (3H, s), 3.69 (3H, s), 4.01 (2H, s), 6.99 (1H, s).

| Methyl 2-(2-bromo-7-chloro-5-methylpyrazolo[1,5-a]pyrimidin-6-yl)acetate | |
|---|---|
| MS (M + H)$^+$ Calcd. | 318 |
| MS (M + H)$^+$ Observ. | 318 |
| Retention Time | 1.78 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

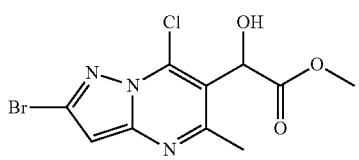 [SMILES: COC(=O)C(O)c1c(C)nc2cc(Br)nn2c1Cl]

Methyl 2-(2-bromo-7-chloro-5-methylpyrazolo[1,5-a]pyrimidin-6-yl)-2-hydroxyacetate To a stirred solution of KHMDS (0.5 M in toluene, 2.83 mL, 1.413 mmol) in THF (6 mL) at −78° C. was added a solution of methyl 2-(2-bromo-7-chloro-5-methylpyrazolo[1,5-a]pyrimidin-6-yl)acetate (300 mg, 0.942 mmol) in THF (6 mL) dropwise over 20 min. The mixture was stirred at −78° C. for 30 min. A solution of 3-phenyl-2-(phenylsulfonyl)-1,2-oxaziridine (369 mg, 1.413 mmol) in THF (6 mL) was added over 15 min and the reaction mixture was stirred for additional 60 min at −78° C. The reaction mixture was quenched with saturated NH$_4$Cl aqueous solution (4 mL). The reaction mixture was allowed to warm to room temperature and then diluted with ethyl acetate (100 mL). The organic phase was washed with water and brine and dried with sodium sulfate. The solvent was evaporated. Purification by silica gel chromatography provided the title compound (85 mg, 27%). $^1$H NMR (400 MHz, CHLOROFORM-d) δ 2.63 (3 H, s), 3.84 (3 H, s), 5.74 (1 H, s), 6.71 (1 H, s).

| Methyl 2-(2-bromo-7-chloro-5-methylpyrazolo[1,5-a]pyrimidin-6-yl)-2-hydroxyacetate | |
|---|---|
| MS (M + H)$^+$ Calcd. | 334 |
| MS (M + H)$^+$ Observ. | 334 |
| Retention Time | 1.692 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

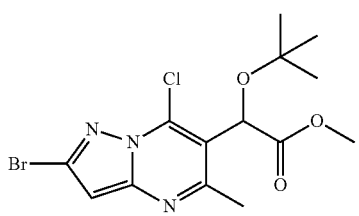 [SMILES: COC(=O)C(OC(C)(C)C)c1c(C)nc2cc(Br)nn2c1Cl]

Methyl 2-(2-bromo-7-chloro-5-methylpyrazolo[1,5-a]pyrimidin-6-yl)-2-tert-butoxyacetate To a suspension of methyl 2-(2-bromo-7-chloro-5-methylpyrazolo[1,5-a]pyrimidin-6-yl)-2-hydroxyacetate (80 mg, 0.239 mmol) in tert-butyl acetate (2 mL) at room temperature was added CH$_2$Cl$_2$ (2 mL) followed by perchloric acid (0.022 mL, 0.359 mmol). The reaction mixture was stirred for 4 h at room temperature. The reaction mixture was quenched with water and diluted with ethyl acetate. The organic phase was washed with saturated NaHCO$_3$ and dried over sodium sulfate. The solvent was evaporated. Purification by silica gel chromatography provided the title compound (56 mg, 59.9%). $^1$H NMR (500 MHz, MeOD) δ 1.27 (9 H, s), 2.62 (3 H, s), 3.74 (3 H, s), 5.75 (1 H, s), 6.75 (1 H, s).

| Methyl 2-(2-bromo-7-chloro-5-methylpyrazolo[1,5-a]pyrimidin-6-yl)-2-tert-butoxyacetate | |
|---|---|
| MS (M + H)$^+$ Calcd. | 390 |
| MS (M + H)$^+$ Observ. | 390 |
| Retention Time | 2.217 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

EXAMPLE 35

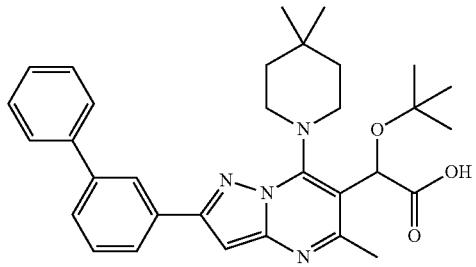 [SMILES: Cc1nc2cc(-c3cccc(-c4ccccc4)c3)nn2c(N2CCC(C)(C)CC2)c1C(OC(C)(C)C)C(=O)O]

| 2-(2-([1,1'-Biphenyl]-3-yl)-7-(4,4-dimethylpiperidin-1-yl)-5-methylpyrazolo[1,5-a]pyrimidin-6-yl)-2-(tert-butoxy)acetic acid | |
|---|---|
| MS (M + H)$^+$ Calcd. | 527 |
| MS (M + H)$^+$ Observ. | 527 |
| Retention Time | 2.633 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, DMSO-d$_6$) δ 8.36 (t, J=1.7 Hz, 1H), 8.04 (d, J=7.6 Hz, 1H), 7.77 (dd, J=8.1, 1.1 Hz, 2H), 7.74-7.70 (m, 1H), 7.61 (t, J=7.6 Hz, 1H), 7.56-7.49 (m, 2H), 7.46-7.38 (m, 1H), 7.11 (s, 1H), 5.63 (s., 1H), 3.36 (br. s., 4H), 2.54 (s, 3H), 1.65 (br. s., 2H), 1.51 (br. s., 2H), 1.23 (s, 9H), 1.01 (br. s., 6H).

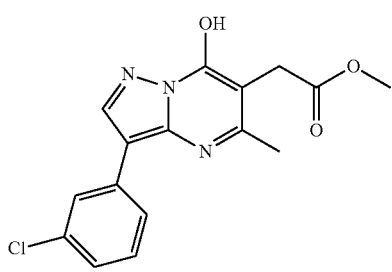 [SMILES: COC(=O)Cc1c(C)nc2c(-c3cccc(Cl)c3)cnn2c1O]

Methyl 2(3-(3-chlorophenyl)-(7-hydroxy-5-methylpyrazolo[1,5-a]pyrimidin-6-yl)acetate To a solution of 4-(3-chlorophenyl)-1H-pyrazol-5-amine (1 g, 5.2 mmol) and dimethyl 2-acetylsuccinate (2.92 g, 15.5 mmol) in xylene (100 mL) was added p-toluenesulfonic acid monohydrate (10 mg, 0.052 mmol). The reaction mixture was heated at reflux under a Dean-Stark trap for 2 hrs. The solid was filtered and washed by hexanes to afford (1.3 g, 76%) of the title compound. $^1$H-NMR (500 MHz, DMSO-$d_6$) δ 2.39 (s, 3H), 3.59 (s, 2H), 3.63 (s, 3H), 7.37 (s, 1H), 7.48 (s, 1H), 7.54 (s, 1H), 7.56 (s, 1H), 7.64 (d, 1H), 8.19 (s, 1H), 11.94 (s, 1H).

| Methyl2(3-(3-chlorophenyl)-(7-hydroxy-5-methylpyrazolo[1,5-a]pyrimidin-6-yl)acetate | |
|---|---|
| MS (M + H)$^+$ Calcd. | 332 |
| MS (M + H)$^+$ Observ. | 332 |
| Retention Time | 1.81 min |
| LC Condition | |
| Solvent A | 10% Methanol: 90% Water: 0.1% TFA |
| Solvent B | 90% Methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

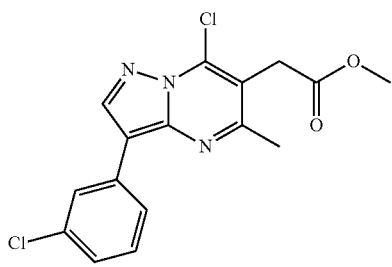 [SMILES: COC(=O)Cc1c(C)nc2c(-c3cccc(Cl)c3)cnn2c1Cl]

Methyl 2-(7-chloro-3-(3-chlorophenyl)-5-methylpyrazolo[1,5-a]pyrimidin-6-yl)acetate To methyl 2-(3-(3-chlorophenyl)-(7-hydroxy-5-methylpyrazolo[1,5-a]pyrimidin-6-yl)acetate (1.3 g, 3.92 mmol) was added POCl$_3$ (4 mL). The reaction mixture was heated at reflux for 1 h. After cooling, the reaction mixture was added drop-wise to ice-water. A brown solid precipitated. The solid were filtered and washed with water, then dissolved in ethyl acetate. The organic solution was washed with saturated NaHCO$_3$ and dried over sodium sulfate. The solvent was evaporated to give the title compound (1.3 g, 90%). Used as is in the next step.

| Methyl 2-(7-chloro-3-(3-chlorophenyl)-5-methylpyrazolo[1,5-a]pyrimidin-6-yl)acetate. | |
|---|---|
| MS (M + H)$^+$ Calcd. | 351 |
| MS (M + H)$^+$ Observ. | 351 |
| Retention Time | 2.1 min |
| LC Condition | |
| Solvent A | 10% Methanol: 90% Water: 0.1% TFA |
| Solvent B | 90% Methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

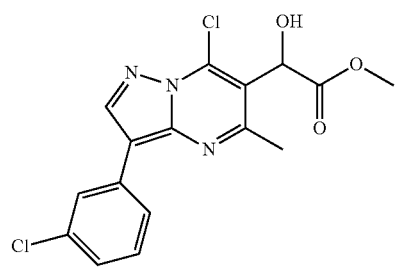 [SMILES: COC(=O)C(O)c1c(C)nc2c(-c3cccc(Cl)c3)cnn2c1Cl]

Methyl 2-(7-chloro-3-(3-chlorophenyl)-5-methyl-3-phenylpyrazolo[1,5-a]pyrimidin-6-yl)-2-hydroxyacetate To a stirred solution of KHMDS (0.5 M in toluene, 7.4 mL) in THF (20 mL) at −78° C. was added a solution of methyl 2-(7-chloro-3-(3-chlorophenyl)-5-methylpyrazolo[1,5-a]pyrimidin-6-yl)acetate (1.3 g, 3.7 mmol) in THF (20 mL) over 20 mins. The reaction mixture was stirred at −78° C. for 30 min. A solution of 3-phenyl-2-(phenylsulfonyl)-1,2-oxaziridine (1.16 g, 4.45 mmol) in THF (20 mL) was added over 10 min and the resulted reaction mixture was stirred for an additional 30 min at −78° C. The reaction mixture was quenched with saturated NH$_4$Cl aqueous solution (2 mL). The mixture was allowed to warm up to room temperature and diluted with EtOAc (100 mL). The organic phase was washed with water and brine and dried with sodium sulfate. The solvent was evaporated. Purification by silica gel chromatography provided the title compound (0.4 mg, 30%). Used as is in the next step.

| Methyl 2-(7-chloro-3-(3-chlorophenyl)-5-methyl-3-phenylpyrazolo[1,5-a]pyrimidin-6-yl)-2-hydroxyacetate. | |
|---|---|
| MS (M + H)$^+$ Calcd. | 366 |
| MS (M + H)$^+$ Observ. | 366 |
| Retention Time | 2.15 min |

-continued

Methyl 2-(7-chloro-3-(3-chlorophenyl)-5-methyl-3-phenylpyrazolo[1,5-a]pyrimidin-6-yl)-2-hydroxyacetate.

| LC Condition | |
| --- | --- |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

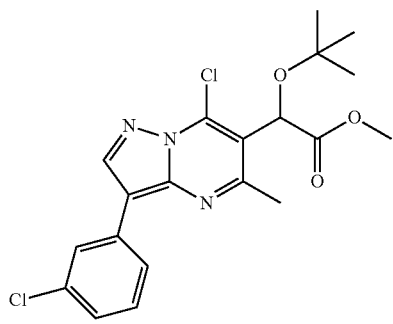 [SMILES: COC(=O)C(OC(C)(C)C)c1c(C)nc2c(-c3cccc(Cl)c3)cnn2c1Cl]

Methyl 2-tert-butoxy-2-(7-chloro-3-(3-chlorophenyl)-5-methylpyrazolo[1,5-a]pyrimidin-6-yl)acetate To a suspension of methyl 2-(7-chloro-3-(3-chlorophenyl)-5-methyl-3-phenylpyrazolo[1,5-a]pyrimidin-6-yl)-2-hydroxyacetate (400 mg, 1.09 mmol) in tert-butyl acetate (5 mL) at room temperature was added $CH_2Cl_2$ (15 mL) followed by perchloric acid (165 mg, 1.6 mmol). The reaction mixture was stirred for 2 h at room temperature. The reaction mixture was diluted with ethyl acetate (15 mL). The organic phase was washed with saturated $NaHCO_3$ (2×10 mL), followed by water (1×10 mL) and dried over sodium sulfate. The solvent was evaporated. Purification by silica gel chromatography provided the title compound (300 mg, 65%). Used as is in the next step.

Methyl 2-tert-butoxy-2-(7-chloro-3-(3chlorophenyl)-5-methylpyrazolo[1,5-a]pyrimidin-6-yl)acetate

| | |
| --- | --- |
| MS (M + H)$^+$ Calcd. | 422 |
| MS (M + H)$^+$ Observ. | 422 |
| Retention Time | 2.45 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

EXAMPLE 36

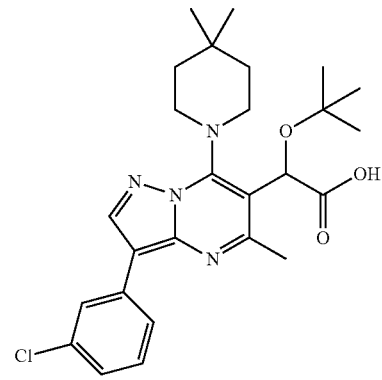 [SMILES: Cc1nc2c(-c3cccc(Cl)c3)cnn2c(N2CCC(C)(C)CC2)c1C(OC(C)(C)C)C(=O)O]

2-(tert-butoxy)-2-(3-(3-chlorophenyl)-7-(4,4-dimethylpiperidin-1-yl)-5-pyrazolo[1,5a]pyrimidin-6-yl) acetic acid To a solution of methyl 2-tert-butoxy-2-(7-chloro-3-(3-chlorophenyl)-5-methylpyrazolo[1,5-a]pyrimidin-6-yl)acetate (25 mg, 0.06 mmol) and 4,4-dimethylpiperidine.HCl (6.7 mg, 0.06 mmol) in NMP (1 mL) was added DIEA (23 mg, 0.18 mmol) and the mixture was heated at 50° C. for 2 h. Then, 1N LiOH (0.272 mL, 0.272 mmol) was added to the reaction mixture and the contents were heated at 50° C. for 2 h. The reaction mixture was then filtered and purified by prep-HPLC to afford 2-(tert-butoxy)-2-(3-(3-chlorophenyl)-7-(4,4-dimethylpiperidin-1-yl)-5-pyrazolo[1,5a]pyrimidin-6-yl)acetic acid (11 mg, 0.022 mmol, 38% yield) as white solid. $^1$H NMR (500 MHz, DMSO-d$_6$) δ 1.08 (s, 6H), 1.25 (S, 9H), 1.39-1.72 (m, 6H), 2.63 (s, 3H), 3.35 (br. s., 2H), 5.75 (s, 1H), 7.27 (dt, 1H), 7.46 (t, 1H), 8.13 (d, 1H), 8.25 (t, 1H), 8.76 (s, 1H).

2-(tert-butoxy)-2-(3-(3-chlorophenyl)-7-(4,4-dimethylpiperidin-1-yl)-5-pyrazolo[1,5a]pyrimidin-6-yl)acetic acid

| | |
| --- | --- |
| MS (M + H)$^+$ Calcd. | 485 |
| MS (M + H)$^+$ Observ. | 485 |
| Retention Time | 2.25 min |
| LC Condition | |
| Solvent A | 5% Acetonitrile: 95% water: 0.1% TFA |
| Solvent B | 95% acetonitrile: 5% water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:water:0.1% TFA |
| Column | Phenomenex LUNA C18, 30 × 2, 3u |

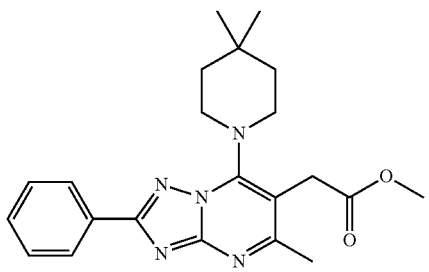 [SMILES: COC(=O)Cc1c(C)nc2nc(-c3ccccc3)nn2c1N1CCC(C)(C)CC1]

Methyl 2-(7-(4,4-dimethylpiperidin-1-yl)-5-methyl-2-phenyl-[1,2,4]-triazolo[1,5-a]pyrimidin-6-yl)acetate To a solution of methyl 2-(7-chloro-5-methyl-2-phenyl-[1,2,4]triazolo[1,5-a]pyrimidin-6-yl)acetate (100 mg, 0.316 mmol) and 4,4-dimethylpiperidine, HCl (47.3 mg, 0.316 mmol) in NMP (Volume: 3 mL) was added DIEA (0.220 mL, 1.263 mmol). The resulting mixture was stirred at r.t for 3 hrs. then purified by Pre-HPLC to afford methyl 2-(7-(4,4-dimethylpiperidin-1-yl)-5-methyl-2-phenyl-[1,2,4]triazolo[1,5-a]pyrimidin-6-yl)acetate (108 mg, 0.269 mmol, 85% yield). $^1$H-NMR (500 MHz, CDCl$_3$) δ 1.14 (6 H, s), 1.68 (2 H, t), 2.63 (3 H, s), 3.62 (2 H, t), 3.82 (3 H, s), 7.55-7.57 (3 H, m), 8.24-8.26 (2 H, m).

| methyl 2-(7-(4,4-dimethylpiperidin-1-yl)-5-methyl-2-phenyl-[1,2,4]triazolo[1,5-a]pyrimidin-6-yl)acetate | |
|---|---|
| MS (M + H)$^+$ Calcd. | 393.5 |
| MS (M + H)$^+$ Observ. | 394.2 |
| Retention Time | 4.11 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 50 mm 3 um |

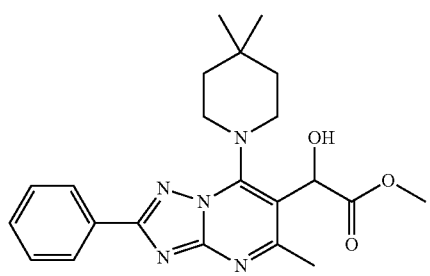 [SMILES: COC(=O)C(O)c1c(C)nc2nc(-c3ccccc3)nn2c1N1CCC(C)(C)CC1]

Methyl 2-(7-(4,4-dimethylpiperidin-1-yl)-5-methyl-2-phenyl-[1,2,4]-triazolo[1,5-a]pyrimidin-6-yl)-2-hydroxyacetate To a solution of methyl 2-(7-(4,4-dimethylpiperidin-1-yl)-5-methyl-2-phenyl[1,2,4]triazolo[1,5-a]pyrimidin-6-yl)acetate (106 mg, 0.269 mmol) in anhydrous THF (5 ml) at −78° C. was added dropwise KHMDS (0.808 mL, 0.404 mmol) in toluene. Reaction mixture was stirred at −78° C. for 30 min and to this was added dropwise 3-phenyl-2-(phenylsulfonyl)-1,2-oxaziridine (106 mg, 0.404 mmol) in THF (2 mL) and the contents were stirred at −78° C. for 30 min and allowed slowly to warm to room temperature, then quenched with a drop of saturated ammonium chloride solution. Evaporated to remove the solvent. Purified by prep HPLC to afford methyl 2-(7-(4,4-dimethylpiperidin-1-yl)-5-methyl-2-phenyl-[1,2,4]triazolo[1,5-a]pyrimidin-6-yl)-2-hydroxyacetate (56 mg, 0.134 mmol, 49.8% yield) as white solid. $^1$H-NMR (500 MHz, CDCl$_3$) δ 1.15 (6 H, s), 1.69-1.75 (4 H, m), 2.62 (3 H, s), 3.77-3.79 (2 H, m), 3.81-3.83 (2 H, m), 3.85 (3 H, s), 5.49 (1 H, s), 7.56-7.60 (3 H, m), 8.20-8.22 (2 H, m).

| Methyl 2-(7-(4,4-dimethylpiperidin-1-yl)-5-methyl-2-phenyl-[1,2,4]triazolo[1,5-a]pyrimidin-6-yl)-2-hydroxyacetate | |
|---|---|
| MS (M + H)$^+$ Calcd. | 409.5 |
| MS (M + H)$^+$ Observ. | 410.2 |
| Retention Time | 4.08 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 50 mm 3 um |

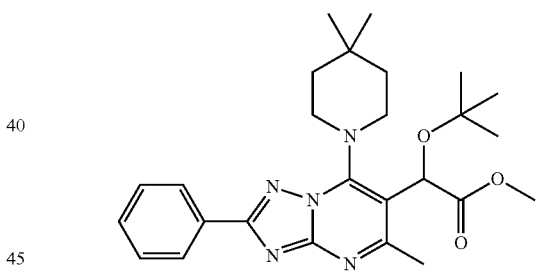

Methyl 2-tert-butoxy-2-(7-(4,4-dimethylpiperidin-1-yl)-5-methyl-2-phenyl-[1,2,4]triazolo[1,5-a]pyrimidin-6-yl)acetate To a solution of methyl 2-(7-(4,4-dimethylpiperidin-1-yl)-5-methyl-2-phenyl-[1,2,4]triazolo[1,5-a]pyrimidin-6-yl)-2-hydroxyacetate (56 mg, 0.137 mmol) in t-butylacetate (2 ml, 0.137 mmol) was added anhydrous DCM (Volume: 2 ml) followed by perchloric acid (0.012 ml, 0.205 mmol). The resulting mixture was stirred at r.t for 1 h. Diluted with EtOAc, washed with sat'd NaHCO$_3$. The organic phase was dried and evaporated to an oil, which was purified by Pre-HPLC to afford methyl 2-tert-butoxy-2-(7-(4,4-dimethylpiperidin-1-yl)-5-methyl-2-phenyl-[1,2,4]triazolo[1,5-a]pyrimidin-6-yl)acetate (25 mg, 0.053 mmol, 38.5% yield). $^1$H-NMR (400 MHz, CDCl3) δ 1.16 (6H, s), 1.26 (9H, s), 1.58-1.60 (2H, m), 1.69-1.73 (2H, m), 2.69 (3H, s), 3.77 (3 H, s), 5.87 (1 H, s), 7.49-7.53 (3 H, m), 8.35-8.37 (2 H, m).

| Methyl 2-tert-butoxy-2-(7-(3,4-dimethylphenyl)-5-methyl-2-phenylpyrazolo[1,5-a]pyrimidin-6-yl)acetate, TFA salt. | |
|---|---|
| MS (M + H)+ Calcd. | 465.6 |
| MS (M + H)+ Observ. | 466.1 |
| Retention Time | 4.71min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 50 mm 3 um |

EXAMPLE 37

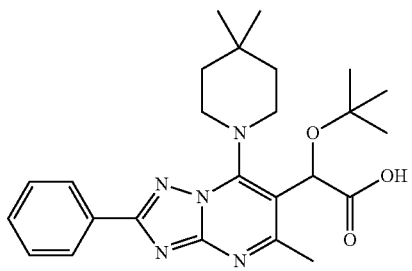

2-tert-Butoxy-2-(7-(4,4-dimethylpiperidin-1-yl)-5-methyl-2-phenyl-[1,2,4]triazolo[1,5-a]pyrimidin-6-yl)acetic acid To a solution of methyl 2-tert-butoxy-2-(7-(4,4-dimethylpiperidin-1-yl)-5-methyl-2-phenyl-[1,2,4]triazolo[1,5-a]pyrimidin-6-yl)acetate (25 mg, 0.054 mmol) in dioxane (0.8 ml) was added sodium hydroxide (0.8 mL, 0.8 mmol). The resulting mixture was warmed to 50° C. and stirred for 4 h. then filtered and purified by Pre-HPLC to afford 2-tert-butoxy-2-(7-(4,4-dimethylpiperidin-1-yl)-5-methyl-2-phenyl-[1,2,4]triazolo[1,5-a]pyrimidin-6-yl)acetic acid (18 mg, 0.039 mmol, 72.8% yield). $^1$H-NMR (400 MHz, CDCl3) δ 1.17 (6 H, s), 1.30 (9 H, s), 1.57-1.61 (2 H, m), 1.70-1.72 (2 H, m), 2.70 (3H, s), 5.83 (1 H, s), 7.49-7.54 (3 H, m), 8.35-8.37 (2 H, m).

| 2-tert-Butoxy-2-(7-(3,4-dimethylphenyl)-5-methyl-2-phenylpyrazolo[1,5-a]pyrimidin-6-yl)acetic acid, TFA salt. | |
|---|---|
| MS (M + H)+ Calcd. | 451.6 |
| MS (M + H)+ Observ. | 452.4 |
| Retention Time | 3.35min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |

| 2-tert-Butoxy-2-(7-(3,4-dimethylphenyl)-5-methyl-2-phenylpyrazolo[1,5-a]pyrimidin-6-yl)acetic acid, TFA salt. | |
|---|---|
| Wavelength | 220 |
| Solvent Pair | methanol:Water:TFA |
| Column | Phenomenex Luna 2.0 × 50 mm 3 um |

The following Example 38-41 were prepared in a similar way as Example 37.

EXAMPLE 38

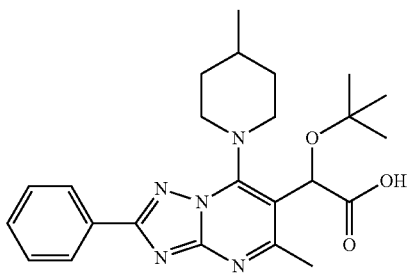 [SMILES: Cc1nc2nc(-c3ccccc3)nn2c(N2CCC(C)CC2)c1C(OC(C)(C)C)C(=O)O]

| 2-tert-Butoxy-2-(5-methyl-7-(4-methylpiperidin-1-yl)-2-phenyl-[1,2,4]triazolo[1,5-a]pyrimidin-6-yl)acetic acid | |
|---|---|
| MS (M + H)+ Calcd. | 437.5 |
| MS (M + H)+ Observ. | 438.0 |
| Retention Time | 4.45min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 50 mm 3 um |

$^1$H-NMR (400 MHz, CDCl3) δ 1.10-1.11 (3 H, m), 1.23 (9 H, s), 1.79-1.84 (1 H, m), 1.87-1.91 (3 H, m), 2.71 (3 H, s), 3.98-4.22 (1 H, m), 4.20-4.22 (1 H, m), 5.46 (1 H, s), 7.48-7.55 (3 H, m), 8.24-8.26 (2 H, m).

EXAMPLE 39

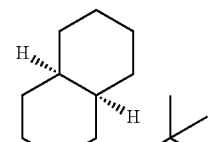
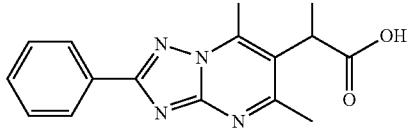

| 2-(tert-Butoxy)-2-(5-methyl-7-((4aR,8aR)-octahydroisoquinolin-2(1H)-yl)-2-phenyl-[1,2,4]triazolo[1,5-a]pyrimidin-6-yl)acetic acid | |
|---|---|
| MS (M + H)+ Calcd. | 477.3 |
| MS (M + H)+ Observ. | 478.3 |
| Retention Time | 2.51 min |
| LC Condition | |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H-NMR (400 MHz, CD3OD) δ ppm 1.25 (9 H, s), 1.27-1.40 (3 H, m), 1.66-1.82 (6 H, m), 2.05-2.13 (2 H, m), 2.68 (3H, s), 3.36-3.38 (1 H, m), 3.43-3.44 (2 H, m), 4.14-4.16 (1 H, m), 5.58 (1 H, s), 7.56-7.59 (3 H, m), 8.23-8.27 (2 H, m).

EXAMPLE 40

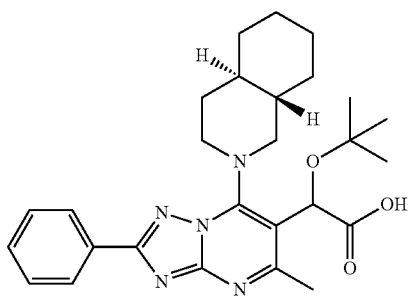 [SMILES: Cc1nc2nc(-c3ccccc3)nn2c(N2CC[C@H]3CCCC[C@@H]3C2)c1C(OC(C)(C)C)C(=O)O]

| 2-(tert-Butoxy)-2-(5-methyl-7-((4aR,8aS)-octahydroisoquinolin-2(1H)-yl)-2-phenyl-[1,2,4]triazolo[1,5-a]pyrimidin-6-yl)acetic acid | |
|---|---|
| MS (M + H)+ Calcd. | 478.3 |
| MS (M + H)+ Observ. | 478.6 |
| Retention Time | 2.51 min |
| LC Condition | |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2.1 min |
| Flow Rate | 1 mL/min |
| Wavelength | 220 |
| Solvent Pair | methanol:Water:TFA |
| Column | Phenomenex Luna 2.0 × 30 mm 3 um |

$^1$H-NMR (400 MHz, CD3OD) δ 1.14-1.24 (2H, m), 1.27 (9 H, s), 1.39-1.42 (4H, m), 1.51-1.52 (2H, m), 1.82-1.87 (4H, m), 2.71 (3H, s), 3.50-3.51 (1H, m), 3.62-3.63 (1H, m), 4.14-4.16 (1H, m), 5.66 (1H, s), 7.56-7.58 (3H, m), 8.22-8.24 (2H, m).

EXAMPLE 41

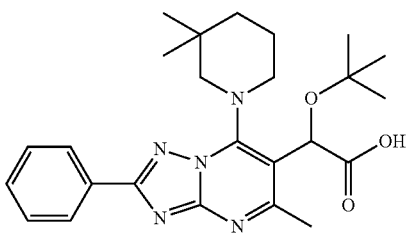 [SMILES: Cc1nc2nc(-c3ccccc3)nn2c(N2CCCC(C)(C)C2)c1C(OC(C)(C)C)C(=O)O]

| 2-(tert-Butoxy)-2-(7-(3,3-dimethylpiperidin-1-yl)-5-methyl-2-phenyl-[1,2,4]triazolo[1,5-a]pyrimidin-6-yl)acetic acid | |
|---|---|
| MS (M + H)+ Calcd. | 452.3 |
| MS (M + H)+ Observ. | 452.3 |
| Retention Time | 2.39 min |
| LC Condition | |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2.1 min |
| Flow Rate | 1 mL/min |
| Wavelength | 220 |
| Solvent Pair | methanol:Water:TFA |
| Column | Phenomenex Luna 2.0 × 30 mm 3 um |

$^1$H-NMR (400 MHz, CD3OD) δ 1.14-1.24 (2H, m), 1.27 (9 H, s), 1.39-1.42 (4H, m), 1.51-1.52 (2H, m), 1.82-1.87 (4H, m), 2.71 (3H, s), 3.50-3.51 (1H, m), 3.62-3.63 (1H, m), 4.14-4.16 (1H, m), 5.66 (1H, s), 7.56-7.58 (3H, m), 8.22-8.24 (2H, m).

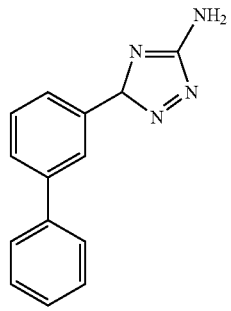 [SMILES: NC1=NC(c2cccc(-c3ccccc3)c2)N=N1]

3-([1,1'-biphenyl]-3-yl)-3H-1,2,4-triazol-5-amine

To a mixture of hydrazinecarboximidamide, HCl (4.17 g, 37.7 mmol) in MeOH (50 mL) was added sodium methanolate (8.63 mL, 37.7 mmol) dropwise at 0° C., then ethyl [1,1'-biphenyl]-3-carboxylate (2.134 g, 9.43 mmol) was added at 0° C. Stirred at the same temperature for 10 min., warmed to r.t. for 10 min., then heated to reflux for 24 hrs. 20 ml of water added, concentrated to remove the MeOH, the aqueous soln. was neutralized with 6N HCl to PH=3~4 (orange color to light yellow color). Solid was precipitated. Filtered and washed with water to leave 3-([1,1'-biphenyl]-3-yl)-3H-1,2,4-triazol-5-amine (2.32 g, 5.89 mmol, 62.5% yield) as off-white solid.

$^1$H-NMR (500 MHz, CD$_3$OD) δ 7.41-7.44 (1H, m), 7.49-7.52 (2H, m), 7.61-7.64 (1H, m), 7.71-7.73 (2H, m), 7.80-7.82 (1H, m), 7.83-7.88 (1H, m), 8.18 (1 H, s).

| 3-([1,1'-biphenyl]-3-yl)-3H-1,2,4-triazol-5-amine | |
|---|---|
| MS (M + H)$^+$ Calcd. | 237.1 |
| MS (M + H)$^+$ Observ. | 237.1 |
| Retention Time | 1.89 min . . . |
| LC Condition | |
| Solvent A | 5% Acetonitrile:95% Water:10 mM NH4OAc |
| Solvent B | 95% Acetonitrile:5% Water:10 mM NH4OAc |
| Start % B | 0 |
| Final % B | 100 |
| Gradient Time | 2 min |
| Flow Rate | 1 mL/min |
| Wavelength | 220 |
| Solvent Pair | Acetonitrile:Water:NH4OAc |
| Column | Phenomenex Luna 2.0 × 30 mm 3 um |

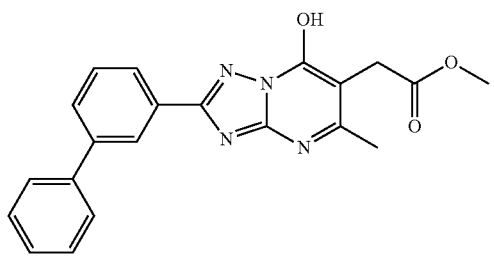 [SMILES: COC(=O)Cc1c(C)nc2nc(-c3cccc(-c4ccccc4)c3)nn2c1Cl]

Methyl 2-(2-([1,1'-biphenyl]-3-yl)-7-hydroxy-5-methyl-[1,2,4]-triazolo[1,5-a]pyrimidin-6-yl)acetate In a 100 ml RBF, equipped with a Dean-Stark trap (filled with molecular sieves), was added 5-([1,1'-biphenyl]-3-yl)-3H-1,2,4-triazol-3-amine (1.133 g, 4.80 mmol), dimethyl 2-acetylsuccinate (2.334 mL, 14.39 mmol) followed by Xylene (50 mL) and Ts-OH (9.12 mg, 0.048 mmol). The reaction was heated at reflux for 5 hrs. Filtered and washed by hexanes to collect the off-white solid, which was used directly for the next step. $^1$H-NMR (500 MHz, CDCl3) δ 2.26 (3H, s), 3.65 (2H, s), 3.72 (3H, s), 7.35-7.36 (1H, m), 7.44-7.46 (2H, m), 7.47-7.48 (1H, m), 7.64-7.66 (2H, m), 7.73-7.75 (1H, m), 8.13-8.15 (1H, m), 8.43 (1 H, s).

| Methyl 2-(2-([1,1'-biphenyl]-3-yl)-7-hydroxy-5-methyl-[1,2,4]triazolo[1,5-a]pyrimidin-6-yl)acetate | |
|---|---|
| MS (M + H)$^+$ Calcd. | 375.4 |
| MS (M + H)$^+$ Observ. | 375.2 |
| Retention Time | 2.1 min . . . |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

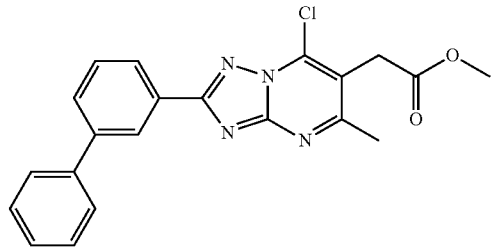

Methyl 2-(2-([1,1'-biphenyl]-3-yl)-7-chloro-5-methyl-[1,2,4]triazolo[1,5-a]pyrimidin-6-yl)acetate A suspension of methyl 2-(2-([1,1'-biphenyl]-3-yl)-7-hydroxy-5-methyl-[1,2,4]triazolo[1,5-a]pyrimidin-6-yl)acetate (748 mg, 1.998 mmol) in phosphoryl trichloride (15 ml, 1.998 mmol) was heated to reflux for 16 hrs. Concentrated to remove most of phosphoryl chloride to leave an oil, which was carefully neutralized w/sat'd NaHCO3 to PH=~7. The precipitates was filtered and washed w/water, dried in vacuo to afford methyl 2-(2-([1,1'-biphenyl]-3-yl)-7-chloro-5-methyl-[1,2,4]triazolo[1,5-a]pyrimidin-6-yl)acetate (720 mg, 1.741 mmol, 87% yield). The crude was used for the next reaction directly. $^1$H-NMR (500 MHz, CDCl3) δ ppm 2.75 (3H, s), 3.81 (3H, s), 3.96 (2H, s), 7.43-7.44 (1H, m), 7.49-7.52 (2H, m), 7.62-7.63 (1H, m), 7.74-7.78 (3H, m), 8.36-8.38 (1H, m), 8.65 (1 H, s).

| Methyl 2-(2-([1,1'-biphenyl]-3-yl)-7-hydroxy-5-methyl-[1,2,4]triazolo[1,5-a]pyrimidin-6-yl)acetate | |
|---|---|
| MS (M + H)$^+$ Calcd. | 393.1 |
| MS (M + H)$^+$ Observ. | 393.1 |
| Retention Time | 2.21 min . . . |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

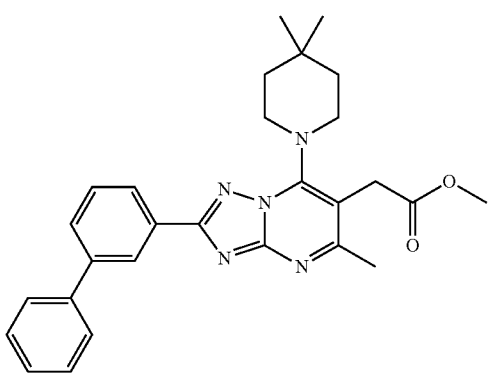 [SMILES: COC(=O)Cc1c(C)nc2nc(-c3cccc(-c4ccccc4)c3)nn2c1N1CCC(C)(C)CC1]

Methyl 2-(2-([1,1'-biphenyl]-3-yl)-7-(4,4-dimethylpiperidin-1-yl)-5-methyl-[1,2,4]-triazolo[1,5-a]pyrimidin-6-yl)acetate was similarly prepared as previously described above for Methyl 2-(7-(4,4-dimethylpiperidin-1-yl)-5-methyl-2-phenyl-[1,2,4]triazolo[1,5-a]pyrimidin-6-yl)acetate.
$^1$H-NMR (500 MHz, CDCl3) δ 1.14 (6H, s), 1.64 (4H, t, J=5.6 Hz), 2.60 (3H, s), 3.54-3.55 (4H, m), 3.80 (3H, s), 3.83 (2H, s), 7.41-7.42 (1H, m), 7.48-7.51 (2H, m), 7.57-7.58 (1H, m), 7.73-7.75 (3H, m), 8.33-8.34 (1H, m), 8.65 (1 H, s).

| Methyl 2-(2-([1,1'-biphenyl]-3-yl)-7-hydroxy-5-methyl-[1,2,4]triazolo[1,5-a]pyrimidin-6-yl)acetate | |
|---|---|
| MS (M + H)$^+$ Calcd. | 470.6 |
| MS (M + H)$^+$ Observ. | 470.4 |
| Retention Time | 2.47 min . . . |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

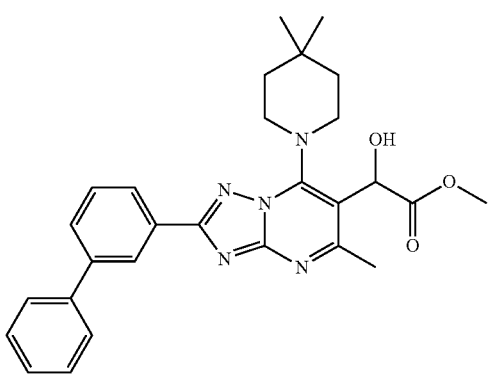 [SMILES: COC(=O)C(O)c1c(C)nc2nc(-c3cccc(-c4ccccc4)c3)nn2c1N1CCC(C)(C)CC1]

Methyl 2-(2-([1,1'-biphenyl]-3-yl)-7-(4,4-dimethylpiperidin-1-yl)-5-methyl-[1,2,4]-triazolo[1,5-a]pyrimidin-6-yl)-2-hydroxyacetate was prepared by the similar way as previously described above for Methyl 2-(7-(4,4-dimethylpiperidin-1-yl)-5-methyl-2-phenyl-[1,2,4]triazolo[1,5-a]pyrimidin-6-yl)-2-hydroxyacetate. $^1$H-NMR (500 MHz, CDCl3) δ 1.16 (6H, s), 1.64 (4H, t, J=5.6 Hz), 2.70 (3H, s), 3.64-3.66 (4H, m), 3.84 (3H, s), 5.58 (1H, s), 7.43-7.45 (1H, m), 7.49-7.51 (2H, m), 7.59-7.61 (1H, m), 7.73-7.75 (3H, m), 8.32-8.33 (1H, m), 8.65 (1 H, s).

| Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-hydroxyacetate | |
|---|---|
| MS (M + H)$^+$ Calcd. | 486.3 |
| MS (M + H)$^+$ Observ. | 486.4 |
| Retention Time | 2.0 min . . . |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

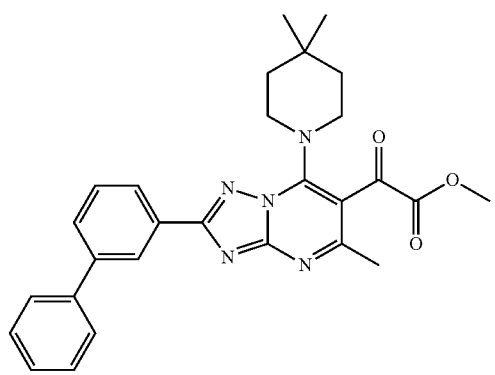 [SMILES: COC(=O)C(=O)c1c(C)nc2nc(-c3cccc(-c4ccccc4)c3)nn2c1N1CCC(C)(C)CC1]

Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-oxoacetate To a soln. of methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-hydroxyacetate (73 mg, 0.150 mmol) in CH2Cl2 (5 mL) was added Dess-MartinPeriodinane (70.1 mg, 0.165 mmol) and the resulting mixture was stirred at room temp for 1 hr and then diluted with ethyl 5 mL) and washed with sat. NaHCO3 solution (5 mL), dried (Na2SO4), filtered and concentrated and purified by Biotage (90 g, eluted from 3-32% EtOAc/Hexane) to afford methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-oxoacetate (61 mg, 0.124 mmol, 82% yield).

| Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-oxoacetate | |
|---|---|
| MS (M + H)$^+$ Calcd. | 484.6 |
| MS (M + H)$^+$ Observ. | 484.4 |
| Retention Time | 2.1 min . . . |
| LC Condition | |
| Solvent A | 10% methanol:90% Water:0.1% TFA |
| Solvent B | 90% methanol:10% Water:0.1% TFA |
| Start % B | 0 |

| Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-oxoacetate | |
| --- | --- |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

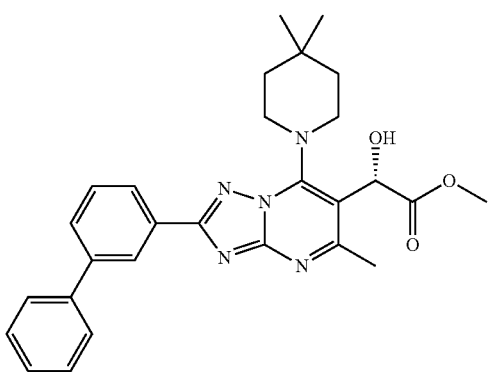 [SMILES: COC(=O)[C@@H](O)c1c(C)nc2nc(-c3cccc(-c4ccccc4)c3)nn2c1N1CCC(C)(C)CC1]

(S)-Methyl 2-(2-([1,1'-biphenyl]-3-yl)-7-(4,4-dimethylpiperidin-1-yl)-5-methyl-[1,2,4]triazolo[1,5-c]pyrimidin-6-yl)-2-hydroxyacetate To a stirred yellow solution of methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-oxoacetate (61 mg, 0.126 mmol) in anhydrous Toluene (6 mL) was added 1.1M (R)-1-methyl-3,3-diphenylhexahydropyrrolo[1,2-c][1,3,2]oxazaborole/toluene (0.046 mL, 0.050 mmol). The mixture was cooled to −35° C. and a solution of 1M catechoborane/THF (0.177 mL, 0.177 mmol) was added over 10 min. After 30 min, the reaction mixture was slowly warmed to −15° C. and stirred for additional 2 h. and diluted with EtOAc (100 mL) and sat. Na₂CO₃ (50 mL). The mixture was stirred vigorously for 30 min, and the organic phase washed with sat Na₂CO₃ (2×50 mL), dried (Na2SO4), filtered, concentrated and the residue was purified by Biotage (5-70% EtOAc/hexane) to afford desired (S)-methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-hydroxyacetate (59 mg, 0.115 mmol, 92% yield).

| (S)-Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-hydroxyacetate | |
| --- | --- |
| MS (M + H)⁺ Calcd. | 486.6 |
| MS (M + H)⁺ Observ. | 486.4 |
| Retention Time | 2.42 min... |
| LC Condition | |
| Solvent A | 5% Acetonitrile:95% Water:10 mM NH4OAc |
| Solvent B | 95% Acetonitrile:5% Water:10 mM NH4OAc |
| Start % B | 0 |
| Final % B | 100 |
| Gradient Time | 2 min |

| (S)-Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-hydroxyacetate | |
| --- | --- |
| Flow Rate | 1 mL/min |
| Wavelength | 220 |
| Solvent Pair | acetonitrile:Water:NH4OAc |
| Column | Phenomenex Luna 2.0 × 30 mm 3 um |

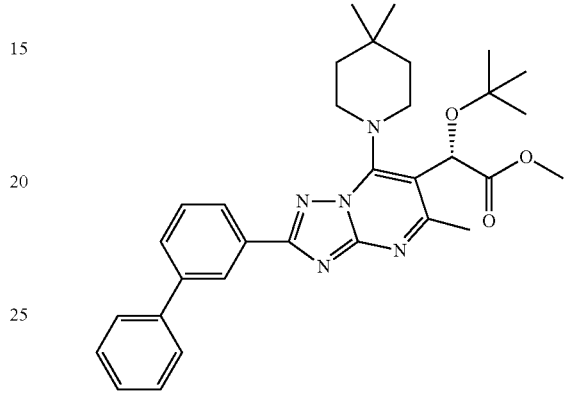

(S)-Methyl 2-(2-([1,1'-biphenyl]-3-yl)-7-(4,4-dimethylpiperidin-1-yl)-5-methyl-[1,2,4]triazolo[1,5-a]pyrimidin-6-yl)-2-(tert-butoxy)acetate was prepared in a similar way as 2-tert-butoxy-2-(7-(4,4-dimethylpiperidin-1-yl)-5-methyl-2-phenyl-[1,2,4]triazolo[1,5-a]pyrimidin-6-yl)acetic acid. The crude product was directly used for the next reaction without purification.

EXAMPLE 42

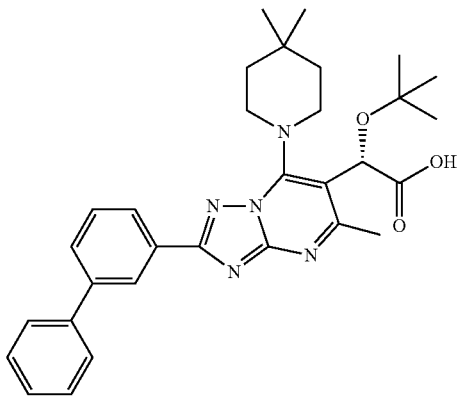 [SMILES: Cc1nc2nc(-c3cccc(-c4ccccc4)c3)nn2c(N2CCC(C)(C)CC2)c1[C@H](OC(C)(C)C)C(=O)O]

(S)-2-(2-([1,1'-Biphenyl]-3-yl)-7-(4,4-dimethylpiperidin-1-yl)-5-methyl-[1,2,4]triazolo[1,5-a]pyrimidin-6-yl)-2-(tert-butoxy)acetic acid was prepared in a similar way as Example 37. ¹H-NMR (500 MHz, CDCl3) δ 1.18 (6H, s), 1.28 (9H, s), 1.59-1.62 (2H, m), 1.81-1.83 (2H, m), 2.73 (3H, s), 3.57-3.59 (2H, m), 3.94-3.95 (2H, m), 5.78 (1H, s), 7.41-7.42 (1H, m), 7.48-7.52 (2H, m), 7.62-7.63 (1H, m), 7.70-7.71 (2H, m), 7.73-7.74 (1H, m), 8.22-8.23 (1H, m), 8.49-8.52 (1 H, m).

| (S)-2-(2-([1,1'-Biphenyl]-3-yl)-7-(4,4-dimethylpiperidin-1-yl)-5-methyl-[1,2,4]triazolo[1,5-a]pyrimidin-6-yl)-2-(tert-butoxy)acetic acid | |
|---|---|
| MS (M + H)+ Calcd. | 528.3 |
| MS (M + H)+ Observ. | 528.5 |
| Retention Time | 2.22 min . . . |
| LC Condition | |
| Solvent A | 5% Acetonitrile:95% Water:10 mM NH4OAc |
| Solvent B | 95% Acetonitrile:5% Water:10 mM NH4OAc |
| Start % B | 0 |
| Final % B | 100 |
| Gradient Time | 2 min |
| Flow Rate | 1 mL/min |
| Wavelength | 220 |
| Solvent Pair | acetonitrile:Water:NH4OAc |
| Column | Phenomenex Luna 2.0 × 30 mm 3 um |

EXAMPLE 43

2 h. Upon completion of hydrolysis, reaction was removed from heat and filtered through a syringe filter. The crude reaction mixture was purified via preparative LC/MS with the following conditions: Column. Waters XBridge C18, 19×200 mm, 5-μμm particles Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B, to provide (S)-2-(2-([1,1'-biphenyl]-3-yl)-7-((1R,5 S)-8-azabicyclo[3.2.1]octan-8-yl)-5-methylpyrazolo[1,5-a]pyrimidin-6-yl)-2-(tert-butoxy)acetic acid (8.9 mg, 17% yield). $^1$H NMR (500 MHz, DMSO-$d_6$) δ 8.23 (s, 1H), 7.97 (d, J=8.2 Hz, 1H), 7.74 (d, J=7.3 Hz, 2H), 7.69 (d, J=7.6 Hz, 1H), 7.61-7.55 (m, 1H), 7.51 (t, J=7.2 Hz, 2H), 7.44-7.38 (m, 1H), 7.00 (s, 1H), 5.45 (br. s., 1H), 5.15 (br. s., 1H), 4.37 (br. s., 1H), 2.86 (br. s., 1H), 2.46 (s, 3H), 2.29 (br. s., 1H), 1.92 (d, J=13.7 Hz, 3H), 1.78 (d, J=12.8 Hz, 2H), 1.69 (d, J=14.0 Hz, 3H), 1.14 (s, 9H). LCMS (ESI, M+1): 525.4.

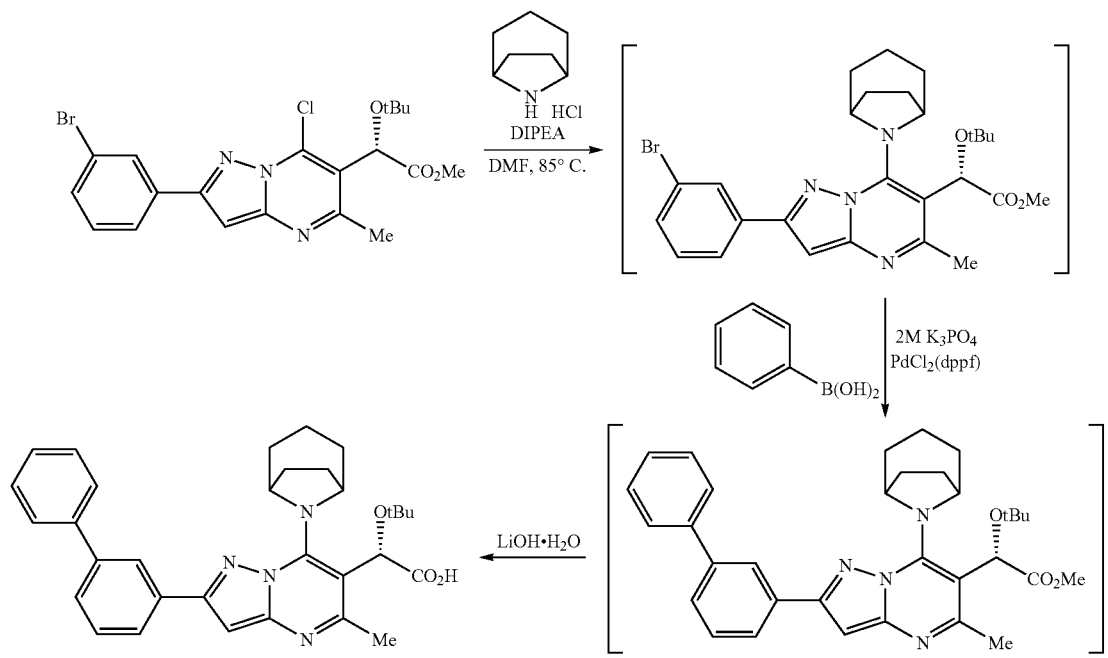

(S)-2-(2-([1,1'-Biphenyl]-3-yl)-7-((1R,5S)-8-azabicyclo[3.2.1]octan-8-yl)-5-methylpyrazolo[1,5-a]pyrimidin-6-yl)-2-(tert-butoxy)acetic acid To a solution of (S)-methyl 2-(2-(3-bromophenyl)-7-chloro-5-methylpyrazolo[1,5-a]pyrimidin-6-yl)-2-(tert-butoxy)acetate (50 mg, 0.107 mmol, 1 equiv) in DMF (0.54 mL) was added 8-azabicyclo[3.2.1]octane hydrochloride (31 mg, 0.214 mmol, 2 equiv) and DIPEA (0.075 mL, 0.428 mmol, 4 equiv). The resulting solution was stirred at 85° C. for 18 h. Complete conversion to pyrimidyl amine was observed. To this solution was then added phenyl boronic acid (30 mg, 0.250 mmol, 2.5 equiv), potassium phosphate, tribasic (0.25 mL of a 2 M aqueous solution, 0.500 mmol, 4.7 equiv), and PdCl$_2$(dppf).CH$_2$Cl$_2$ adduct (8 mg, 0.010 mmol, 0.09 equiv). The mixture was heated at 85° C. for 2 h. Upon completion of the Suzuki reaction, the reaction temperature was lowered to 60° C. Methanol (1 mL), water (0.3 mL), and LiOH.H$_2$O (24 mg, 1.00 mmol, 9 equiv) added and heating was continued for The following compounds are prepared according to the procedure described above for example XX.

EXAMPLE 44

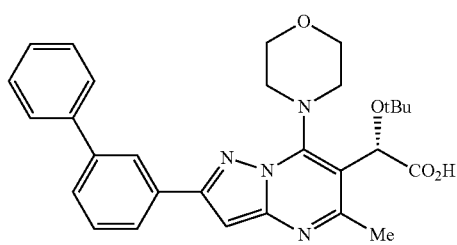 [SMILES: Cc1nc2cc(-c3cccc(-c4ccccc4)c3)nn2c(N2CCOCC2)c1[C@H](OC(C)(C)C)C(=O)O]

(S)-2-(2-([1,1'-Biphenyl]-3-yl)-5-methyl-7-morpholinopyrazolo[1,5-a]pyrimidin-6-yl)-2-(tert-butoxy)acetic acid ¹H NMR (500 MHz, DMSO-d₆) δ 8.25 (s, 1H), 8.05 (d, J=7.6 Hz, 1H), 7.75 (d, J=7.6 Hz, 2H), 7.70 (d, J=7.3 Hz, 1H), 7.60 (t, J=7.6 Hz, 1H), 7.55-7.49 (m, 2H), 7.44-7.39 (m, 1H), 7.16 (s, 1H), 5.77 (s, 1H), 3.92 (br. s., 4H), 3.79 (br. s., 4H), 2.54 (s, 3H), 1.19 (s, 9H). LCMS (ESI, M+1): 501.4.

EXAMPLE 45

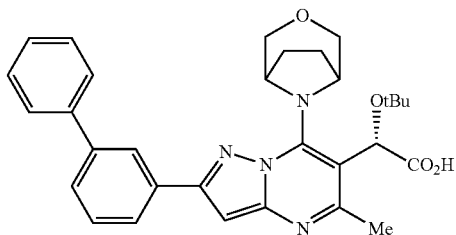 [SMILES: Cc1nc2cc(-c3cccc(-c4ccccc4)c3)nn2c(N2C3CCC2COC3)c1[C@H](OC(C)(C)C)C(=O)O]

(S)-2-(2-([1,1'-Biphenyl]-3-yl)-7-((1R,5S)-3-oxa-8-azabicyclo[3.2.1]octan-8-yl)-5-methylpyrazolo[1,5-a]pyrimidin-6-yl)-2-(tert-butoxy)acetic acid ¹H NMR (500 MHz, DMSO-d₆) δ 8.24 (br. s., 1H), 8.04 (d, J=7.6 Hz, 1H), 7.76 (d, J=7.9 Hz, 2H), 7.71 (d, J=7.9 Hz, 1H), 7.61 (t, J=7.6 Hz, 1H), 7.52 (t, J=7.2 Hz, 2H), 7.44-7.39 (m, 1H), 7.17 (br. s., 1H), 5.90 (s, 1H), 4.50-4.36 (m, 2H), 3.76 (br. s., 2H), 3.08-3.01 (m, 2H), 2.57 (br. s., 3H), 2.17 (br. s., 2H), 1.95 (br. s., 2H), 1.19 (s, 9H). LCMS (ESI, M+1): 527.4.

EXAMPLE 46

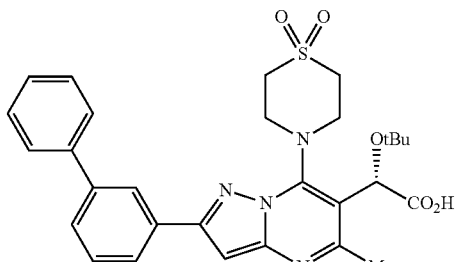

(S)-2-(2-([1,1'-Biphenyl]-3-yl)-7-(1,1-dioxidothiomorpholino)-5-methylpyrazolo[1,5-a]pyrimidin-6-yl)-2-(tert-butoxy)acetic acid ¹H NMR (500 MHz, DMSO-d₆) δ 8.27 (s, 1H), 8.02 (d, J=7.0 Hz, 1H), 7.76 (d, J=7.3 Hz, 2H), 7.72 (d, J=7.3 Hz, 1H), 7.61 (t, J=7.8 Hz, 1H), 7.51 (t, J=7.5 Hz, 2H), 7.44-7.38 (m, 1H), 7.20 (s, 1H), 5.48 (br. s., 1H), 4.40 (br. s., 2H), 4.09 (br. s., 2H), 2.61 (s, 3H), 1.21 (s, 9H). LCMS (ESI, M+1): 549.4.

EXAMPLE 47

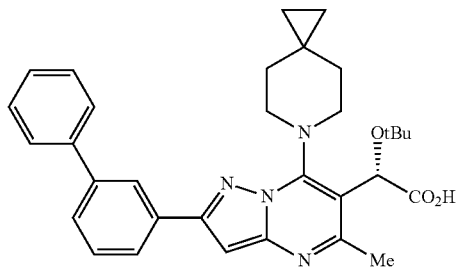 [SMILES: Cc1nc2cc(-c3cccc(-c4ccccc4)c3)nn2c(N2CCC3(CC2)CC3)c1[C@H](OC(C)(C)C)C(=O)O]

(S)-2-(2-([1,1'-Biphenyl]-3-yl)-5-methyl-7-(6-azaspiro[2.5]octan-6-yl)pyrazolo[1,5-a]pyrimidin-6-yl)-2-(tert-butoxy)acetic acid ¹H NMR (500 MHz, DMSO-d₆) δ 8.30 (s, 1H), 8.02 (d, J=7.3 Hz, 1H), 7.76 (d, J=7.9 Hz, 2H), 7.71 (d, J=7.6 Hz, 1H), 7.60 (t, J=7.8 Hz, 1H), 7.51 (t, J=7.3 Hz, 2H), 7.44-7.38 (m, 1H), 7.12 (s, 1H), 5.73 (br. s., 1H), 3.56-3.53 (m, 4H), 2.88 (s, 2H), 2.72 (s, 1H), 2.54 (br. s., 1H), 2.52 (br. s., 3H), 1.90 (s, 1H), 1.19 (s, 9H), 0.44 (br. s., 4H). LCMS (ESI, M+1): 524.4.

EXAMPLE 48

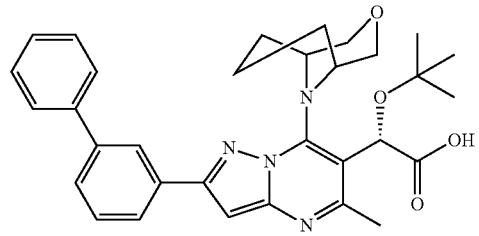 [SMILES: Cc1nc2cc(-c3cccc(-c4ccccc4)c3)nn2c(N2C3CCCC2COC3)c1[C@H](OC(C)(C)C)C(=O)O]

(2S)-2-(2-([1,1'-Biphenyl]-3-yl)-7-(3-oxa-9-azabicyclo[3.3.1]nonan-9-yl)-5-methylpyrazolo[1,5-a]pyrimidin-6-yl)-2-(tert-butoxy)acetic acid ¹H NMR (500 MHz, DMSO-d₆) δ 8.24 (s, 1H), 7.96 (d, J=6.7 Hz, 1H), 7.75 (d, J=7.6 Hz, 2H), 7.69 (d, J=7.3 Hz, 1H), 7.58 (t, J=7.8 Hz, 1H), 7.51 (t, J=7.5 Hz, 2H), 7.43-7.39 (m, 1H), 7.00 (s, 1H), 5.19 (s, 1H), 4.37 (br. s., 1H), 4.19 (br. s., 1H), 4.10 (d, J=11.0 Hz, 1H), 3.94 (d, J=11.3 Hz, 1H), 3.78 (d, J=9.2 Hz, 2H), 2.46 (s, 3H), 1.99 (d, J=9.2 Hz, 2H), 1.90 (s, 2H), 1.77 (d, J=18.0 Hz, 1H), 1.26 (d, J=7.0 Hz, 1H), 1.11 (s, 9H). LCMS (ESI, M+1): 541.4.

EAMPLE 49

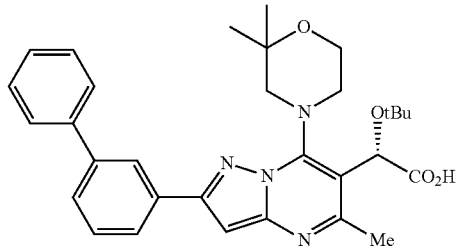 [SMILES: Cc1nc2cc(-c3cccc(-c4ccccc4)c3)nn2c(N2CCOC(C)(C)C2)c1[C@H](OC(C)(C)C)C(=O)O]

(S)-2-(2-([1,1'-Biphenyl]-3-yl)-7-(2,2-dimethylmorpholino)-5-methylpyrazolo[1,5-a]pyrimidin-6-yl)-2-(tert-butoxy)acetic acid ¹H NMR (500 MHz, DMSO-d₆) δ 8.25 (br. s., 1H), 8.03 (d, J=7.3 Hz, 1H), 7.75 (d, J=7.6 Hz, 2H), 7.71 (d, J=7.6 Hz, 1H), 7.60 (t, J=7.6 Hz, 1H), 7.52 (t, J=7.6 Hz, 2H), 7.42 (d, J=7.0 Hz, 1H), 7.15 (s, 1H), 5.79 (br. s., 1H), 4.07 (br. s., 2H), 3.87 (d, J=16.8 Hz, 2H), 2.88 (s, 2H), 2.52 (br. s., 3H), 1.35 (br. s., 6H), 1.18 (s, 9H). LCMS (ESI, M+1): 529.3.

EXAMPLE 50

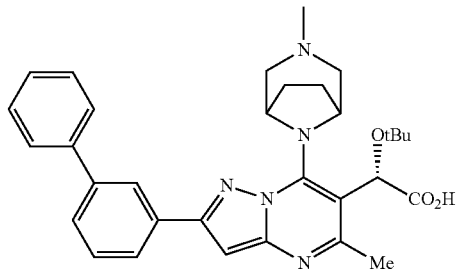 [SMILES: Cc1nc2cc(-c3cccc(-c4ccccc4)c3)nn2c(N2C3CCC2CN(C)C3)c1[C@H](OC(C)(C)C)C(=O)O]

(S)-2-(2-([1,1'-Biphenyl]-3-yl)-5-methyl-7-((1R,5S)-3-methyl-3,8-diazabicyclo[3.2.4]octan-8-yl)pyrazolo[1,5-a]pyrimidin-6-yl)-2-(tert-butoxy)acetic acid ¹H NMR (500 MHz, DMSO-d₆) δ 8.24 (br. s., 1H), 7.97 (d, J=7.3 Hz, 1H), 7.75 (d, J=7.6 Hz, 2H), 7.68 (d, J=7.6 Hz, 1H), 7.58 (t, J=7.0 Hz, 1H), 7.51 (br. s., 2H), 7.44-7.37 (m, 1H), 6.99 (s, 1H), 5.37 (br. s., 1H), 2.91-2.69 (m, 6H), 2.46 (br. s., 3H), 2.31 (d, J=10.1 Hz, 1H), 2.26 (br. s., 3H), 2.11 (br. s., 1H), 1.99 (br. s., 1H), 1.68 (br. s., 1H), 1.13 (br. s., 9H). LCMS (ESI, M+1): 540.3.

EXAMPLE 51

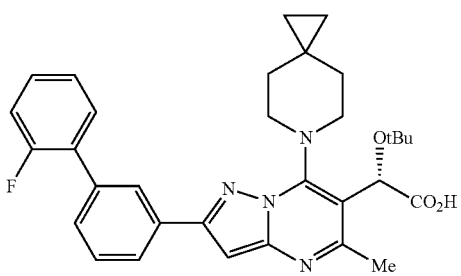 [SMILES: Cc1nc2cc(-c3cccc(-c4ccccc4F)c3)nn2c(N2CCC3(CC2)CC3)c1[C@H](OC(C)(C)C)C(=O)O]

(S)-2-(tert-Butoxy)-2-(2-(2'-fluoro-[1,1'-biphenyl]-3-yl)-5-methyl-7-(6-azaspiro[2.5]octan-6-yl)pyrazolo[1,5-a]pyrimidin-6-yl)acetic acid ¹H NMR (500 MHz, DMSO-d₆) δ 8.21 (br. s., 1H), 8.05 (d, J=5.2 Hz, 1H), 7.61 (d, J=8.9 Hz, 3H), 7.46 (br. s., 1H), 7.34 (d, J=7.6 Hz, 2H), 7.07 (br. s., 1H), 5.75 (br. s., 1H), 3.64-3.60 (m, 4H), 3.28-3.26 (m, 2H), 2.53-2.51 (m, 3H), 1.90 (br. s., 2H), 1.19 (br. s., 9H), 0.42 (br. s., 4H). LCMS (ESI, M+1): 543.3.

EXAMPLE 52

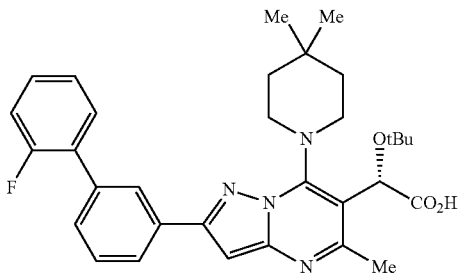 [SMILES: Cc1nc2cc(-c3cccc(-c4ccccc4F)c3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-2-(2'-fluoro-[1,1'-biphenyl]-3-yl)-5-methylpyrazolo[1,5-a]pyrimidin-6-yl)acetic acid ¹H NMR (500 MHz, DMSO-d₆) δ 8.25 (br. s., 1H), 8.04 (d, J=6.1 Hz, 1H), 7.60 (d, J=6.7 Hz, 3H), 7.45 (br. s., 1H), 7.33 (br. s., 2H), 7.06 (br. s., 1H), 5.73 (br. s., 1H), 3.52-3.51 (m, 4H), 2.54-2.51 (m, 3H), 1.61 (br. s., 2H), 1.48 (br. s., 2H), 1.17 (br. s., 9H), 1.08 (br. s., 6H). LCMS (ESI, M+1): 545.3.

EXAMPLE 53

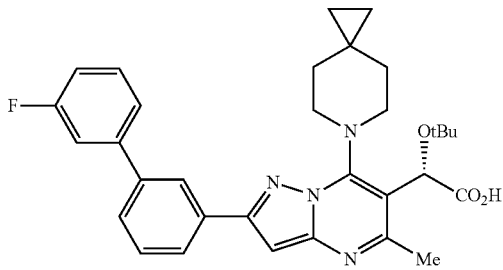 [SMILES: Cc1nc2cc(-c3cccc(-c4cccc(F)c4)c3)nn2c(N2CCC3(CC2)CC3)c1[C@H](OC(C)(C)C)C(=O)O]

(S)-2-(tert-Butoxy)-2-(2-(3'-fluoro-[1,1'-biphenyl]-3-yl)-5-methyl-7-(6-azaspiro[2.5]octan-6-yl)pyrazolo[1,5-a]pyrimidin-6-yl)acetic acid ¹H NMR (500 MHz, DMSO-d₆) δ 8.33 (br. s., 1H), 8.07 (d, J=7.6 Hz, 1H), 7.75 (d, J=6.4 Hz, 1H), 7.67-7.50 (m, 4H), 7.24 (br. s., 1H), 7.15 (s, 1H), 5.67 (br. s., 1H), 3.58-3.45 (m, 4H), 2.89 (s, 1H), 2.73 (s, 1H), 2.52 (br. s., 3H), 1.90 (s, 2H), 1.19 (br. s., 9H), 0.44 (br. s., 4H). LCMS (ESI, M+1): 543.3.

EXAMPLE 54

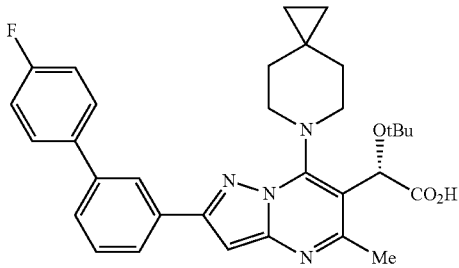 [SMILES: Cc1nc2cc(-c3cccc(-c4ccc(F)cc4)c3)nn2c(N2CCC3(CC2)CC3)c1[C@H](OC(C)(C)C)C(=O)O]

(S)-2-(tert-Butoxy)-2-(2-(4'-fluoro-[1,1'-biphenyl]-3-yl)-5-methyl-7-(6-azaspiro[2.5]octan-6-yl)pyrazolo[1,5-a]pyrimidin-6-yl)acetic acid $^1$H NMR (500 MHz, DMSO-d$_6$) δ 8.27 (br. s., 1H), 8.03 (d, J=7.3 Hz, 1H), 7.80 (d, J=5.5 Hz, 2H), 7.69 (d, J=7.6 Hz, 1H), 7.59 (t, J=6.9 Hz, 1H), 7.34 (t, J=7.8 Hz, 2H), 7.12 (br. s., 1H), 5.69 (br. s., 1H), 3.36 (br. s., 6H), 2.89 (s, 1H), 2.73 (s, 1H), 2.52 (br. s., 3H), 1.19 (br. s., 9H), 0.43 (br. s., 4H). LCMS (ESI, M+1): 543.3.

EXAMPLE 55

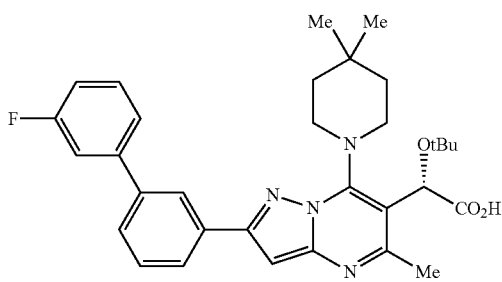 [SMILES: Cc1nc2cc(-c3cccc(-c4cccc(F)c4)c3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-2-(3'-fluoro-[1,1'-biphenyl]-3-yl)-5-methylpyrazolo[1,5-a]pyrimidin-6-yl)acetic acid $^1$H NMR (500 MHz, DMSO-d$_6$) δ 8.37 (br. s., 1H), 8.05 (d, J=8.2 Hz, 1H), 7.75 (d, J=7.3 Hz, 1H), 7.65-7.50 (m, 4H), 7.24 (br. s., 1H), 7.15 (s, 1H), 5.72 (br. s., 1H), 3.46-3.42 (m, 4H), 2.52 (br. s., 3H), 1.63 (br. s., 2H), 1.50 (br. s., 2H), 1.18 (br. s., 9H), 1.11 (br. s., 6H). LCMS (ESI, M+1): 545.3.

EXAMPLE 56

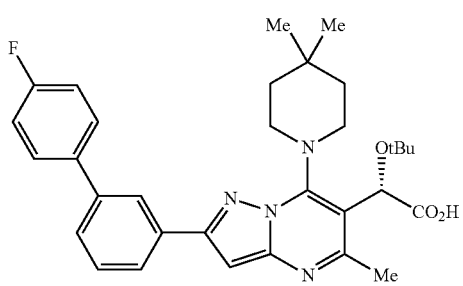 [SMILES: Cc1nc2cc(-c3cccc(-c4ccc(F)cc4)c3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-2-(4'-fluoro-[1,1'-biphenyl]-3-yl)-5-methylpyrazolo[1,5-a]pyrimidin-6-yl)acetic acid $^1$H NMR (500 MHz, DMSO-d$_6$) δ 8.31 (br. s., 1H), 8.02 (d, J=7.6 Hz, 1H), 7.79 (br. s., 2H), 7.69 (d, J=7.3 Hz, 1H), 7.59 (t, J=7.5 Hz, 1H), 7.33 (t, J=8.7 Hz, 2H), 7.13 (s, 1H), 5.74 (br. s., 1H), 3.34-3.31 (m, 4H), 2.52 (br. s., 3H), 1.62 (br. s., 2H), 1.50 (br. s., 2H), 1.18 (s, 9H), 1.10 (br. s., 6H). LCMS (ESI, M+1): 545.3.

EXAMPLE 57

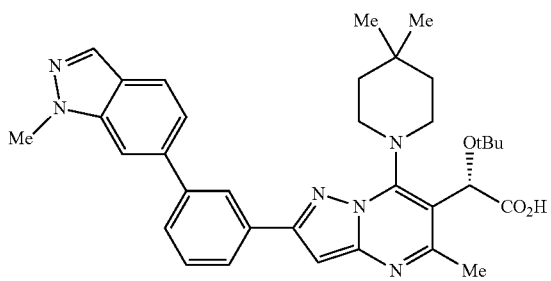 [SMILES: Cc1nc2cc(-c3cccc(-c4ccc5cnn(C)c5c4)c3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-5-methyl-2-(3-(1-methyl-1H-indazol-6-yl)phenyl)pyrazolo[1,5-a]pyrimidin-6-yl)acetic acid $^1$H NMR (500 MHz, DMSO-d$_6$) δ 8.46 (br. s., 1H), 8.11-8.03 (m, 2H), 8.01 (br. s., 1H), 7.85 (t, J=8.7 Hz, 2H), 7.69-7.60 (m, 1H), 7.54 (d, J=8.2 Hz, 1H), 7.19 (br. s., 1H), 5.81 (br. s., 1H), 4.13 (br. s., 3H), 3.49-3.43 (m, 4H), 2.53 (br. s., 3H), 1.64 (br. s., 2H), 1.51 (br. s., 2H), 1.19 (br. s., 9H), 1.12 (br. s., 6H). LCMS (ESI, M+1): 581.3.

EXAMPLE 58

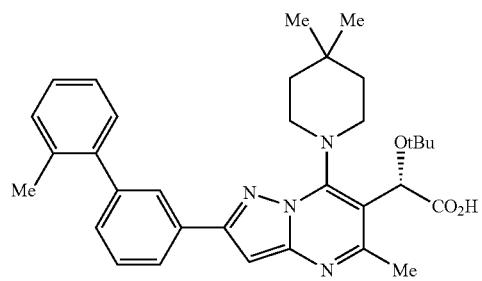 [SMILES: Cc1ccccc1-c1cccc(-c2cc3nc(C)c([C@H](OC(C)(C)C)C(=O)O)c(N4CCC(C)(C)CC4)n3n2)c1]

(S)-2-(tert-Butoxy)-2-(7-(4,4-dimethylpiperidin-1-yl)-5-methyl-2-(2'-methyl-[1,1'-biphenyl]-3-yl)pyrazolo[1,5-a]pyrimidin-6-yl)acetic acid $^1$H NMR (500 MHz, DMSO-d$_6$) δ 8.01 (br. s., 1H), 7.56 (d, J=7.9 Hz, 1H), 7.39 (d, J=7.9 Hz, 1H), 7.29 (br. s., 4H), 7.08 (br. s., 1H), 5.80 (br. s., 1H), 3.43-3.39 (m, 4H), 2.52 (br. s., 3H), 2.30 (br. s., 3H), 1.59 (br. s., 2H), 1.48 (br. s., 2H), 1.18 (br. s., 9H), 1.07 (br. s., 6H). LCMS (ESI, M+1): 541.3.

EXAMPLE 59

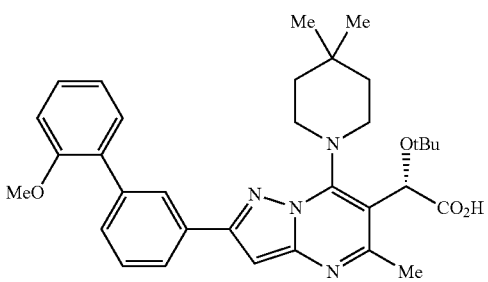 [SMILES: COc1ccccc1-c1cccc(-c2cc3nc(C)c([C@H](OC(C)(C)C)C(=O)O)c(N4CCC(C)(C)CC4)n3n2)c1]

(S)-2-(tert-Butoxy)-2-(7-(4,4-dimethylpiperidin-1-yl)-2-(2'-methoxy-[1,1'-biphenyl]-3-yl)-5-methylpyrazolo[1,5-a]pyrimidin-6-yl)acetic acid $^1$H NMR (500 MHz, DMSO-d$_6$) δ 8.18 (br. s., 1H), 7.94 (br. s., 1H), 7.51 (br. s., 2H), 7.37 (d, J=7.3 Hz, 2H), 7.15 (d, J=7.6 Hz, 1H), 7.06 (br. s., 1H), 7.01 (br. s., 1H), 5.68 (br. s., 1H), 3.79 (br. s., 3H), 3.37 (br. s., 4H), 2.51 (br. s., 3H), 1.61 (br. s., 2H), 1.48 (br. s., 2H), 1.17 (br. s., 9H), 1.07 (br. s., 6H). LCMS (ESI, M+1): 557.3.

EXAMPLE 60

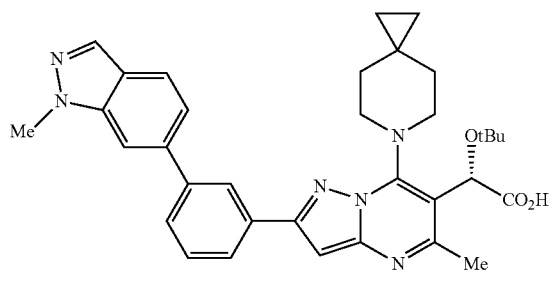 [SMILES: Cc1nc2cc(-c3cccc(-c4ccc5cnn(C)c5c4)c3)nn2c(N2CCC3(CC2)CC3)c1[C@H](OC(C)(C)C)C(=O)O]

(S)-2-(tert-Butoxy)-2-(5-methyl-2-(3-(1-methyl-1H-indazol-6-yl)phenyl)-7-(6-azaspiro[2.5]octan-6-yl)pyrazolo[1,5-a]pyrimidin-6-yl)acetic acid $^1$H NMR (500 MHz, DMSO-d$_6$) δ 8.41 (br. s., 1H), 8.11-8.00 (m, 3H), 7.90-7.80 (m, 2H), 7.63 (br. s., 1H), 7.56 (d, J=7.3 Hz, 1H), 7.14 (s, 1H), 5.63 (br. s., 1H), 4.14 (br. s., 3H), 3.39 (br. s., 4H), 2.52 (br. s., 3H), 1.18 (br. s., 9H), 0.44 (br. s., 4H). LCMS (ESI, M+1): 579.3.

EXAMPLE 61

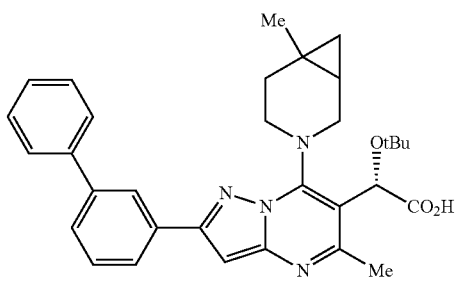 [SMILES: Cc1nc2cc(-c3cccc(-c4ccccc4)c3)nn2c(N2CCC3(C)CC3C2)c1[C@H](OC(C)(C)C)C(=O)O]

(2S)-2-(2-([1,1'-Biphenyl]-3-yl)-5-methyl-7-(6-methyl-3-azabicyclo[4.1.0]heptan-3-yl)pyrazolo[1,5-a]pyrimidin-6-yl)-2-(tert-butoxy)acetic acid $^1$H NMR (500 MHz, DMSO-d$_6$) δ 8.29 (br. s., 1H), 8.03 (d, J=7.3 Hz, 1H), 7.76 (d, J=7.3 Hz, 2H), 7.70 (d, J=7.0 Hz, 1H), 7.60 (s, 1H), 7.52 (t, J=7.3 Hz, 2H), 7.42 (t, J=7.3 Hz, 2H), 7.10 (s, 1H), 5.56 (br. s., 1H), 4.47-3.76 (m, 4H), 2.50 (br. s., 3H), 1.82-1.71 (m, 1H), 1.26-1.10 (m, 14H), 0.75 (br. s., 1H), 0.57-0.48 (m, 1H); LCMS (ESI, M+1): 525.3.

EXAMPLE 62

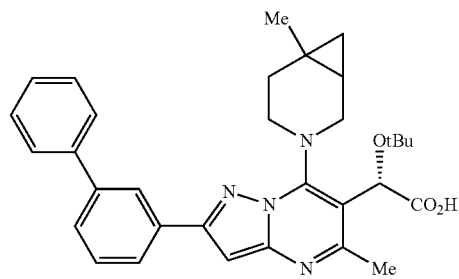 [SMILES: Cc1nc2cc(-c3cccc(-c4ccccc4)c3)nn2c(N2CCC3(C)CC3C2)c1[C@H](OC(C)(C)C)C(=O)O]

(2S)-2-(2-([1,1'-Biphenyl]-3-yl)-5-methyl-7-(6-methyl-3-azabicyclo[4.1.0]heptan-3-yl)pyrazolo[1,5-a]pyrimidin-6-yl)-2-(tert-butoxy)acetic acid $^1$H NMR (500 MHz, DMSO-d$_6$) δ 8.27-8.21 (m, 1H), 8.06-8.01 (m, 1H), 7.79-7.74 (m, 2H), 7.72-7.68 (m, 1H), 7.63-7.57 (m, 1H), 7.55-7.49 (m, 2H), 7.44-7.38 (m, 1H), 7.16-7.11 (m, 1H), 5.78-5.72 (m, 1H), 3.83-3.64 (m, 4H), 2.50 (br. s., 3H), 2.00-1.94 (m, 1H), 1.25-1.22 (m, 1H), 1.18 (br. s., 12H), 1.02-0.96 (m, 1H), 0.79-0.74 (m, 1H), 0.62-0.55 (m, 1H); LCMS (ESI, M+1): 525.4.

EXAMPLE 63

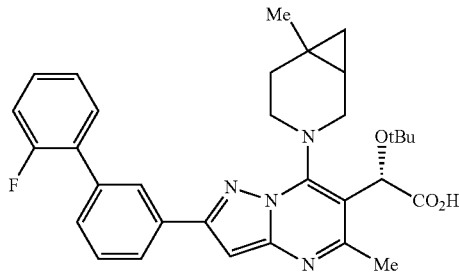 [SMILES: Cc1nc2cc(-c3cccc(-c4ccccc4F)c3)nn2c(N2CCC3(C)CC3C2)c1[C@H](OC(C)(C)C)C(=O)O]

(2S)-2-(tert-Butoxy)-2-(2-(2'-fluoro-[1,1'-biphenyl]-3-yl)-5-methyl-7-(6-methyl-3-azabicyclo[4.1.0]heptan-3-yl)pyrazolo[1,5-a]pyrimidin-6-yl)acetic acid $^1$H NMR (500 MHz, DMSO-d$_6$) δ 8.21 (br. s., 1H), 8.06 (d, J=7.0 Hz, 1H), 7.67-7.55 (m, 3H), 7.47 (d, J=6.4 Hz, 1H), 7.41-7.31 (m, 2H), 7.04 (s, 1H), 5.51 (br. s., 1H), 3.91 (br. s., 4H), 2.50 (br. s., 3H), 1.76 (br. s., 1H), 1.28-1.07 (m, 14H), 0.72 (br. s., 1H), 0.50 (d, J=5.2 Hz, 1H); LCMS (ESI, M+1): 543.27.

EXAMPLE 64

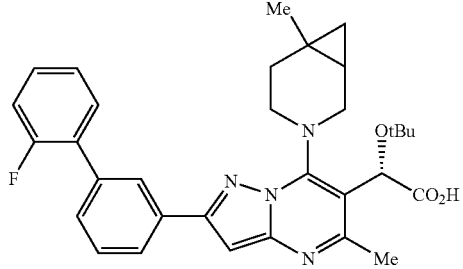 [SMILES: Cc1nc2cc(-c3cccc(-c4ccccc4F)c3)nn2c(N2CCC3(C)CC3C2)c1[C@H](OC(C)(C)C)C(=O)O]

(2S)-2-(tert-Butoxy)-2-(2-(2'-fluoro-[1,1'-biphenyl]-3-yl)-5-methyl-7-(6-methyl-3-azabicyclo[4.1.0]heptan-3-yl)pyrazolo[1,5-a]pyrimidin-6-yl)acetic acid $^1$H NMR (500 MHz, DMSO-d$_6$) δ 8.18-8.12 (m, 1H), 8.09-8.03 (m, 1H), 7.66-7.55 (m, 3H), 7.50-7.42 (m, 1H), 7.40-7.28 (m, 2H), 7.17-7.00 (m, 1H), 5.89-5.69 (m, 1H), 3.39-3.04 (m, 4H), 2.51 (br. s., 3H), 2.00-1.90 (m, 1H), 1.17 (br. s., 13H), 1.02-0.92 (m, 1H), 0.77-0.69 (m, 1H), 0.62-0.51 (m, 1H); LCMS (ESI, M+1): 543.27.

yl)-2-hydroxyacetate as a waxy yellow solid (1.28 g, 82%). $^1$H NMR (400 MHz, CDCl$_3$) δ 6.57 (s, 1H), 5.53 (d, J=5.3 Hz, 1H), 4.78 (br. s., 1H), 4.52 (d, J=5.3 Hz, 1H), 3.80 (s, 3H), 2.60 (s, 3H), 1.57-1.53 (m, J=3.8 Hz, 4H), 1.10 (s, 6H); LCMS (ESI, M+1): 411.2.

To a solution of methyl 2-(2-bromo-7-(4,4-dimethylpiperidin-1-yl)-5-methylpyrazolo[1,5-a]pyrimidin-6-yl)-2-hydroxyacetate (1.28 g, 3.11 mmol, 1 equiv) in DCM (16 mL) was added Dess-Martin periodindane (1.85 g, 4.36 mmol, 1.4 equiv). After 30 min, the reaction was added saturated aque-

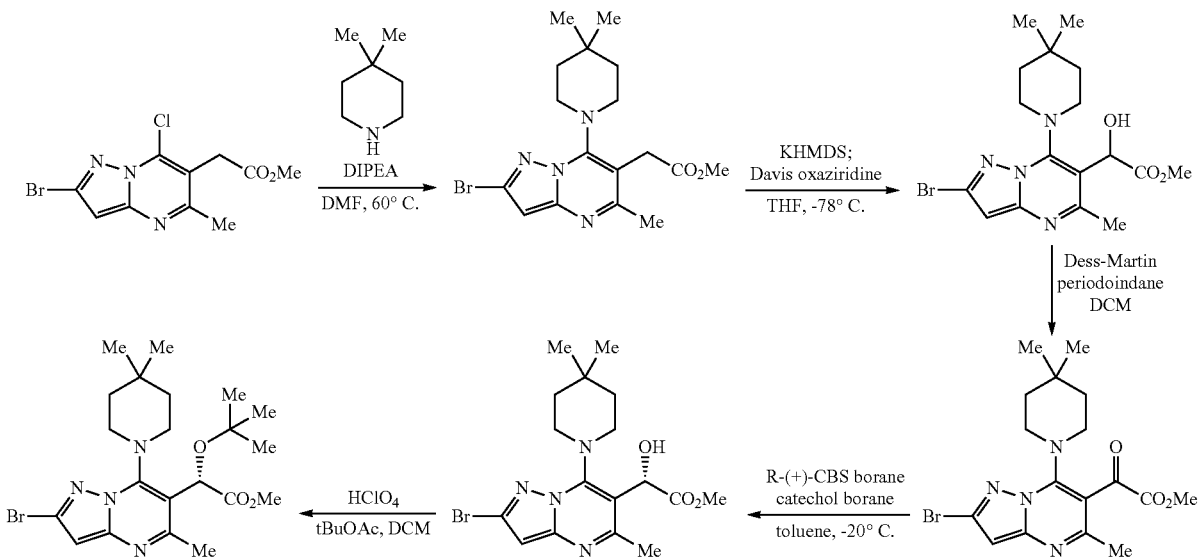

To a solution of methyl 2-(2-bromo-7-chloro-5-methylpyrazolo[1,5-a]pyrimidin-6-yl)acetate (1.33 g, 4.18 mmol, 1 equiv) in DMF (14 mL) was added 4,4-dimethylpiperidine hydrochloride (0.75 g, 5.01 mmol, 1.2 equiv) and DIPEA (1.75 mL, 10.02 mmol, 2.4 equiv). The reaction was then heated in an oil bath at 60° C. Upon completion, the reaction was removed from heating, diluted with water, and extracted with EtOAc (×2). The combined EtOAc extracts were dried over Na$_2$SO$_4$ and concentrated in vacuo. The crude product was purified by silica gel flash chromatography (0-100% EtOAc/hexane) to provide methyl 2-(2-bromo-7-(4,4-dimethylpiperidin-1-yl)-5-methylpyrazolo[1,5-a]pyrimidin-6-yl)acetate as an off white solid (1.50 g, 91%). $^1$H NMR (400 MHz, CDCl$_3$) δ 6.53 (s, 1H), 3.80 (s, 2H), 3.77 (s, 3H), 3.41 (br. s., 4H), 2.51 (s, H), 1.54 (t, J=5.6 Hz, 4H), 1.09 (s, 6H); LCMS (ESI, M+1): 395.25.

To a solution of methyl 2-(2-bromo-7-(4,4-dimethylpiperidin-1-yl)-5-methylpyrazolo[1,5-a]pyrimidin-6-yl)acetate (1.49 g, 3.79 mmol, 1 equiv) in THF (38 mL) at −78° C. (IPA/CO$_2$) was added KHMDS (6.8 mL of a 0.91M solution in THF, 6.07 mmol, 1.6 equiv). The reaction turned a deep orange color. After 15 min, 3-phenyl-2-(phenylsulfonyl)-1,2-oxaziridine (1.49 g, 5.69 mmol, 1.5 equiv) was added in a single portion. The reaction solution significantly darkened and was then allowed to stir for 30 min. The reaction was then removed from the cooling bath and quenched with saturated aqueous solution of NaHCO$_3$, added to water, and extracted with EtOAc (×3). The combined EtOAc extracts were dried over Na$_2$SO$_4$ and concentrated in vacuo. The crude product was purified by silica gel flash chromatography (0-100% EtOAc/hexane) to provide methyl 2-(2-bromo-7-(4,4-dimethylpiperidin-1-yl)-5-methylpyrazolo[1,5-a]pyrimidin-6- ous NHCO$_3$ and extracted with DCM (×3). The combined DCM extracts were dried over Na$_2$SO$_4$ and concentrated in vacuo. The crude product was purified by silica gel flash chromatography (0-50% EtOAc/hexane) to provide methyl 2-(2-bromo-7-(4,4-dimethylpiperidin-1-yl)-5-methylpyrazolo[1,5-a]pyrimidin-6-yl)-2-oxoacetate as a yellow solid (0.71 g, 56%). $^1$H NMR (400 MHz, CDCl$_3$) δ 6.56 (s, 1H), 3.94 (s, 3H), 3.58-3.43 (m, 4H), 2.55 (s, 3H), 1.64-1.50 (m, 4H), 1.05 (s, 6H); LCMS (ESI, M+1): 409.2.

To a solution of methyl 2-(2-bromo-7-(4,4-dimethylpiperidin-1-yl)-5-methylpyrazolo[1,5-a]pyrimidin-6-yl)-2-oxoacetate (6.15 g, 15.03 mmol, 1 equiv) in toluene (200 mL) was added (R)-1-methyl-3,3-diphenylhexahydropyrrolo[1,2-c][1,2,3]oxazaborole (9.0 mL of a 1M solution in toluene, 9.02 mmol, 0.6 equiv). The solution was cooled to −25° C. (acetonitrile/CO$_2$) and catechol borane (8.7 mL of a 50% solution in toluene, 36.1 mmol, 2.4 equiv) was added. The cooling bath temperature was maintained between −15° C. and −25° C. for 4 h. The reaction was then diluted with EtOAc (35 mL) and 10% aqueous solution of K$_2$CO$_3$ (35 mL) and then allowed to warm to ambient temperature. The quenched solution was stirred for 45 min and then added to water. Extract with ether (×3). Combined ether extracts dried over MgSO$_4$ and concentrated in vacuo. The crude product was purified by silica gel flash chromatography (0-70% EtOAc/hexane) to provide (S)-methyl 2-(2-bromo-7-(4,4-dimethylpiperidin-1-yl)-5-methylpyrazolo[1,5-a]pyrimidin-6-yl)-2-hydroxyacetate as a pale yellow glass (5.68 g, 92%). $^1$H NMR (500 MHz, CDCl$_3$) δ 6.58 (s, 1H), 5.54 (d, J=5.2 Hz, 1H), 4.51 (d, J=5.0 Hz, 1H), 3.81 (s, 3H), 3.73-3.14 (m very broad, 4H), 2.62 (s, 3H), 1.60-1.54 (m, 4H), 1.11 (s, 6H); LCMS (ESI, M+1): 411.05.

To a solution of (S)-methyl 2-(2-bromo-7-(4,4-dimethylpiperidin-1-yl)-5-methylpyrazolo[1,5-a]pyrimidin-6-yl)-2-hydroxyacetate (5.68 g, 13.81 mmol, 1 equiv) in DCM (92 mL) and t-butyl acetate (184 mL) was added 70% perchloric acid (3.3 mL, 55.2 mmol, 4 equiv). The reaction turned pale yellow. After 3 h, the reaction was added very cautiously to a saturated aqueous solution of NaHCO$_3$ and extracted with CHCl$_3$ (×3). Combined organic extracts dried over Na$_2$SO$_4$ and concentrated in vacuo. The crude product was purified by silica gel flash chromatography (0-70% EtOAc/hexane) to provide (S)-methyl 2-(2-bromo-7-(4,4-dimethylpiperidin-1-yl)-5-methylpyrazolo[1,5-a]pyrimidin-6-yl)-2-(tert-butoxy)acetate as a pale yellow solid (2.8 g, 43%) and recovered starting material (3.0 g, 53%). $^1$H NMR (400 MHz, CDCl$_3$) δ 6.54 (s, 1H), 5.92 (s, 1H), 3.74 (s, 3H), 2.59 (s, 3H), 1.58 (s, 8H), 1.24 (s, 9H), 1.11 (s, 6H); LCMS (ESI, M+1):467.3.

EXAMPLE 65

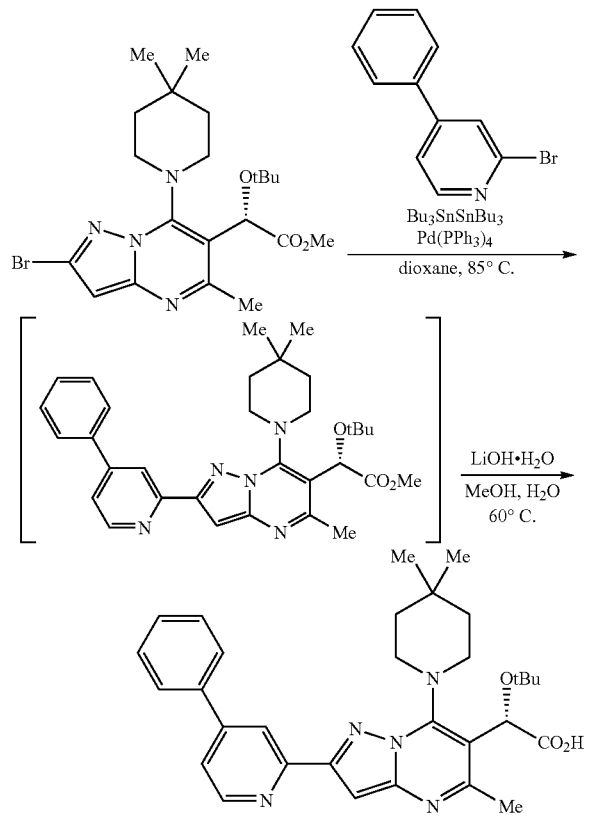

(S)-2-(tert-Butoxy)-2-(7-(4,4-dimethylpiperidin-1-yl)-5-methyl-2-(4-phenylpyridin-2-yl)pyrazolo[1,5-a]pyrimidin-6-yl)acetic acid To a solution of (S)-methyl 2-(2-bromo-7-(4,4-dimethylpiperidin-1-yl)-5-methylpyrazolo[1,5-a]pyrimidin-6-yl)-2-(tert-butoxy)acetate (0.050 g, 0.107 mmol, 1 equiv) in dioxane (1.0 mL) was added 2-bromo-4-phenylpyridine (0.030 g, 0.128 mmol, 1.2 equiv), hexabutyldistannane (0.12 mL, 0.235 mmol, 2.2 equiv), and Pd(PPh$_3$)$_4$ (0.012 g, 0.011 mmol, 0.1 equiv). The reaction was heated at 85° C. for 72 h. The reaction temperature was then lowered to 60° C. Methanol (1 mL), water (0.3 mL), and LiOH.H$_2$O (26 mg, 1.07 mmol, 10 equiv) added and heating was continued for 2 h. Upon completion of the saponification, the reaction was removed from heat and filtered through a syringe filter. The crude reaction mixture was purified via preparative LC/MS with the following conditions: Column: Waters XBridge C18, 19×200 mm, 5-μm particles; Guard Column. Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 45-85% B over 20 minutes, then a 5-minute hold at 100% B; Flow: 20 mL/min, to provide (S)-2-(tert-butoxy)-2-(7-(4,4-dimethylpiperidin-1-yl)-5-methyl-2-(4-phenylpyridin-2-yl)pyrazolo[1,5-a]pyrimidin-6-yl)acetic acid (3.5 mg, 6%). $^1$H NMR (500 MHz, DMSO-d$_6$) δ 8.73 (d, J=4.9 Hz, 1H), 8.48 (s, 1H), 7.83 (d, J=7.6 Hz, 2H), 7.75 (d, J=4.0 Hz, 1H), 7.60-7.49 (m, 3H), 7.06 (s, 1H), 5.72 (br. s., 1H), 3.61-3.55 (m, 4H), 2.53 (s, 3H), 1.65 (br. s., 2H), 1.50 (br. s., 2H), 1.18 (s, 9H), 1.11 (br. s., 6H). LCMS (ESI, M+1): 528.3.

The following compounds are prepared according to the procedure described above for example XX.

EXAMPLE 66

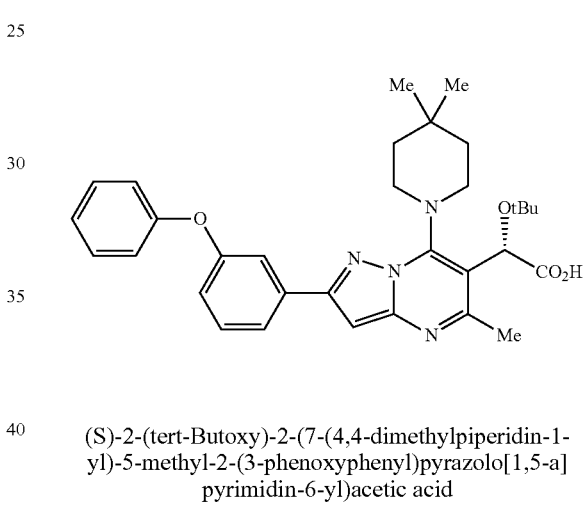

(S)-2-(tert-Butoxy)-2-(7-(4,4-dimethylpiperidin-1-yl)-5-methyl-2-(3-phenoxyphenyl)pyrazolo[1,5-a]pyrimidin-6-yl)acetic acid $^1$H NMR (500 MHz, DMSO-d$_6$) δ 7.77 (d, J=7.9 Hz, 1H), 7.65 (br. s., 1H), 7.50 (t, J=7.5 Hz, 1H), 7.42 (t, J=7.5 Hz, 2H), 7.18 (t, J=7.9 Hz, 1H), 7.10 (d, J=7.9 Hz, 2H), 7.08-7.02 (m, 2H), 5.76 (br. s., 1H), 3.89 (s, 2H), 2.96-2.86 (m, 2H), 1.90 (s, 3H), 1.55 (br. s., 2H), 1.44 (br. s., 2H), 1.17 (s, 9H), 1.01 (s, 6H). LCMS (ESI, M+1): 543.4.

EXAMPLE 67

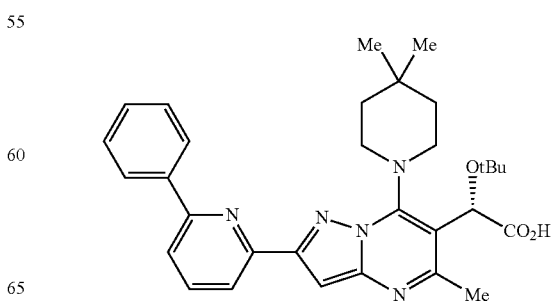

(S)-2-(tert-Butoxy)-2-(7-(4,4-dimethylpiperidin-1-yl)-5-methyl-2-(6-phenylpyridin-2-yl)pyrazolo[1,5-a]pyrimidin-6-yl)acetic acid ¹H NMR (500 MHz, DMSO-d₆) δ 8.24 (d, J=7.3 Hz, 2H), 8.12-8.07 (m, 1H), 8.06-7.97 (m, 2H), 7.57-7.51 (m, 2H), 7.48 (d, J=7.0 Hz, 1H), 7.14 (s, 1H), 5.67 (br. s., 1H), 2.52 (br. s., 3H), 1.90 (s, 4H), 1.63 (br. s., 2H), 1.43 (d, J=7.3 Hz, 2H), 1.17 (s, 9H), 0.74 (br. s., 6H). LCMS (ESI, M+1): 528.3.

EXAMPLE 68

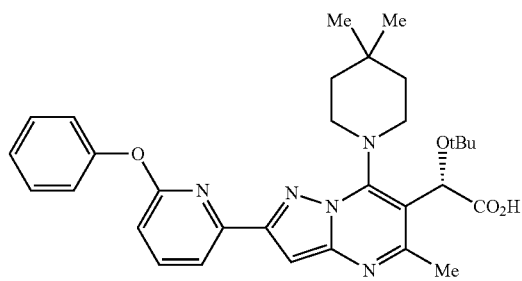 [SMILES: Cc1nc2cc(-c3cccc(Oc4ccccc4)n3)nn2c(N2CCC(C)(C)CC2)c1[C@H](OC(C)(C)C)C(=O)O]

(S)-2-(tert-Butoxy)-2-(7-(4,4-dimethylpiperidin-1-yl)-5-methyl-2-(6-phenoxypyridin-2-yl)pyrazolo[1,5-a]pyrimidin-6-yl)acetic acid ¹H NMR (500 MHz, DMSO-d₆) δ 8.01-7.92 (m, 1H), 7.85 (d, J=7.0 Hz, 1H), 7.49-7.42 (m, 2H), 7.23 (d, J=7.9 Hz, 3H), 6.95 (d, J=8.2 Hz, 1H), 6.63 (s, 1H), 5.58 (br. s., 1H), 3.54-3.50 (m, 4H), 2.47 (br. s., 3H), 1.58 (br. s., 2H), 1.38 (br. s., 2H), 1.14 (br. s., 9H), 0.94 (br. s., 6H). LCMS (ESI, M+1): 543.3.

EXAMPLE 69

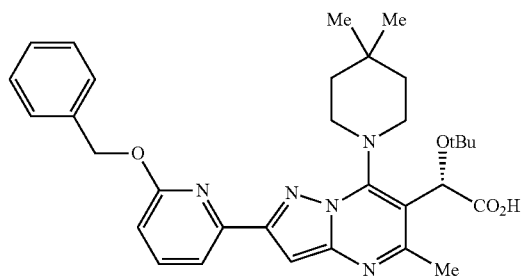 [SMILES: Cc1nc2cc(-c3cccc(OCc4ccccc4)n3)nn2c(N2CCC(C)(C)CC2)c1[C@H](OC(C)(C)C)C(=O)O]

(S)-2-(2-(6-(Benzyloxy)pyridin-2-yl)-7-(4,4-dimethylpiperidin-1-yl)-5-methylpyrazolo[1,5-a]pyrimidin-6-yl)-2-(tert-butoxy)acetic acid ¹H NMR (500 MHz, DMSO-d₆) δ 7.83 (d, J=7.9 Hz, 1H), 7.72 (d, J=7.3 Hz, 1H), 7.52 (d, J=7.0 Hz, 2H), 7.41-7.33 (m, 2H), 7.30 (d, J=7.6 Hz, 1H), 7.03 (s, 1H), 6.87 (d, J=8.2 Hz, 1H), 5.68 (br. s., 1H), 5.49 (s, 2H), 3.66-3.64 (m, 4H), 2.55-2.51 (m, 3H), 1.60 (br. s., 2H), 1.47 (br. s., 2H), 1.16 (s, 9H), 1.06 (br. s., 6H). LCMS (ESI, M+1): 558.3.

EXAMPLE 70

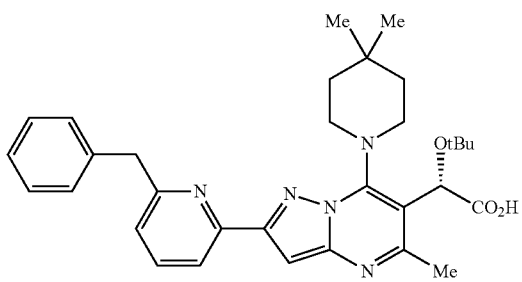 [SMILES: Cc1nc2cc(-c3cccc(Cc4ccccc4)n3)nn2c(N2CCC(C)(C)CC2)c1[C@H](OC(C)(C)C)C(=O)O]

(S)-2-(2-(6-Benzylpyridin-2-yl)-7-(4,4-dimethylpiperidin-1-yl)-5-methylpyrazolo[1,5-a]pyrimidin-6-yl)-2-(tert-butoxy)acetic acid ¹H NMR (500 MHz, DMSO-d₆) δ 7.96 (d, J=7.6 Hz, 1H), 7.85 (t, J=7.6 Hz, 1H), 7.38-7.33 (m, 2H), 7.33-7.23 (m, 3H), 7.21 (d, J=7.3 Hz, 1H), 7.00 (s, 1H), 5.72 (br. s., 1H), 4.16 (br. s., 2H), 3.63-3.58 (m, 4H), 2.52 (br. s., 3H), 1.60 (br. s., 2H), 1.49 (br. s., 2H), 1.17 (s, 9H), 1.08 (br. s., 6H). LCMS (ESI, M+1): 542.3.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

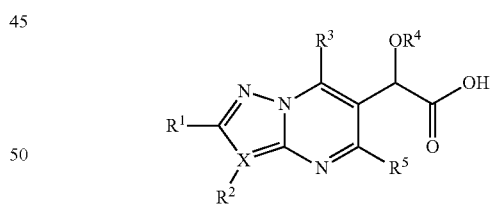

where:
X is C or N;
R¹ is hydrogen or Ar¹;
R² is hydrogen or Ar¹;
provided that when X is C either R¹ is Ar¹ and R² is hydrogen or R² is Ar¹ and R¹ is hydrogen, and when X is N R¹ is Ar¹ and R² is hydrogen;
R³ is N(R⁶)(R⁷);
R⁴ is alkyl or haloalkyl;
R⁵ is alkyl;
R⁶ is hydrogen or alkyl;
R⁷ is hydrogen or alkyl;
or N(R⁶)(R⁷) taken together is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxy, alkoxy, haloalkoxy, carboxy, or carboxamido;

or $N(R^6)(R^7)$ taken together is indolinyl, isoindolinyl, tetrahydroisoquinolinyl, or decahydroisoquinolinyl, and is substituted with 0-3 substituents selected from halo, alkyl, haloalkyl, hydroxy, alkoxy, haloalkoxy, carboxy, or carboxamido;

or $N(R^6)(R^7)$ taken together is a [4.2.0,], [4.3.0,], [4.4.0,], [4.5.0,], [4.6.0,], [5.2.0,], [5.3.0,], [5.4.0,], [5.5.0,], [5.6.0,], [6.2.0,], [6.3.0,], [6.4.0,], [6.5.0,], [6.6.0,] spirocyclic amine;

or $N(R^6)(R^7)$ taken together is

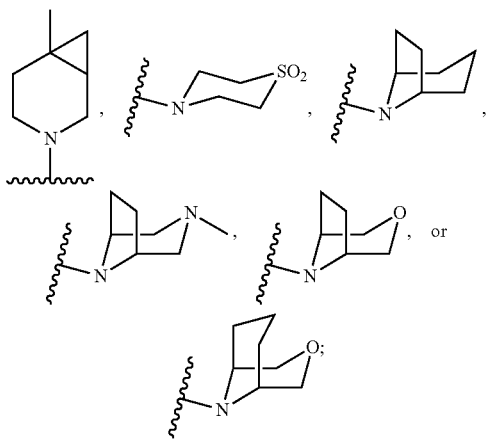

and $Ar^1$ is phenyl, pyridinyl, or biphenyl and is substituted with 0-3 substituents selected from halo, alkyl, haloalkyl, cycloalkyl, halocycloalkyl, alkoxy, haloalkoxy, phenyl, benzyl, phenoxy, and benzyloxy wherein said phenyl, benzyl, phenoxy, and benzyloxy is substituted with 0-3 halo, alkyl, haloalkyl, cycloalkyl, halocycloalkyl, alkoxy, and haloalkoxy substituents;

or $Ar^1$ is tetralinyl, ((methyl)indazolyl)phenyl, or (benzyloxy)phenyl;

or a pharmaceutically acceptable salt thereof.

2. A compound of claim 1 where:
X is C or N;
$R^1$ is hydrogen or $Ar^1$;
$R^2$ is hydrogen or $Ar^1$;
provided that when X is C either $R^1$ is $Ar^1$ and $R^2$ is hydrogen or $R^2$ is $Ar^1$ and $R^1$ is hydrogen, and when X is N $R^1$ is $Ar^1$ and $R^2$ is hydrogen;
$R^3$ is $N(R^6)(R^7)$;
$R^4$ is alkyl or haloalkyl;
$R^5$ is alkyl;
$R^6$ is hydrogen or alkyl;
$R^7$ is hydrogen or alkyl;
or $N(R^6)(R^7)$ taken together is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxy, alkoxy, haloalkoxy, carboxy, or carboxamido;
or $N(R^6)(R^7)$ taken together is indolinyl, isoindolinyl, tetrahydroisoquinolinyl, or decahydroisoquinolinyl, and is substituted with 0-3 substituents selected from halo, alkyl, haloalkyl, hydroxy, alkoxy, haloalkoxy, carboxy, or carboxamido;
or $N(R^6)(R^7)$ taken together is a [4.2.0,], [4.3.0,], [4.4.0,], [4.5.0,], [4.6.0,], [5.2.0,], [5.3.0,], [5.4.0,], [5.5.0,], [5.6.0,], [6.2.0,], [6.3.0,], [6.4.0,], [6.5.0,], [6.6.0,] spirocyclic amine; and
$Ar^1$ is phenyl or biphenyl and is substituted with 0-3 substituents selected from halo, alkyl, haloalkyl, cycloalkyl, and halocycloalkyl;
or $Ar^1$ is tetralinyl or (benzyloxy)phenyl;
or a pharmaceutically acceptable salt thereof.

3. A compound of claim 1 where:
X is C or N;
$R^1$ is hydrogen or $Ar^1$;
$R^2$ is hydrogen or $Ar^1$;
provided that when X is C either $R^1$ is $Ar^1$ and $R^2$ is hydrogen or $R^2$ is $Ar^1$ and $R^1$ is hydrogen, and when X is N $R^1$ is $Ar^1$ and $R^2$ is hydrogen;
$R^3$ is $N(R^6)(R^7)$;
$R^4$ is alkyl;
$R^5$ is alkyl;
$N(R^6)(R^7)$ taken together is pyrrolidinyl, piperidinyl, piperazinyl, morpholinyl, homopiperidinyl, or homopiperazinyl, and is substituted with 0-3 substituents selected from halo, alkyl, haloalkyl, hydroxy, alkoxy, haloalkoxy, carboxy, or carboxamido;
or $N(R^6)(R^7)$ taken together is indolinyl, isoindolinyl, tetrahydroisoquinolinyl, or decahydroisoquinolinyl;
or $N(R^6)(R^7)$ taken together is a [4.4.0,], [5.2.0,], or [5.4.0,] spirocyclic amine; and
$Ar^1$ is phenyl or biphenyl and is substituted with 0-3 substituents selected from halo, alkyl, haloalkyl, cycloalkyl, and halocycloalkyl;
or $Ar^1$ is tetralinyl or (benzyloxy)phenyl;
or a pharmaceutically acceptable salt thereof.

4. A compound of claim 1 where X is C, $R^1$ is $Ar^1$, and $R^2$ is hydrogen.

5. A compound of claim 1 where X is N, $R^1$ is $Ar^1$, and $R^2$ is hydrogen.

6. A compound of claim 1 where $R^4$ is alkyl.

7. A compound of claim 5 where $R^4$ is t-butyl.

8. A compound of claim 1 where $R^5$ is methyl.

9. A compound of claim 1 where $N(R^6)(R^7)$ taken together is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxy, alkoxy, haloalkoxy, carboxy, or carboxamido.

10. A compound of claim 8 where $N(R^6)(R^7)$ taken together is pyrrolidinyl, piperidinyl, piperazinyl, morpholinyl, homopiperidinyl, or homopiperazinyl, and is substituted with 0-3 substituents selected from halo, alkyl, haloalkyl, hydroxy, alkoxy, haloalkoxy, carboxy, or carboxamido.

11. A compound of claim 1 where $N(R^6)(R^7)$ taken together is indolinyl, isoindolinyl, tetrahydroisoquinolinyl, or decahydroisoquinolinyl, and is substituted with 0-3 substituents selected from halo, alkyl, haloalkyl, hydroxy, alkoxy, haloalkoxy, carboxy, or carboxamido.

12. A compound of claim 1 where $N(R^6)(R^7)$ taken together is a [4.2.0,], [4.3.0,], [4.4.0,], [4.5.0,], [4.6.0,], [5.2.0,], [5.3.0,], [5.4.0,], [5.5.0,], [5.6.0,], [6.2.0,], [6.3.0,], [6.4.0,], [6.5.0,], [6.6.0,] spirocyclic amine.

13. A composition useful for treating HIV infection comprising a therapeutic amount of a compound of claim 1 and a pharmaceutically acceptable carrier.

14. A method for treating HIV infection comprising administering a therapeutically effective amount of a compound of claim 1, or a pharmaceutically acceptable salt thereof, to a patient in need thereof.

* * * * *